(12) United States Patent
Ackland et al.

(10) Patent No.: US 10,019,721 B2
(45) Date of Patent: Jul. 10, 2018

(54) CLASSIFICATION SYSTEM AND METHOD

(71) Applicant: Performance Lab Technologies Limited, Auckland (NZ)

(72) Inventors: Jonathan Edward Bell Ackland, Auckland (NZ); Kerri Anne McMaster, Auckland (NZ)

(73) Assignee: Performance Lab Technologies Limited, Auckland (NZ)

( * ) Notice: Subject to any disclaimer, the term of this patent is extended or adjusted under 35 U.S.C. 154(b) by 0 days.

(21) Appl. No.: 15/591,338

(22) Filed: May 10, 2017

(65) Prior Publication Data

US 2017/0316425 A1    Nov. 2, 2017

Related U.S. Application Data

(63) Continuation of application No. 13/581,062, filed as application No. PCT/NZ2011/000029 on Feb. 24, 2011, now Pat. No. 9,665,873.

(30) Foreign Application Priority Data

Feb. 24, 2010  (NZ) .......................... 583585

(51) Int. Cl.
*G06F 15/00* (2006.01)
*G06Q 30/02* (2012.01)
(Continued)

(52) U.S. Cl.
CPC ............. *G06Q 30/02* (2013.01); *A63B 24/00* (2013.01); *A63B 24/0062* (2013.01);
(Continued)

(58) Field of Classification Search
CPC . A63B 24/00; A63B 24/0003; A63B 24/0006; A63B 24/0059; A63B 24/0062; A63B 24/0075
See application file for complete search history.

(56) References Cited

U.S. PATENT DOCUMENTS 5,297,558 A    3/1994  Acorn
6,554,776 B1 *  4/2003  Snow ..................... A61B 5/222
                                                                482/9

(Continued)

OTHER PUBLICATIONS

Extended Search Report for EP Application No. 11747774.5 dated Apr. 28, 2016.

(Continued)

*Primary Examiner* — Lawrence Galka
(74) *Attorney, Agent, or Firm* — Lowenstein Sandler LLP

(57) ABSTRACT

The invention relates to a system and method for analysing an activity session. Data from a monitoring device worn by a user of the system for example is received over a period of time or distance and a classification system of the invention is utilized in real time or post session to determine the activities performed by the user during the session. The data collected relates to multiple parameters monitored during the activity session. The classification system defines an activity using a set of threshold criteria for a combination of parameters and therefore identifies a particular activity performed during the activity session when a combination of monitored parameters satisfies the threshold criteria for a particular activity. Determining the activities performed in this way allows for more useful interpretation of the data which in turn leads to more effective coaching advice and feedback for the user.

29 Claims, 15 Drawing Sheets

(51) Int. Cl.
*A63B 24/00* (2006.01)
*G06Q 50/22* (2018.01)
*A61B 5/0205* (2006.01)

(52) U.S. Cl.
CPC ......... *A63B 24/0075* (2013.01); *G06Q 50/22* (2013.01); *A61B 5/0205* (2013.01)

(56) References Cited

U.S. PATENT DOCUMENTS

| | | |
|---|---|---|
| 6,705,972 B1 | 3/2004 | Takano et al. |
| 7,254,516 B2 | 8/2007 | Case et al. |
| 7,827,000 B2 | 11/2010 | Stirling et al. |
| 8,187,182 B2 | 5/2012 | Kahn et al. |
| 8,566,272 B2 | 10/2013 | Fukumoto et al. |
| 8,718,672 B2 | 5/2014 | Xie et al. |
| 8,977,522 B2 | 3/2015 | Jallon |
| 2004/0043869 A1 | 3/2004 | Sato et al. |
| 2005/0033200 A1 | 2/2005 | Soehren |
| 2005/0172311 A1 | 8/2005 | Hjelt |
| 2006/0063980 A1 | 3/2006 | Hwang et al. |
| 2006/0172859 A1 | 8/2006 | Davis |
| 2007/0010720 A1 | 1/2007 | Mott |
| 2007/0135264 A1 | 6/2007 | Rosenberg |
| 2007/0219059 A1 | 9/2007 | Schwartz et al. |
| 2007/0232455 A1 | 10/2007 | Hanoun |
| 2008/0096726 A1 | 4/2008 | Riley et al. |
| 2009/0047645 A1* | 2/2009 | Dibenedetto ..... H04M 1/72563 434/258 |
| 2009/0063099 A1* | 3/2009 | Counts ................... G01C 21/20 702/188 |
| 2009/0275442 A1 | 11/2009 | Nissila |
| 2009/0319221 A1 | 12/2009 | Kahn et al. |
| 2010/0137106 A1 | 6/2010 | Oshima et al. |
| 2010/0292599 A1 | 11/2010 | Oleson |
| 2011/0152695 A1 | 6/2011 | Granqvist |
| 2012/0010478 A1 | 1/2012 | Kinnunen et al. |
| 2012/0221254 A1 | 8/2012 | Kateraas et al. |
| 2012/0316455 A1 | 12/2012 | Rahman et al. |

OTHER PUBLICATIONS

B. Harrison, S. Consalvo, & T. Choudhury. "Using Multi-Modal Sensing for Human Activity Modeling in the Real World," In H. Nakashima, H. Aghajan, & J.C. Augusto (Eds.) Handbook of Ambient Intelligence and Smart Environments, Springer Verlag, Part IV, (2009), pp. 463-478.

International Search Report for International Patent Application No. PCT/NZ2011/000029 dated May 9, 2011, 4 pages.

* cited by examiner

CLASSIFICATION SYSTEM AND METHOD

CROSS-REFERENCE TO RELATED APPLICATIONS

This application is a continuation of U.S. patent application Ser. No. 13/581,068, filed Nov. 6, 2012, which is a National Phase entry of PCT/NZ2011/000029, filed Feb. 24, 2011, which claims the benefit of priority to New Zealand patent application No. 583385, filed Feb. 24, 2010, the contents of each being hereby incorporated by reference herein in their entireties.

FIELD OF INVENTION

The invention relates to exercise and/or activity monitoring and in particular to classification of exercise or activity measurement data.

BACKGROUND

Devices for monitoring physiological information such as heart rate, and other exercise related information such as speed and distance exist. Such devices provide a means of representing the quality of the exercise conducted by a user wearing the device or exercising on a machine incorporating the device. It is often difficult for the user to effectively interpret this representation of quality or use it to compare it against their goals. The state of the art has therefore developed further to provide systems compatible with a particular measurement device for downloading and uploading exercise data to and from the device for processing, with the object of making the data more meaningful for the user. For example, systems are available which enable a user to upload a workout program onto a wearable exercise device. The user exercises according to the program while the device monitors the user's heart rate. Once the exercise is complete, the user downloads the monitored data to a computer to process the data in some cases against the workout program and provide statistics on that particular exercise session.

In the case of exercise, in at least some cases automated exercise devices are rigid in their approach to a user exercising. For example, a preloaded training workout may stipulate a 2 minute warm up followed by a 4 minute interval at a speed close to half marathon race pace followed by easy recovery running for 3 minutes before another 4 minute half marathon race pace effort. There are two fundamental problems with this. Firstly the user may reach a hill just before he/she starts the 4 minute half marathon race pace effort and have to run it up the hill. The user may then end up having to do the second 4 minute half marathon race pace effort just as they reach the crest of the hill and descend. This rigidity of set training for each activity within the workout or activity can mean that the user experience is poor and that the data obtained will have far greater variability and error within it, potentially making it almost meaningless to analyse and to draw conclusions from. Secondly without understanding the full context of the workout it is difficult for a trainer for example to comment effectively, without for example knowing the terrain or the resistance that the user is experiencing and this can mean interpretation may be reduced to guesswork.

Current systems can also be heavily dependent on the type of monitoring device used as they are generally limited to monitoring specific parameters e.g. heart rate for interpretation of the exercise. Furthermore, interpretation of exercise data in at least some current systems is dependent on pre-established assumptions of the user's exercise regime. In other words, the exercise data is processed with the assumption that the user is performing a specific type of exercise. These factors limit the diversity of the systems and in some cases their accuracy, should the user choose to divert from the type of exercise specified by a particular program. Lastly, the statistics provided by the system may still be meaningless to an unskilled user and would generally require the aid of a specialised trainer to interpret them and provide advice/guidance as to how to modify the user's exercise program so the user can meet their goals.

Exercise and activity devices that measure biometric and environmental data such as heart rate, speed, leg or arm turnover or stroke rate, altitude, temperature, R-R, power, slope, distance per turnover, location, distance and time currently exist. This data is displayed on a watch or device screen or spoken through headphones. These systems are merely measurement devices. This means that once the activity data is collected, the user must have the relevant level of skill to analyze and interpret it and then decide what changes they should make to their future exercise to optimize their time and effort during training and to maximize improvements.

FIG. 3 for example shows data downloaded from a measurement device. It is very difficult to extract any clear understanding or information from such raw data. Hundreds of millions of people around the world exercise ineffectively due to poor understanding of the appropriate strategies to maximizing fitness, sports performance and health improvements through activity. In most cases they do not have access to a coach.

In most cases, users ultimately do not want data from a measuring device, they want to know what was correct about what they did, what problems and solutions they need to work on and what to do next. They need someone or something to interpret the data and provide intelligent feedback.

When tracking a soldier in the field or a user engaging in health related activities throughout a full day, it has been difficult in the past to clearly establish different activities that have occurred during the day, and/or assess levels of fatigue or areas of weakness.

It is an object of the present invention to provide a method and system for classifying exercise and/or activity related data into different activities to provide an accurate representation of a particular exercise session or form of activity, or to at least provide the public with a useful choice.

SUMMARY OF THE INVENTION

In a first aspect the invention may broadly be said to consist of a method for analysing an activity session comprising:
    receiving activity data over a period of time or distance indicative of one or more activities performed during the activity session, said data relating to multiple parameters monitored during the activity session, and
    utilising a classification system to identify the one or more activities performed during the activity session based on the received activity data, a classification system defining an activity based on a set of threshold criteria for a combination of multiple parameters.

Preferably the data is received in multiple data streams of consecutive data points, each stream relating to one of said monitored parameters, and utilising said classification system comprises:
 a) comparing corresponding data points of two or more data streams against the set of threshold criteria for one or more activities,
 b) identifying when the corresponding data points satisfy the threshold criteria for an activity and if satisfied classifying the corresponding data points under the activity, and
 c) repeating steps a) and b) for other data points from the data streams to identify the one or more activities performed during the activity session.

Preferably the step of utilizing the classification system further comprises grouping consecutive data points classified under the same activity to define an instance of the activity within the activity session, the number of consecutive data points being indicative of duration of the instance of the activity.

Preferably the step of utilizing the classification system is performed upon or after receiving the activity data for the entire activity session.

Alternatively the activity data is received during the activity session and the step of utilizing the classification system is performed simultaneously during the activity session.

The activity data may be time stamped by a user during an activity session to denote an instance of an activity and said method comprises receiving one or more time stamped blocks of activity data and utilizing the classification system to identify an activity performed during one or more of the time stamped blocks.

Preferably the multiple parameters monitored are any combination of two or more of: resistance, effort, location, turnover, distance covered per turnover, positional status, ECG, blood pressure, ambient temperature, relative humidity, barometric pressure, heat index, local wind speed, local wind direction, local rain, body weight, carried weight, vertical jumping height, horizontal jumping distance, drop, climb, crawl, heading direction, oxygen uptake, respiration, ventilation, energy expenditure, energy intake, R-R (HRV), body temperature, weather condition, degree of movement, ground status, and direction user facing.

Preferably the combination of monitored parameters for defining an activity includes a measure of resistance or change in resistance and a measure of effort or change in effort.

The measure of effort or change in effort may be a measure of speed or change in speed, a measure of heart rate or change in heart rate, or a measure of power or change in power, or any combination thereof.

The measure of resistance or change in resistance may be a measure of altitude or change in altitude, a measure of slope or change in slope, or a measure of gradient or change in gradient, or any combination thereof.

Alternatively or in addition, the measure of resistance or change in resistance may be a determined from stride rate or change in stride rate, stroke rate or change in stroke rate, or cadence or change in cadence, or any combination thereof.

Preferably the classification system comprises any one or more of a weight loss activity classification, an activity status monitoring classification, a running classification, a cycling classification, a rowing/kayaking classification, a field sports classification, a pedometer activity monitoring classification, and a horse training classification.

Preferably the data relating to the parameters monitored during the activity session is obtained from one or more activity monitoring devices.

Preferably the method further comprises processing data classified under an activity to determine a level of compliance with a predetermined training plan.

Preferably the method further comprises updating a training plan based on the level of compliance.

In a second aspect the invention may broadly be said to consist of a system for analysing an activity session comprising a classification module arranged to receive activity data indicative of one or more activities performed during the activity session, said data relating to multiple parameters monitored during the activity session and having:
 at least one memory component for storing one or more classifications for defining one or more activities, each activity being defined based on a set of threshold criteria for a combination of multiple parameters, and
 at least one processor arranged to utilise the classifications to process the received activity data and identify one or more activities performed during the activity session.

Preferably the classification module is arranged to receive the data in multiple data streams of consecutive data points, each stream relating to one of said monitored parameters, and said processor is arranged to utilize the one or more classifications by:
 a) comparing corresponding data points of two or more data streams against the set of threshold criteria for one or more activities,
 b) identifying when the corresponding data points satisfy the threshold criteria for an activity and if satisfied classifying the corresponding data points under the activity, and
 c) repeating steps a) and b) for other data points from the data streams to identify the one or more activities performed during the activity session.

Preferably the processor is further arranged to group consecutive data points classified under the same activity to define an instance of the activity within the activity session, the number of consecutive data points being indicative of a duration of the instance of the activity.

Preferably the processor is arranged to process the activity data upon or after receiving the activity data for the entire activity session.

Alternatively the processor is arranged to process the activity data upon receiving activity data during the activity session.

The data may be received in time stamped blocks and the processor may be arranged to utilize the one or more classifications to process one or more of the time stamped blocks of data and identify an activity performed during each of the one or more blocks.

Preferably the multiple parameters monitored can be any combination of two or more of: resistance, effort, location, turnover, distance covered per turnover, positional status, ECG, blood pressure, ambient temperature, relative humidity, barometric pressure, heat index, local wind speed, local wind direction, local rain, body weight, carried weight, vertical jumping height, horizontal jumping distance, drop, climb, crawl, heading direction, oxygen uptake, respiration, ventilation, energy expenditure, energy intake, R-R (HRV), body temperature, weather condition, degree of movement, ground status, and direction user facing.

Preferably the combination of monitored parameters for defining an activity includes a measure of resistance or change in resistance and a measure of effort or change in effort.

The measure of effort or change in effort may be a measure of speed or change in speed, a measure of heart rate or change in heart rate, or a measure of power or change in power, or any combination thereof.

The measure of resistance or change in resistance may be a measure of altitude or change in altitude, a measure of slope or change in slope, or a measure of gradient or change in gradient, or any combination thereof.

Alternatively or in addition, the measure of resistance or change in resistance may be determined from stride rate or change in stride rate, stroke rate or change in stroke rate, cadence or change in cadence, or any combination thereof.

Preferably the memory component has stored therein any one or more of a weight loss activity classification, an activity status monitoring classification, a running classification, a cycling classification, a rowing/kayaking classification, a field sports classification, a pedometer activity monitoring classification, and a horse training classification.

Preferably the system further comprises one or more activity monitoring devices, each arranged to obtain data indicative of parameters monitored during an activity session.

Preferably the classification module is remote from the one or more monitoring devices and each monitoring device is arranged to transmit the data indicative of the monitored parameters to the classification module.

Preferably the system further comprises:
a central station for accommodating the classification module, and
a receiver for receiving data indicative of multiple parameters monitored during an activity session from the one or more monitoring devices.

Alternatively the classification module is housed within each monitoring device.

Preferably the system further comprises an interpretation module having a processor for processing data classified under an activity to determine a level of compliance with a predetermined training plan.

Preferably the system further comprises a plan generation module having a processor for updating a training plan based on the level of compliance determined by the interpretation module.

In a third aspect the invention may broadly be said to consist of a classification system for analysing activity data relating to multiple parameters monitored during an activity session to determine one or more activities performed during the activity session, the classification system comprising:
at least one memory component for storing one or more classifications for defining one or more activities, each activity being defined based on a set of threshold criteria for a combination of parameters, and
at least one processor arranged to utilise the classifications to process the activity data and identify one or more activities performed during the activity session.

Preferably the classification system is arranged to receive the data in multiple data streams of consecutive data points, each stream relating to one of said monitored parameters, and said processor is arranged to utilize the one or more classifications by:
a) comparing corresponding data points of two or more data streams against the set of threshold criteria for one or more activities,
b) identifying when the corresponding data points satisfy the threshold criteria for an activity and if satisfied classifying the corresponding data points under the activity, and
c) repeating steps a) and b) for other data points from the data streams to identify the one or more activities performed during the activity session.

In this specification activity or activity type can mean any type of action performed by an individual or group of individuals over a period of time or distance (or both) which may or may not involve movement, such as lying/sitting down and running/cycling. The term is intended to cover general activities such as running as well as specific activities such as running uphill at a certain pace. An activity session or workout means a period of time where an individual performs one or more activities. Exercise and exercise sessions (or workout) are intended to be covered by the terms activity and activity sessions respectively. Activity period refers to the period within an activity session in which an activity is performed. Training type is also intended to fall within the meaning of activity. Training zone is intended to mean a threshold zone or criteria for a single parameter that defines an aspect of an activity. An activity is composed of training zones from multiple parameters.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner. The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION

1. Virtual Coach System Overview

Figure 1:
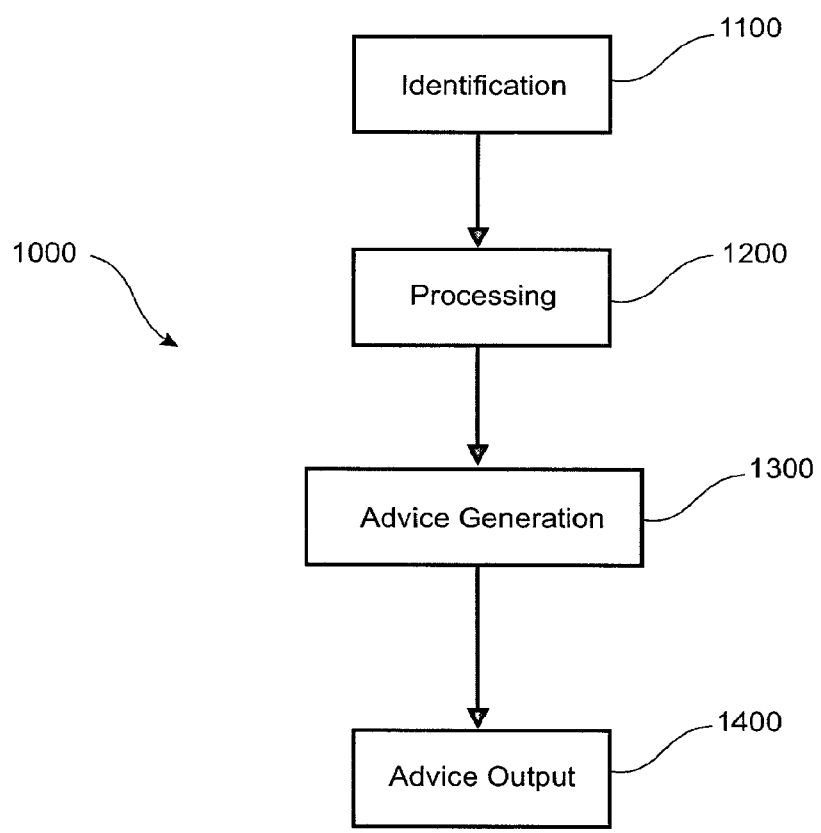
FIG. 1 is a flow diagram showing an overview of a preferred method of activity analysis of the invention.
Figure 2:
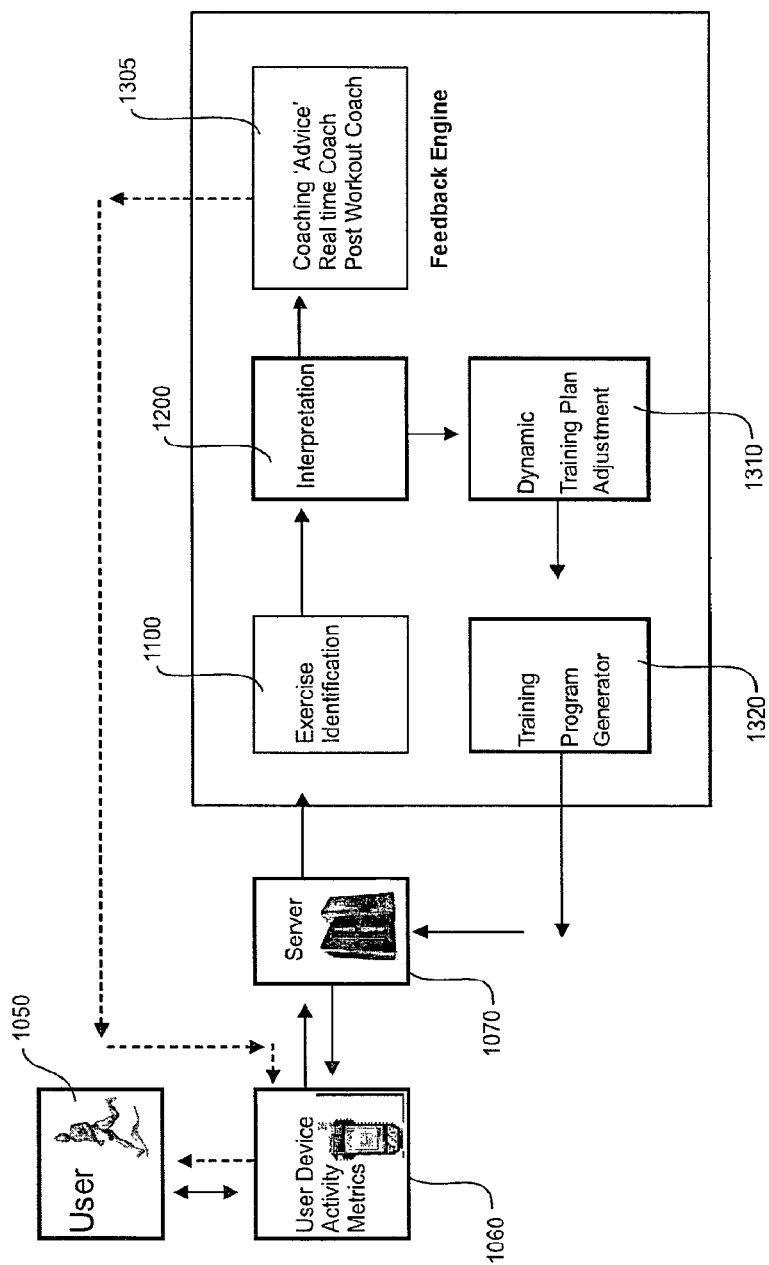
FIG. 2 is a block diagram showing a preferred system for carrying out the method of FIG. 1.
Figure 3:
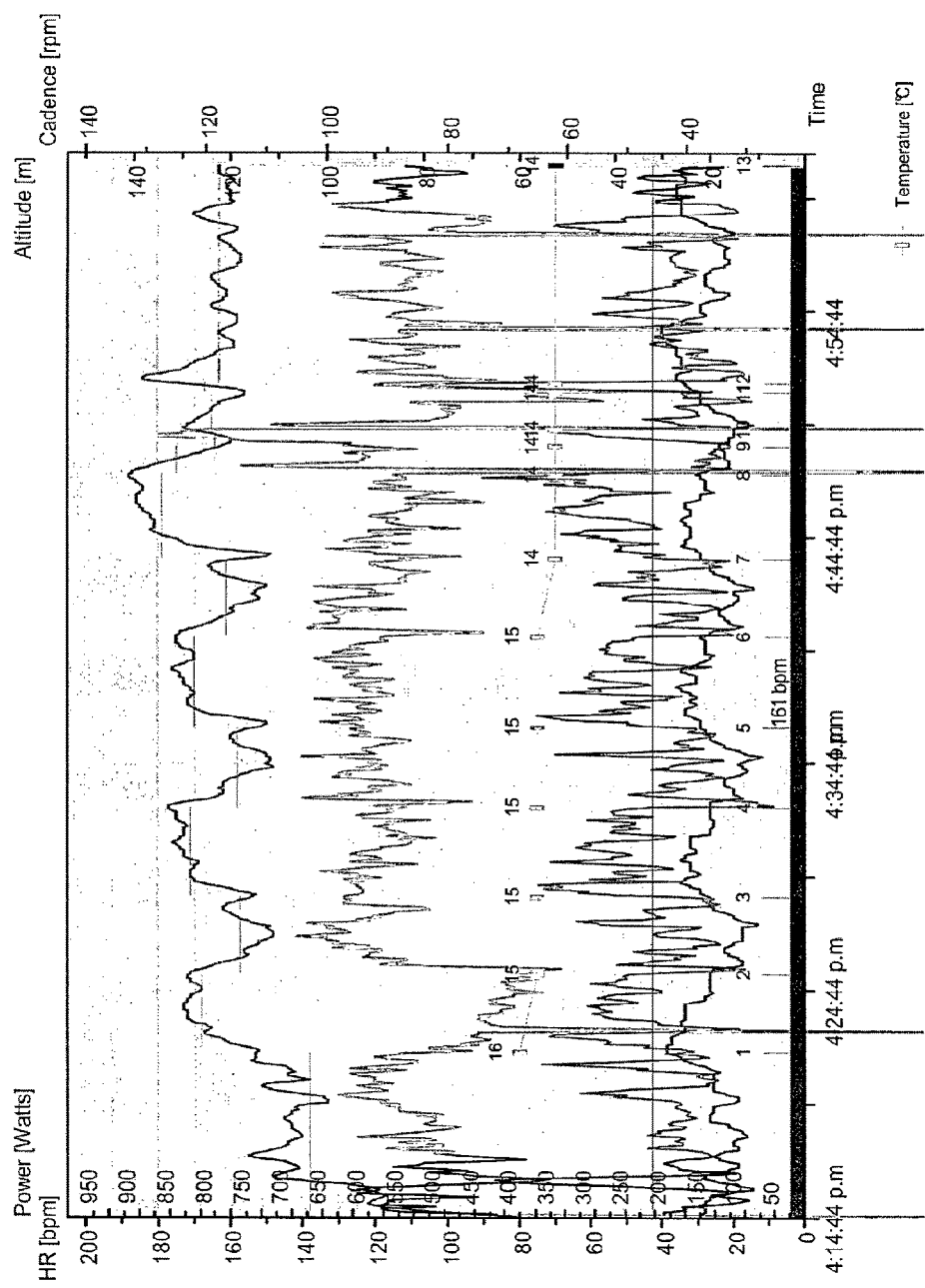
FIG. 3 is graph showing example data downloaded from a monitoring device.

Referring to FIGS. 1 and 2, an overview of a preferred method and system 1000 for analysing an activity session is shown. Like method steps and system components are given the same reference numerals. A user 1050 of the system engaging in an activity session, either prior to or whilst the system is being used, gathers information/data related to the activity/activities performed during the session, preferably using at least one exercise/activity monitoring device 1060 and supplies it to the system (which may be hosted by a server 1070) to gain feedback and/or advice/guidance in relation to their fitness goals. The information is received by the system either manually via the user initiating uploading of the information from the monitoring device or automatically via the monitoring device, or from some other source for analysis, and is received and/or analysed either during activity or post activity. The system may be part of the monitoring device or may be separate, running on a personal computer for example, or a remote server 1070 accessible by and in communication with a personal computer and/or one or more monitoring devices.

During analysis the system will identify at step 1100 the different types of activities the user has engaged in (or is engaging in) during the activity session. A classification system or module 1100, which will be described in more detail below, is used by the system to identify the activities performed by the user from the activity information/data received. The classification system 1100 enables the overall system to partition the data into one or more data streams or blocks relating to the one or more activities performed by the user during the activity session. The data can then be processed at step 1200 while taking the type of activity performed into consideration. The classification system 1100 defines an activity based on at least one satisfied threshold criteria from multiple monitored parameters (other than distance or time or both which define the length of the activity or activity session but not the type of activity). The classification system 1100 defines an activity using multi-parameter zones (i.e. one or more threshold criteria from more than one parameter) that may occur within an activity session. This for example may be that during running any speed over 7 km/hr where the user has a change in altitude is defined as a 'hill climbing during running' activity, or any period that involves the user moving at 12-14 km/hr, while an accelerometer detects at least 160 steps per min over the period and while altitude does not change (flat), is defined as a 'running speed work' activity.

In accordance with the invention classified activities are identified using multiple data streams first (each stream being associated with one of the parameter(s) used to define a particular classified activity for example), then the data for the activity is processed specific to the defined activity as opposed to differently classified or non-classified activities that have slightly different definitions. The effect each type of activity/exercise has on the user's overall fitness, performance or fatigue is different and therefore it is necessary to distinguish between them to provide satisfactory analysis and appropriate feedback/advice. In some embodiments the data once classified is processed/interpreted by an interpretation module 1200 for the various identified activity types to translate collective activity data into a tutorial or advice (step 1300) for example. The data may be processed with or without the rest of the activity session data. The data relating to a particular activity may be processed 1200 against a plan, historic data, an ideal zone (the zone all users would ideally fall under—not specific to the history of the individual but rather applies to all individuals, e.g. an ideal zone for example is a pedal cadence of between 85 and 95 revolutions per minute for all cyclists riding at an easy pace), a threshold or environmental conditions for example. In some embodiments a response is generated from the output of the processing stage 1200 which may be advice provided in the form of a prescription (method for modifying a plan 1305) or a solution (method for modifying how a user engages in an activity 1310) for example. Coaching advice or feedback 1310 may be provided by the system back to the monitoring device 1060 in real time or post workout for instance. The advice may be output (step 1400) in either a text, auditory or graphical form as opposed to a visual or auditory display of raw or derived exercise data in real time or post activity. In addition or alternatively a training plan adjustment module 1310 modifies the training plan 1320 for the user based on the output of the interpretation module 1200 and stores the new training plan 1320 for future use by the user 1050.

Advice is a preferable feature of the invention and may alternatively not be supplied by the system but from a trainer or some other source for example.

In one embodiment the data is automatically received by the classification system in one or more streams and then trawled, with the data points being compared against one or more threshold criteria associated with the parameter relating to that stream. In an alternative embodiment the system may be arranged to enable a user to manually time stamp a block of activity data (e.g. by pushing a time stamp or lap split button on a device) and the time stamp block for each monitored parameter is then trawled and compared against the one or more threshold criteria. For both embodiments corresponding data points of the multiple streams or blocks (that relate to multiple parameters associated with a particular activity) are associated with a particular activity when the system recognizes that the data points satisfy the threshold criteria defining that activity, and therefore associates the corresponding data points with the activity.

2. Classification

The classification system enables activity session data to be classified into one or more activity types. The classification system has knowledge of one or more activity types and their specific relationship with multiple parameters to achieve this. This knowledge may be simple or complex based on the application and/or desired accuracy of the system. Generally, one or more threshold criteria such as values or zones associated with each parameter related to a particular activity must be satisfied for that activity to be performed. In other words, an activity can be identified by the classification system when every threshold criteria is satisfied for each of a combination of parameters that define that activity. As will be explained in more detail further below, the classification system of the invention utilises multiple parameters to define activities.

An activity may be identified from different combinations of parameters. This diversifies the compatibility of the system with different monitoring devices. For example, an 'easy walking' activity may be defined by a stride rate threshold (such as less than 60 steps per minute) and a terrain threshold (such as a gradient of less than 2°), or a speed threshold (less than 8 km/hr) and a terrain threshold (gradient of less than 2°), or a heart rate threshold (such as between 40 and 110 beats per min) and a terrain threshold (such as a gradient of less than 2°). This allows for different types of monitoring devices to be used alongside the system. For instance a mobile phone with GPS capability for measuring speed can be the monitoring device, or a more advanced device such as those branded under Polar, Suunto, Timex, Garmin, Adidas or Nike can be used for measuring heart rate and other parameters such as speed, altitude, distance, time and turnover (e.g. stride rate).

Overview

For effective coaching direction to be generated, the data that is obtained from a user engaged in exercise is preferably broken up into differing activities and/or different instances of activities that occurred during an exercise session. To achieve this, the activity classification system and method of the invention is employed.

In broad terms the classification system receives activity data over a period of time or over a distance that is indicative of one or more activities that were performed during the an activity session. This data relates to multiple parameters monitored during the activity session and preferably monitored through a monitoring device worn by the user. The classification system consists of a library of definitions for various activities which it consults upon receiving the activity data. From the definitions, the classification system can identify the one or more activities performed. The definitions classify an activity based on a set of threshold criteria from a combination of monitored parameters (i.e. multiple parameters each having at least one threshold criteria).

In the preferred embodiment, the activity data is received in multiple data streams, each relating to one of the monitored parameters. The classification system would then trawl through the data streams and place corresponding data points from different streams up against threshold criteria for different activities until it identifies compliance with the definition of a particular activity. Repeating this would then identify the one or more activities performed during the activity session. Consecutive data points in a stream belonging to the same activity classification define an instance of that activity during an activity session and this can further be used for interpretation of the session. The number of consecutive data points within the instance would be indicative of the duration of the instance of the activity. The duration may be a measure of time or distance depending on how the monitoring device gathered the data. In other words, the monitoring device may be arranged to sense a particular parameter after a certain distance travelled by the user, or after a certain period of elapsed time. In either case the number of data points conforming to a particular activity will indicate the duration of that instance of the activity during the session.

The classification system may be utilised upon receiving all the activity data for the entire activity session or simultaneously while data is being obtained by the monitoring device. A user may alternatively time stamp a block of data upon termination of an activity and forward this data to the classification system which would then automatically identify the instance of activity from the time stamped block.

Figure 4:
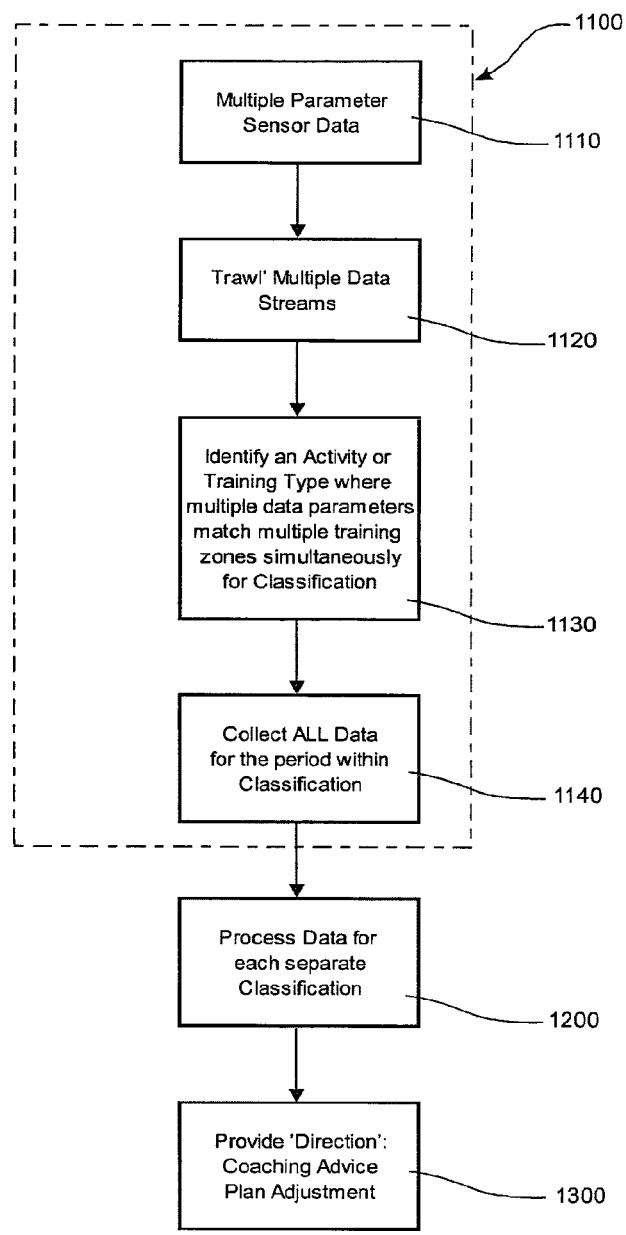
FIG. 4 is a flow diagram showing mainly an overview of the steps performed by the classification system of FIG. 2.

FIG. 4 shows a simplified flow diagram of the operation of the classification system 1100 of the invention. As the user exercises or after the user has exercised, multiple parameter sensor data is received 1110 by the classification system 1100. The system trawls this data for patterns in the multiple streams of data generated 1120 and identifies an activity upon determining compliance by the multiple parameter data with the multiple activity zones that define the activity 1130. Each time a match for all parameter zones defining an activity is determined the data stream for each parameter is logged and labelled 1140. The classified activity data is then ready to be interpreted for advice generation.

Figure 5:
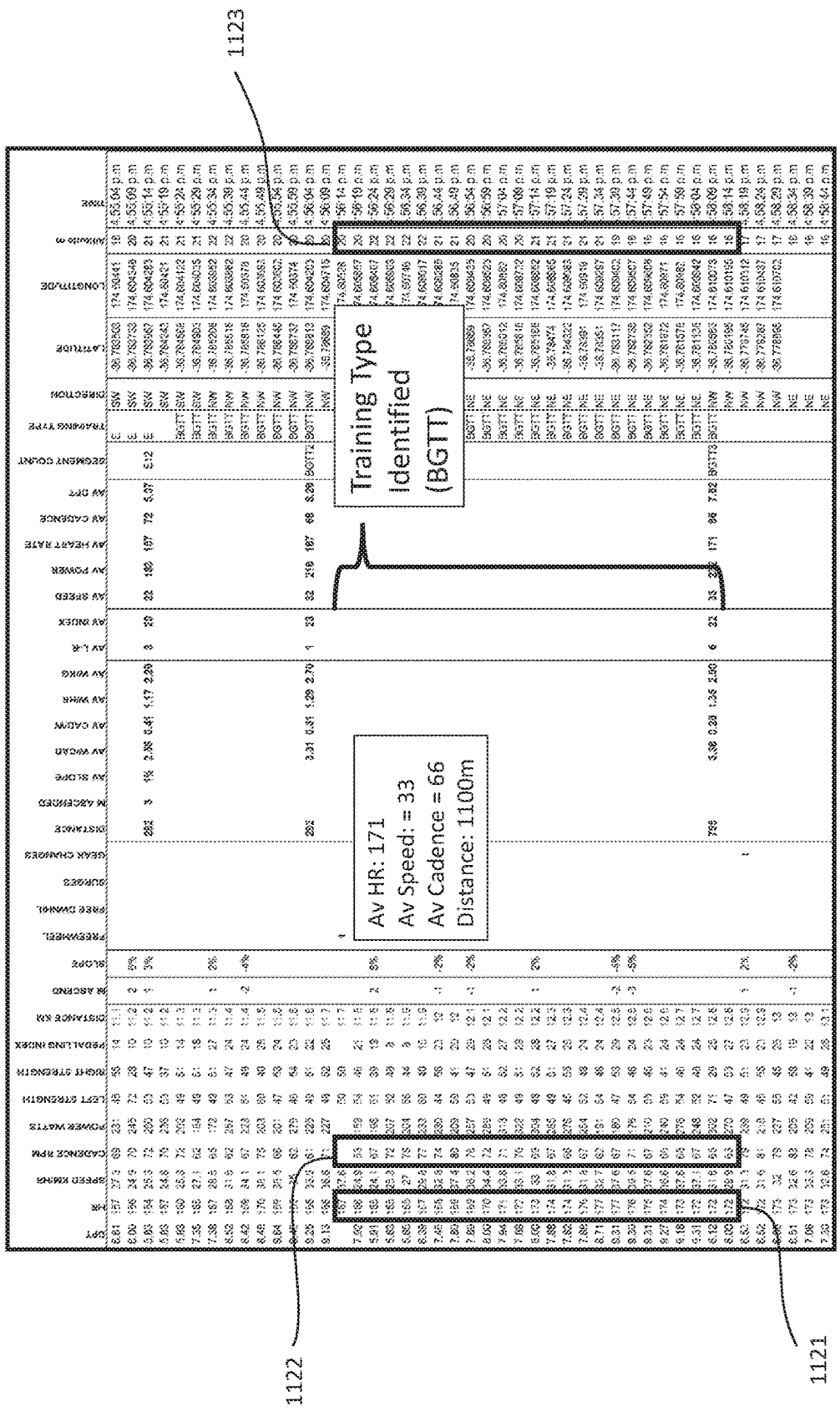
FIG. 5 shows an example data trawled by the preferred classification system of the invention to find a match within a larger data set of a workout for a particular activity type.

FIG. 5 shows an example of trawled data and finding a 'match' within a larger data set of a workout for a particular activity type. The dark highlighted streams 1121, 1122 and 1123 show three parameters (heart rate, cadence and altitude respectively) that satisfy the threshold zones for defining a big gear time trial (BGTT) cycling activity. The highlighted portion of at least those three data streams 1121, 1122 and 1123 are logged and labelled BGTT.

Figure 6:
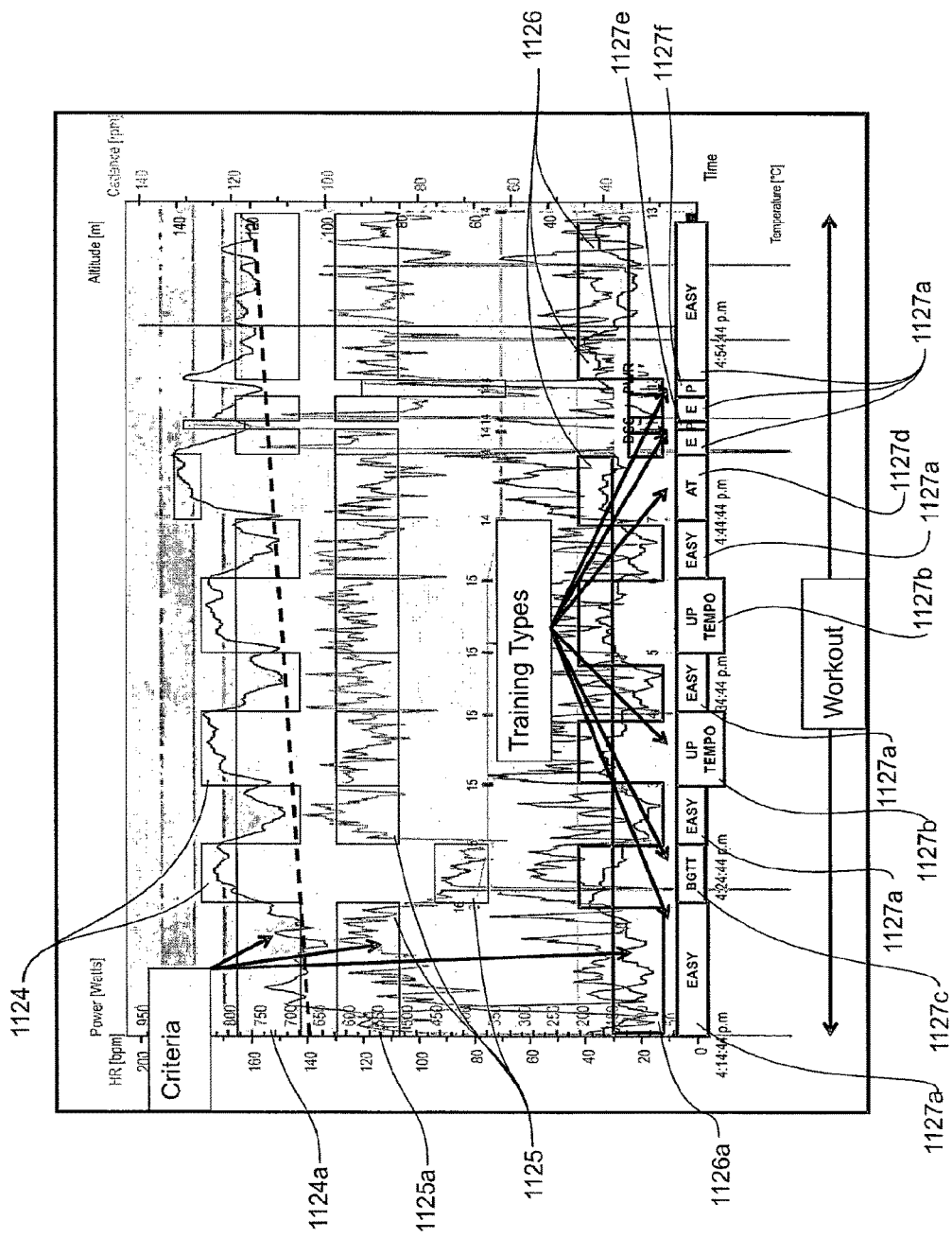
FIG. 6 shows an example graph where classification of cycling exercise data is partitioned into activity segments/types.

The classification system automatically recognises and partitions a monitored exercise/workout into a series of classified activity segments over the workout duration. FIG. 6 shows an example graphic where classification of cycling exercise data is partitioned into activity segments/types. In this example, heart rate, cadence and altitude are being (or have been) measured over the duration of the workout. Parameter zones 1124, 1125 and 1126 are the boxed regions defining particular threshold zones for each of the heart rate, cadence and altitude parameters respectively. These zones/criteria are used to define classifications of different activity segments/types. The identified activity types are shown along the horizontal axis of the graph. (e.g. Easy, BGTT, Up Tempo etc.). The entire workout has therefore been segmented into a series of activity types/segments using the classification system. Classification is critical to interpretation and coaching advice as it allows processing and interpreting data within an activity segment or between activity segments that contains the same label. It breaks all the possible ways the user can train down into its component parts or 'building blocks'. In the FIG. 6 example there are:

7 classified Easy training type segments (1127*a*)
   2 Up Tempo training type segments (1127*b*)
   1 Big Gear Time Trial training type segment (1127*c*)
   1 Race Pace training type segment (1127*d*)
   1 Downhill Spinning Sprint training type segments (1127*e*)
   and 1 Power training type segment (1127*f*)

Activity Types and Training Zones

Figure 7A:
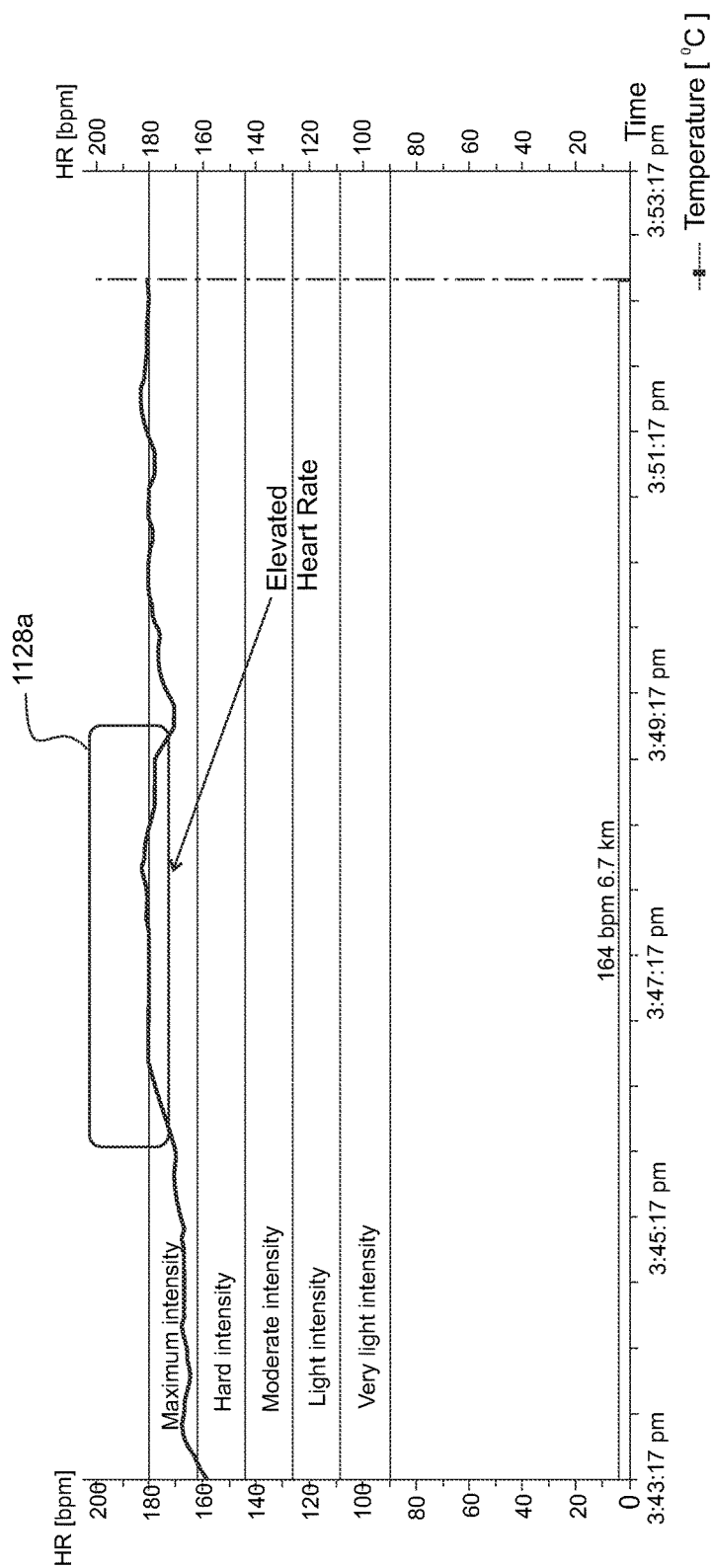
FIG. 7a shows a graph with different highlighted training zones for a monitored heart rate data.
Figure 7B:
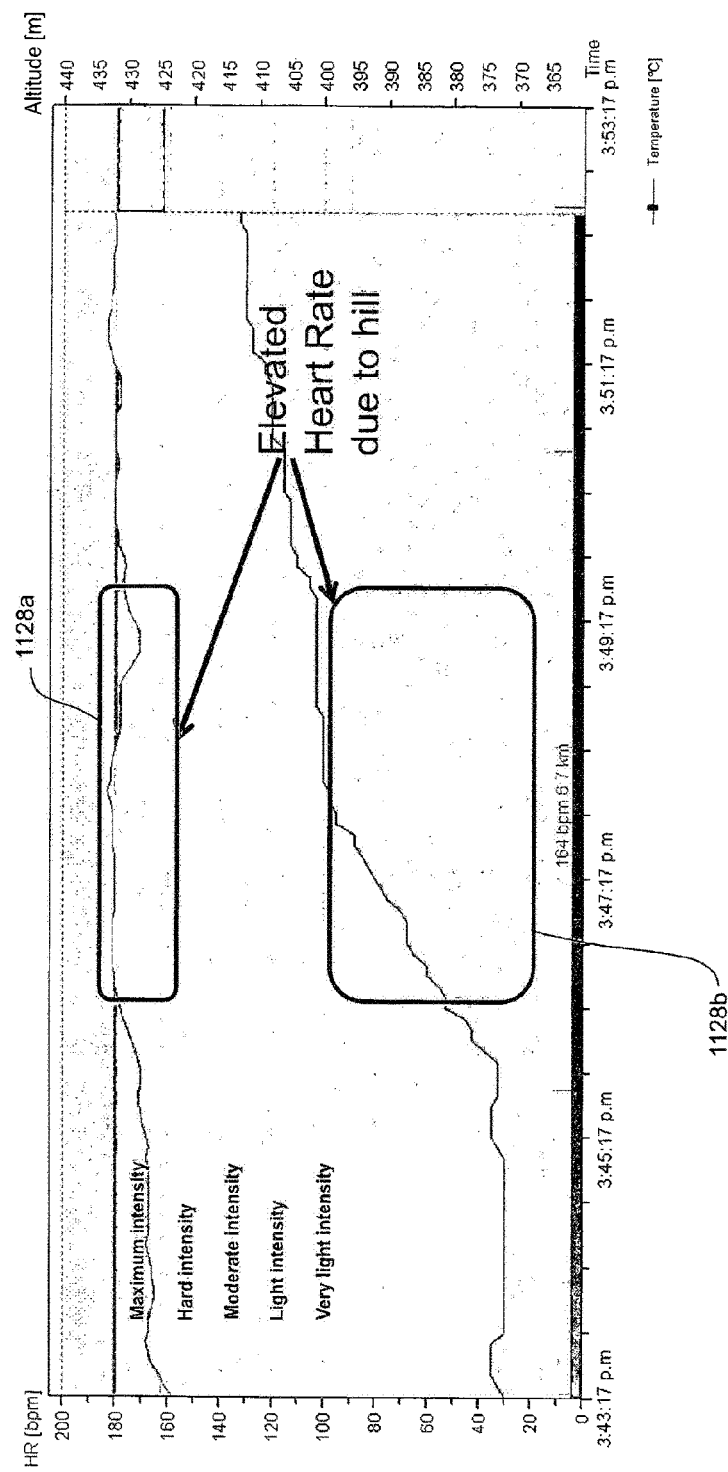
FIG. 7b shows the same graph as FIG. 7a with monitored terrain data.

There are systems currently available where zones can be classified and data can be recorded if it conforms to the prescribed parameter threshold. The data is generally classified as a 'Training Zone' and the system measures or outputs 'Time in Zone'. Multiple parameters are not recorded in concert to classify an activity type in these systems and therefore they cannot be used effectively for the purposes of automated interpretation and coaching direction and modification of a plan. FIG. 7*a* shows different highlighted training zones for the heart rate parameter. In a scenario where heart rate is the only parameter used to interpret an exercise, a runner may be running briefly at too high a heart rate 1128*a* which could be interpreted as training too hard but without other parameters this could be incorrect. Referring now to FIG. 7*b*, if altitude change is also recorded, one can deduce that the runner was actually running up a hill 1128*b* and this being the reason for the high heart rate 1128*a* recorded. This is different to a runner sprinting on the flat with a high heart rate. The combination of parameters describes the situation adequately enough to understand what is happening and therefore allows interpretation.

In essence, activity types defined by the classification system are made up of these training zones (e.g. an easy training type is made up of three training zones 1124*a*, 1125*a* and 1126*a* shown in FIG. 6). Different activity types are combined to make up a workout. Workouts are combined into a calendar sequence over time to form a training plan designed to generate physiological improvements. Therefore training plans are made up of workouts, workouts are made up of activity types and activity types are made up of training zones. A training zone describes an aspect of an activity type. The classification system of this invention automatically partitions sensor data from a workout monitoring device, into related activities by identifying streams of data that conform to the multiple training zones defining that activity. The partitioned data can then be interpreted separately to provide a more accurate representation of the physiological effects of the workout which leads to effective coaching/plan modification.

EXAMPLE 1

Figure 8A:
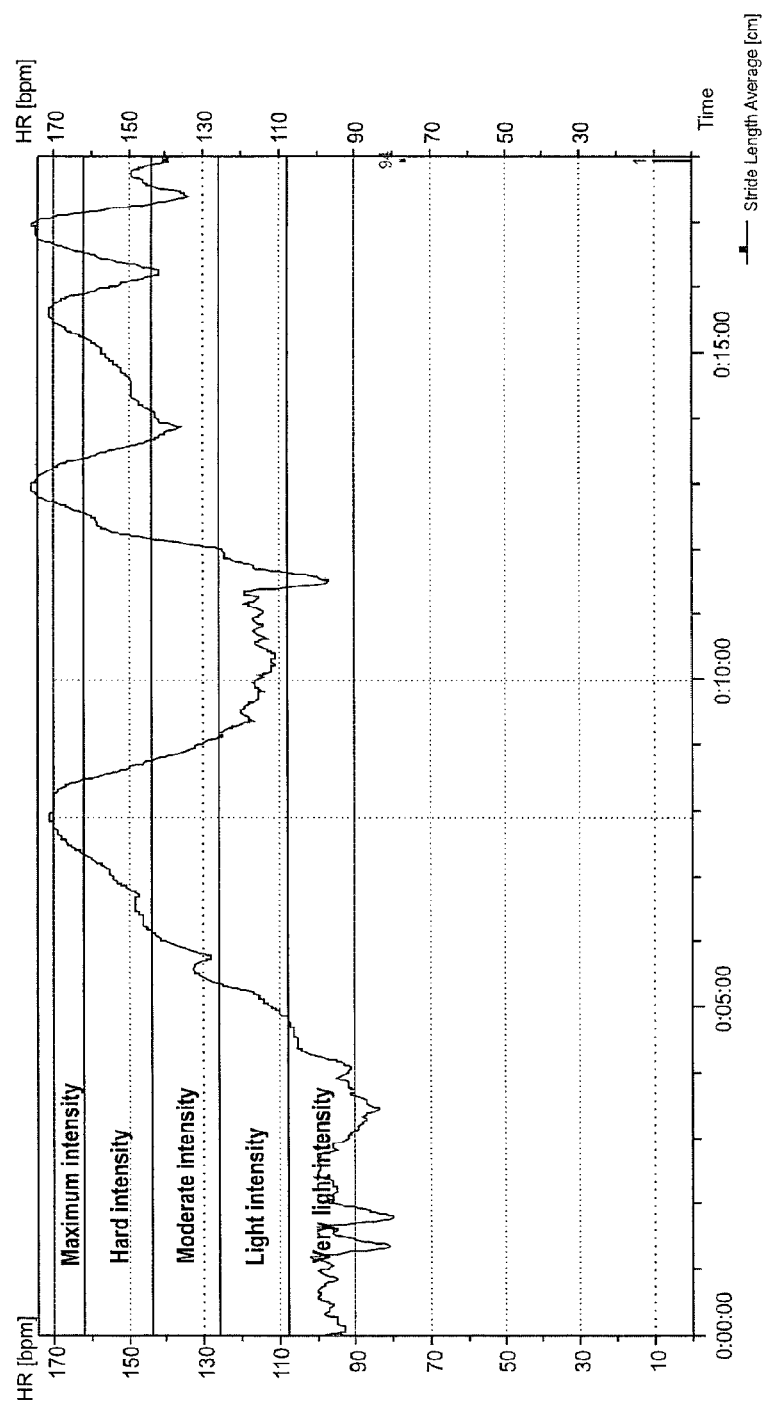
FIGS. 8a and 8b show example graphs of single and multiple monitored parameter data respectively.
Figure 8B:
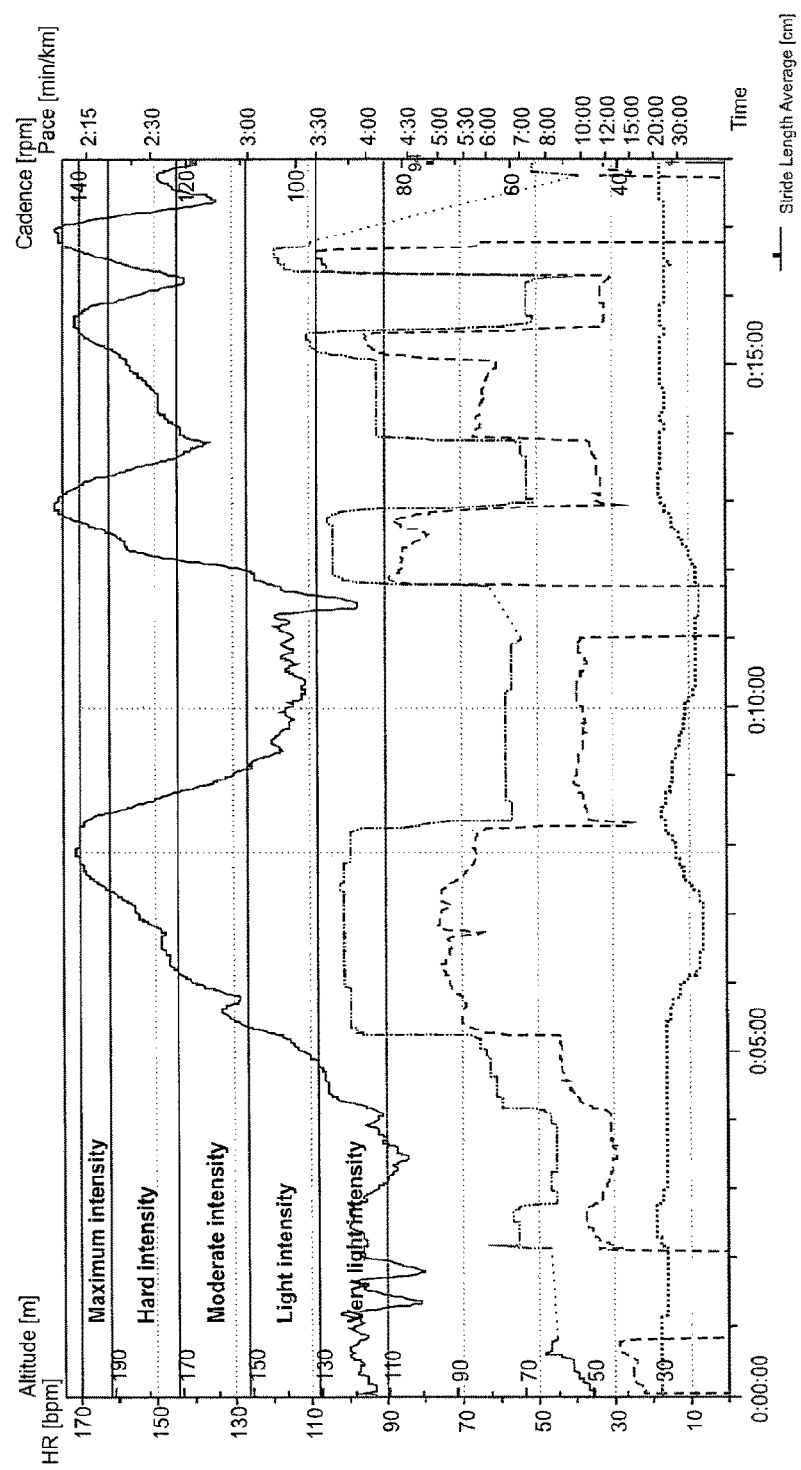
Figure 8C:
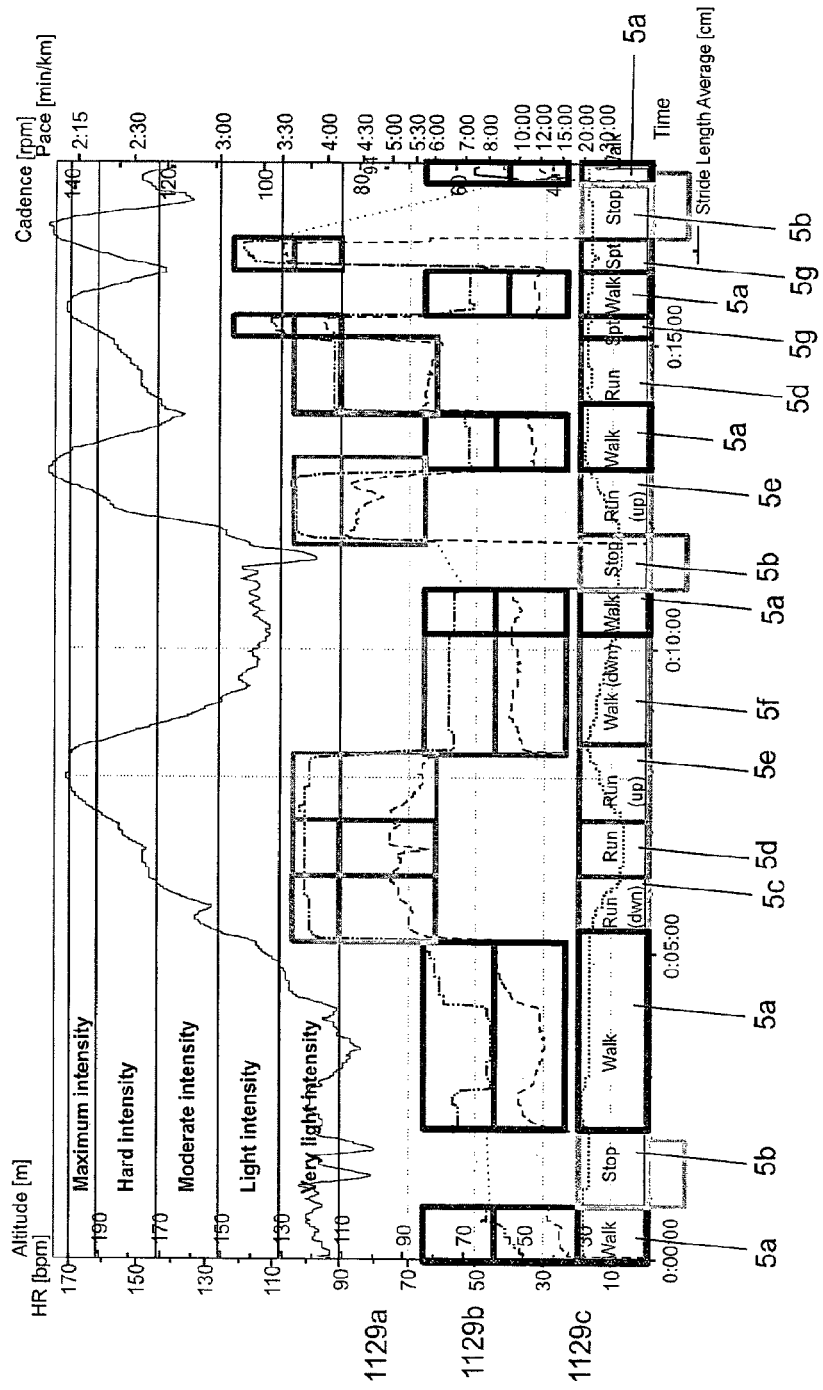
FIG. 8c shows the same graph as FIG. 8b with different activities classified by the classification system of the invention.

Referring to FIGS. 16a-c, a simplified example of the operation of the classification system is shown using graphs of monitored data. FIG. 8a shows the monitored heart rate throughout a workout or exercise session. It is difficult to identify what the user was doing during the exercise session with just data from this parameter. Even with multiple parameter data (terrain, speed and stride rate/cadence) plotted (as in FIG. 8b) it is difficult for the untrained user to determine what activities were performed during the workout session. Using the classification system of the invention enables comparisons between the multiple parameter data and threshold zones to be made thereby identifying associated activities the user is/was engaged in. In this case, as the data is being trawled, it is tested against defined threshold zones for cadence, speed and terrain. Different combinations of satisfied threshold zones define different activities. FIG. 8c shows how different activities are determined by the classification system from the monitored data. 1129a shows the monitored cadence, 1129b shows the monitored speed and 1129c shows the monitored terrain (altitude) during the workout. As these three data streams are trawled, the following activities are recognised from compliance with specific threshold zones (boxed regions) associated with the activities:

6 sections of walking on the flat 5a
3 stopped sections 5b
1 running downhill section 5c
2 running on the flat sections 5d
2 running uphill sections 5e
1 walking downhill section 5f
2 sprinting sections 5g

EXAMPLE TWO

Figure 9:
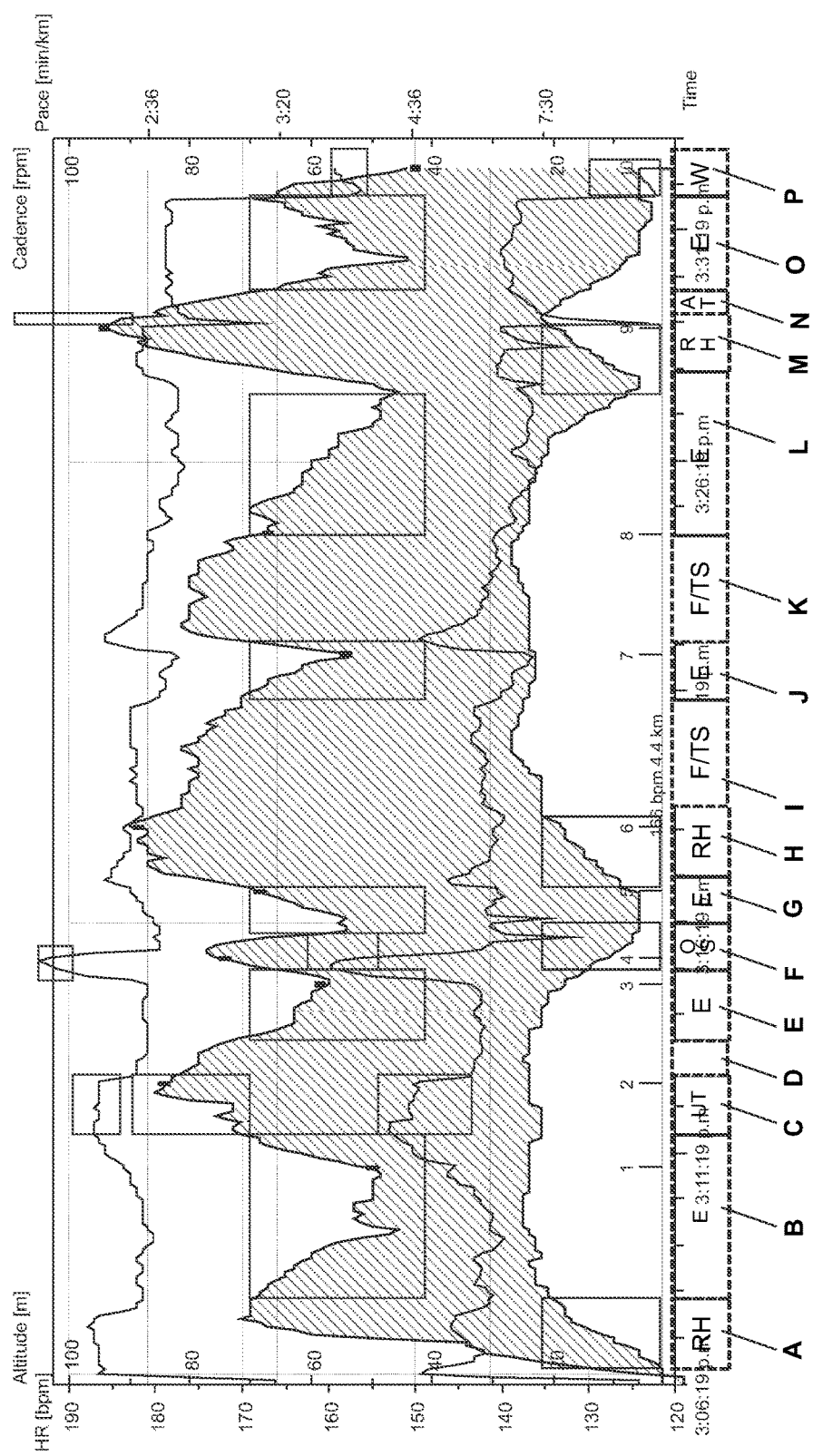
FIG. 9 shows another example graph with different activities classified from multiple parameter data.

FIG. 9 shows another example of application of the classification system to identify activities A-P within a workout session from multiple parameter data. Once again, the boxed regions represent the threshold zones within which the data from a particular parameter fits. Different combinations of threshold zones output different types of activities performed during A-P. For instance, during period A, the user is going up a small hill so his leg muscles are working hard. During period B, the user is on the flat and his heart rate is easy so he is carrying out an easy training type of activity. During period C, the user's speed, heart rate and cadence have increased as they travel along flat terrain meaning the user is engaging in an 'up tempo' training type of activity. During period D, the speed drops, the heart rate is up but dropping and the user is still travelling on the flat which suggests the user is recovering from the up tempo activity. During period E, the user has returned to an easy training type. During period F, the user starts travelling downhill with a high running cadence which suggests an 'overspeed' type of training. At period G the user returns to an easy training type. At period H, the user's heart rate goes up and they begin ascending a hill which identifies a 'Rolling Hill' training type. At I, the data cannot be categorized/classified as it does not fit within a predefined threshold zone. The user is likely to be recovering during this period before returning to another easy training type at J. During period K the user briefly tried to increase speed and heart rate to do an up tempo training type but this was not long enough to be accepted as a training type. Heart rate remained elevated for a while so no training type was identified and it remained uncategorized. The user returns to another easy training type at L. During M, the user started climbing a small hill which returned them to the rolling hill training type. During N a high heart rate on a flat terrain was identified meaning an anaerobic threshold training type was identified before returning to an easy training type at 0. Finally at P, the user lowered their pace to a walking pace to cease the workout.

Using the classification method of the invention, the activities determined as explained above were:

3 Rolling Hills (A, H, M)
1 Up Tempo (C)
1 Over speed sprint (F)
6 Easy (B, E, G, J, L, O)
1 Anaerobic Threshold (N)
1 Walking (P)

If single parameter training zones were considered only (i.e. not combinations of training zones as above) then the activities determined would have been:

4 Up Tempo efforts
6 Easy efforts
1 Anaerobic threshold Effort

Accurate classification therefore changes significantly when measuring activity types as opposed to training zones only. This has a large impact on the reliability of the coaching feedback and/or the ability to make the correct adjustments to a training program.

3. Preferred Embodiment(s)

The system and method of the invention may be implemented using the following classification system. This implementation should not be considered as limiting the scope of the invention but rather a preferred embodiment of the underlying classification concept defined above.

3.1 Minimum Activity Classification

The following is a list of the minimum activities to be classified by the classification system of one embodiment of the invention.

1. Walking, i.e. an individual moving at a speed below 8 km/hr. One monitored parameter and threshold criterion used to identify an individual walking can be a stride rate of less than 66 strides per minute. Alternatively or in addition, an effort/intensity measure/parameter more closely associated with the user's own ability may be used to classify walking. The threshold criteria for such a parameter may be a user heart rate (HR) of less than 60% of their maximum heart rate, and/or of less than 70% of their Anaerobic Threshold (AT) HR. Effort may alternatively or in addition be measured using speed and/or power, in which case the threshold criteria for walking may be less than 60% of the individual's AT speed and/or less than 60% of their AT power respectively. In addition to any combination of the above parameters and their threshold criteria, a flat terrain criterion is required by the classification system to identify a walking activity. In which case, the system may define a flat terrain for walking as an upward slope of less than 2° (or 4% gradient where consistent altitude (allowing for edge forgiveness—discussed in more detail in the Parameters section) cannot amount to more than a 6 meter altitude gain). A downward slope of as much as 8.5° (16% gradient) may also be regarded as a walking activity as would any uphill that fails to qualify as a hill (less than a 6 meter climb).
2. Easy running, i.e. jogging at 8-10 km/hr (for most people). One monitored parameter and threshold criterion used to identify an individual easy running can be a stride rate of greater than 70 strides per minute. Alternatively or in addition, an effort/intensity measure/parameter more closely associated with the user's own ability may be used to classify walking. The threshold criteria for such a parameter may be a user heart rate (HR) of 65-75% of their maximum heart rate, and/or of 70-80% of their Anaerobic Threshold (AT) HR. Effort may alternatively or in addition be measured using speed and/or power, in which case the threshold criteria for easy running may be 60-90% of the individual's AT speed and/or 60-90% of their AT power respectively. In addition to any combination of the above parameters and their threshold criteria, a flat terrain criterion may be required by the classification system to identify a walking activity. In which case, the system may define a flat terrain for easy running as an upward slope of less than 2° (or 4% gradient where consistent altitude (allowing for Edge Forgiveness— discussed in more detail in the Parameters section) cannot amount to more than a 6 meter altitude gain). A downward slope of as much as −8.5° (−16% gradient) may also be regarded as an easy running activity as would any uphill that fails to qualify as a hill (less than a 6 meter climb).
3. Flat terrain muscularly loaded activity (for example a big gear at a low cadence on a bike on the flat)—this classified activity is related to cycling and not walking/running as for the above two. One monitored parameter and threshold criterion used to identify an individual performing a muscularly loaded activity can be a big gear (e.g. 52×16). This parameter may be measured by distance travelled per pedal revolution with a threshold criterion of 65-75 pedal revolutions per minute. Alternatively or in addition, a threshold criterion of 85-130% of the AT distance per pedal turnover may be used. An effort/intensity measure/parameter more closely associated with the user's own ability may also or alternatively be used to classify a muscularly loaded activity. The threshold criteria for such a parameter may be a user heart rate (HR) of 65-75% of their maximum heart rate, or of −70-80% of their Anaerobic Threshold (AT) HR. Effort may alternatively or in addition be measured using speed and/or power, in which case the threshold criteria for flat terrain muscularly loaded may be 65-90% of the individual's AT speed and/or 65-90% of their AT power respectively. In addition to any combination of the above parameters and their threshold criteria, a flat terrain criterion is required by the classification system to identify a flat terrain muscularly loaded activity. The system may define a flat terrain for this activity as an upward slope of less than 2° (or 4% gradient where consistent altitude (allowing for Edge Forgiveness—discussed in more detail in the Parameters section) cannot amount to more than a 6 meter altitude gain). A downward slope of as much as −2° (−4% gradient) may also be regarded as flat terrain for a muscularly loaded activity.
4. Hills—This activity occurs when an individual increases their altitude during exercise/activity. The threshold criteria required to classify an activity under Hills can be a continuous rise over time that exceeds a 6 meter vertical gained from the flat, or a continuous slope of 2° or more (more or less) for more than 70 secs ('the more or less' in the above refers to our 'edge forgivness' system that will allow some out of zone/threshold values if the data falls back within zone or threshold criteria within a short period of time).
5. Speed—i.e. running at 12 km/hr or more (for most people). One monitored parameter and threshold criterion used to identify a speed activity can be a stride rate of greater than 70 strides per minute. Alternatively or in addition, an effort/intensity measure/parameter more closely associated with the user's own ability may be used to classify speed activities. The threshold criteria for such a parameter may be a user heart rate (HR) of more than 75% of their maximum heart rate, and/or of more than 80% of their Anaerobic Threshold (AT) HR. Effort may alternatively or in addition be measured using speed and/or power, in which case the threshold criteria for speed activities may be more than 90% of the individual's AT speed and/or more than 90% of their AT power respectively. In addition to any combination of the above parameters and their threshold criteria, a flat terrain criterion may be required by the classification system to identify a speed activity. In which case, the system may define a flat terrain for speed as an upward slope of less than 2° (or 4% gradient where consistent altitude (allowing for Edge Forgiveness—discussed in more detail in the Parameters section) cannot amount to more than a 6 meter altitude gain). A downward slope of as much as −2° (−4% gradient) may also be regarded as flat terrain for a speed activity.

There may be many different ways to classify an activity. Any combination of parameters such as speed, heart rate, power, turnover, distance per turnover, R-R (HRV), vertical meters ascended, slope, gradient can be used to depict a particular classification. Furthermore, there can be many ways to define the threshold or zone for each of these using a maximum value tested or obtained from within training or activity, using the Anaerobic or Aerobic Threshold value, or using averages based on the activity or exercise of the user etc.

The above monitored parameters and in particular the threshold criteria are only exemplary and reflect possible embodiments of the invention. They are not intended to be limiting. It is preferred in fact to have variations on the threshold criteria (and zones) for each individual as the system may be calibrated to their specific ability and needs.

3.2 Detailed Activity Classification

In a preferred embodiment of the invention, the classification system classifies activities within other major exercises or activities (which are referred to as categories in this specification). For instance weight loss, activity status monitoring (explained in more detail further below), running, cross country skiing, skating, cycling, horse training, rowing/kayaking, pedometer activity monitoring and field sport exercise categories may each have their own set of classified activities as set out below.

Activity Status Monitoring—Health/Military/Rescue Services

As the demand for effective Wellness schemes increases, the constant need for Rehabilitive Health technology upgrades continues and the ability to judge more effectively the condition and therefore safety of a soldier, fire or rescue services personnel automatically and remotely, the ability to classify activity and interpret it for the purposes of feedback and decision making become paramount.

Activity status monitoring uses sensors attached to an individual (in most cases) to analyse the 'situation' the individual is in or to assess the 'state' of the individual or a combination of the two. For example, multi axis accelerometers (such as 3D accelerometers) can determine whether an individual is upright or lying down. Sensors may be used to determine if an individual is stationary, or moving (running or walking), the speed that they are moving at and the direction they are moving in, whether the terrain is flat or hilly, whether it is cold or hot, windy or rainy, the altitude the individual is at, the location of the individual, the body temperature, heart rate, sweat rate, footfall, blood pressures, ECG etc. These measurements that are associated with the individual can be very useful in weight loss, health and military applications. The output from one or a combination of sensors will help determine the situation and/or state of the individual which may then be used by the classification system to identify which one of the following classified activities the user is engaging in.

1. Inactive
2. Inactive (Upright)
3. Inactive (Rest)
4. Inactive (Prone)
5. Easy Walking (forwards, backwards, lateral left or right)
6. Rolling Hills
7. Hills
8. Long Climbs
9. Fast Walking (forwards, backwards, lateral left or right)
10. Low Speed Run (forwards, backwards, lateral left or right)
11. High Speed Run
12. Out of Zone Specialist Categories for the above:

13. Sprint - Flat
14. Sprint - Uphill
15. Crawling (forwards, backwards, lateral left or right)
16. Climbing
17. Descending
18. Non specific movement - Low Activity
19. Non specific movement - Moderate Activity
20. Non specific movement - High Activity
21. Non specific movement - Very High Activity Walking/Running - Weight Loss Activity Classification 1. Inactive (Upright)
2. Inactive (Rest)
3. Inactive (Prone)
4. Easy Walking
5. Rolling Hills
6. Hills
7. Fat Burning Zone
8. Low Speed Run
9. High Speed Run
10. Out of Zone - Too fast Running Classification 1. Inactive
2. Easy
3. Rolling Hills
4. Hills
5. Long Climbs
6. Hill Efforts
7. Up Tempo
8. Anaerobic Threshold
9. Sprint
10. Overspeed
11. Bonus Out of Zone
12. Race Pace Cycling Classification 1. Inactive
2. Easy
3. Rolling Hills
4. Hills
5. Long Climbs
6. Hill Spinning
7. Hill Efforts
8. Flat Big Gear
9. Big Gear Time Trial
10. Up Tempo
11. Anaerobic Threshold
12. Power
13. Sprint
14. Overspeed
15. Bonus Out of Zone
16. Race Pace Rowing/Kayaking Classification 1. Inactive
2. Easy
3. Slow full pressure
4. Tempo Load
5. Up Tempo
6. Anaerobic Threshold
7. Race Pace
8. Starts
9. Moves
10. Bonus Out of Zone Field Sports Classification 1. Stationary - upright
2. Stationary - prone
3. <5 m sprints - moving Start
4. <5 m sprints - stationary start
5. 5-10 m sprints - moving start
6. 5-10 m sprints - stationary start
7. 10-20 m sprints - moving start
8. 10-20 m sprints - stationary start
9. 20-30 m sprints - moving start
10. 20-30 m sprints - stationary start
11. 30-40 m sprints - moving start
12. 30-40 m sprints - stationary start
13. 40+ m sprints - moving start
14. 40+ m sprints - stationary sart
15. Tempo Speed (forwards, backwards, lateral left or right)
16. Jogging (forwards, backwards, lateral left or right)
17. Slow Jogging (forwards, backwards, lateral left or right)
18. Walking (forwards, backwards, lateral left or right)
19. Jumping Vertical
20. Jumping Horizontal
21. Sidestep
22. Tackle
23. Bonus Out of Zone Pedometer Activity Monitoring 1. Inactive Rest
2. Inactive Stationary
3. Slow Walk
4. Fast Walk
5. Jog
6. Moderate Intensity Run
7. High Intensity Run
8. Non specific movement - Moderate Activity
9. Non specific movement - High Activity
10. Non specific movement - Very High Activity Horse Training Classification 1. STATIONARY
2. Easy (WALKING)
3. EASY (TROTTING)
4. Hills
5. Hill Efforts
6. Up Tempo (CANTER)
7. Anaerobic Threshold (GALLOP)
8. RACE PACE (FAST GALLOP)
9. Sprint
10. Bonus Out of Zone Some of the above activities are classified under more than one category and their definition under one category may therefore overlap with their definition under another. In the preferred embodiment the analysis system would be aware of the major exercise or activity category the individual is or was performing to avoid confusion between definition overlap.

3.3 Parameters

The monitored parameters aid the system in identification of activities performed during the exercise session, as each activity is defined by multiple threshold criteria (i.e. threshold values or zones) associated with multiple parameters.

In the preferred system associated with the activities defined above it is preferred to have a resistance parameter and an intensity/effort parameter.

For running, cycling, walking, horse training, and activity status monitoring categories the activities can be defined by the system using a terrain parameter as the resistance parameter and an effort parameter measured over time. The measure of terrain can be defined as a change in altitude, slope, gradient and/or resistance and may be obtained for example via a barometric device, a GPS device, a digital elevation model, or using the slope or gradient function on an exercise machine. The measure of effort may be defined using speed, heart rate or power (a direct measure or one derived from speed, body weight and slope).

For rowing and kayaking, there is no terrain component so a turnover parameter (e.g. stroke rate) is preferably used by the system in its place. The turnover parameter may also be used as the resistance parameter (in conjunction with terrain) to identify cycling activities.

For health or environmental monitoring, the classification is the incidence of a health (ECG, Blood Pressure) or environmental (Temperature, Heat Index, Wind Speed) parameter matched up to the other parameters that describe a situation (heart rate, terrain, speed etc).

It is preferable that the system caters for more parameters as this would enhance the flexibility of the system not just with accuracy and the ability to define more activities but also in terms of compatibility with a vast range of monitoring devices. A list of other possible additional parameters is shown below.

| 1. | Duration |
| 2. | Distance |
| 3. | Location |
| 4. | 'Turnover' (stride rate, cadence, stroke rate) |
| 5. | Distance covered per Turnover |
| 6. | Positional Status (is the person upright or lying down) |
| 7. | ECG |
| 8. | Blood Pressure |
| 9. | Ambient temperature |
| 10. | Relative Humidity |
| 11. | Barometric Pressure |
| 12. | Heat Index |
| 13. | Local Wind Speed & Direction |
| 14. | Local Rain |
| 15. | Some derived combinations (e.g. watts/kg) |
| 16. | Body Weight |
| 17. | Personal Gear - Carried Weight (e.g. tramping pack) |
| 18. | Jumping - vertical (varying heights) |
| 19. | Jumping - horizontal (varying distances) |
| 20. | Drop |
| 21. | Climbing |
| 22. | Crawling |
| 23. | Direction (heading) |
| 24. | Oxygen uptake |
| 25. | Respiration |
| 26. | Ventilation |
| 27. | Energy Expenditure |
| 28. | Energy Intake |
| 29. | Blood Pressure |
| 30. | ECG |
| 31. | R-R (HRV) |
| 32. | Body Temperature |
| 33. | Current weather |
| 34. | Degree of Movement |
| 35. | On the ground |
| 36. | Direction the user is facing or moving (forwards, backwards, sideways) |

3.4 Initial Calibration

Exercise, activity or training zones/criteria may to be calibrated to the individual so the zones conform to match correctly what the user experiences. The traditional calculations (e.g. 220- age in yrs and the Karvonen formula) and then percentages set against them which are used to determine the zones are only correct in 60% of individuals so another form of a more individualised assessment is preferably performed during a user's activity. One way to achieve this assessment is to establish what the user's Anaerobic Threshold is in a method that is safe for the user and not too complicated or invasive to the user's activity.

Anaerobic Threshold (AT) is a well known metric in exercise physiology that implies the maximum effort that a particular individual can exercise at for a particular period of time (e.g. 20 minutes to 1 hour) depending on their fitness. This can be at a heart rate of 170-180 beats per minute for one individual with a high heart rate and high Anaerobic Threshold or can be 140-150 for an older individual with a low Anaerobic Threshold for example. AT can similarly be measured with speed and power. There are preferably four systems to determine AT due to the fact that it must be compatible across a wide range of hardware platforms each using different sensor data.

User Rating Calibration System—The user does a calibration workout where they exercise to several set intensities defined on a perceived exertion scale. The scale would be 1-10 with 1 being equal to rest and 10 equating to maximum effort. The user is asked to exercise at a 2, 4, 6,(maybe 8) and to press a button to designate achieving each of the intensities, which is converted then back to a speed/power or a heart rate depending on the user's hardware platform. All intensities in between and above test values are determined by a modified regression line.

Heart Rate Calibration System—The user exercises and their heart rate data is collected each time they exercise and generated into a histogram. The histogram records the number of incidences of a heart rate within a specific range (e.g. 170-175). Each range forms an 'incidence bin' that contains a count of all heart rate data that falls between the bins range. Some ranges will be empty with no data and therefore inactive. Of the remaining active incidence bins the highest change in incidences of a heart rate falling into the highest 3 histogram range bins that are activated denotes the 'Anaerobic Threshold' heart rate zone. The system can do this assessment as a calibration workout or can do this for every workout and constantly update itself.

Power Calibration System—The user exercises and their power data is collected each time they exercise and generated into a histogram. The histogram records the number of incidences of power within a specific range. Each range forms an 'incidence bin' that contains a count of all power data that falls between the bins range. Some ranges will be empty with no data and therefore inactive. The highest change in incidences of a power falling into 'histogram bins' in the top 3 histogram bins that are activated denotes the 'Anaerobic Threshold' power zone. The system can do this assessment as a calibration workout or can do this for every workout and constantly update itself. Once again AT power is not the same for everyone, it is highly individualized. This can be at a power of 240 watts for one individual or 120 watts for another for example. In each case the training zones can be extrapolated through algorithms for each intensity level.

Speed Calibration System—the same system is applied as above to speed with several minor modifications (e.g. speeds are only assessed on the flat) to achieve the same goal.

The same concept may be applied to respiration rate (and some heart rate derivatives, cadence or turnover and distance per turnover)

Once the AT zone has been identified, in each case all the other activity/training zones can be extrapolated through algorithms for each intensity level.

If the AT is assessed for every workout so that it constantly updates which is the preferred embodiment, there are contingencies set for accepting new data that updates the historic AT zone and therefore all other activity zones. Data that falls outside being less than 90% of the maximum historic AT value or more than 105% of the maximum historic AT value is deleted and not used to update the historic AT value which is an average of accepted historic AT values for each workout.

The AT zone may be set too low with some individuals upon initial use but adapts to higher levels as the user becomes fitter and engages in more intense training.

Effort/intensity can therefore be defined as a heart rate zone, speed zone or power zone.

It is also possible to use the older method based on a real or theoretical maximum, a lactate or Conconi test, ventilation test.

3.5 Classified Activity Definitions

Table 1 (in the 'Classification Tables' section at the end of this specification) shows an exemplary classification system for a weight loss—walking/running category (or the general activities under the activity status monitoring category). The 'classification of activity type' column shows a list of the activities classified under walking/running. The 'primary intensity measurement system' column shows the secondary effort parameters that may be used in addition to resistance (which is a measure of terrain in this case). The 'metrics used' column shows the various metrics that are used to provide a measure of the monitored parameter (some or all of the metrics may be used depending on the circumstances). The 'algorithm' column specifies the thresholds criteria that are tested when utilising the classification system to identify the activity. The definition of each activity lies within the algorithm. The 'measurement sensor(s)' column outlines various sensors that may be used to provide a measure of the required parameter in the required metrics. The 'collected data over the identified activity period column' shows a list of other parameters that may be monitored upon identification of that particular activity. These other parameters would be taken into consideration when processing the activity data for interpretation of the compliance and providing advice/guidance in general.

3.5.1 Weight Loss/Activity Status Monitoring—General

Inactive

Speeds that are below 2 km/hr or 0 km/hr indicate very little movement. Power outputs that are below 25 watts or 0 watts indicate little activity. An accelerometer detecting stride rates of less than 10 strides per minute (that may have low time uniformity between steps) also indicate low activity.

Inactive Upright

A period of inactivity may be determined when a user shows very low levels of movement. The parameters that may be used to classify this are either: a multi axis accelerometer output, a multi axis accelerometer output and a speed measure, or a multi axis accelerometer output and a heart rate measure. For examples speeds that are below 2 km/hr or 0 km/hr indicate very little movement. Power outputs that are below 25 watts or 0 watts indicate little activity. Stride rates of less than 10 strides per minute (that may have low time uniformity between steps) also indicate low activity. Finally a multi axis accelerometer can also pick up if the user is lying down or standing upright if the accelerometer is mounted correctly.

Inactive Rest

Inactive Rest is the same as Inactive Upright except that a multi axis accelerometer has determined that a user is below an 80° angle to being upright for more than 1 min. Additional parameters may be used to define this classification such as heart rate (less than 40% of the user's AT heart rate, and/or less than 37% of the user's maximum heart rate) or respiration rate (of less than 12 breaths per minute for example). An average over time may be built up and used as the true thresholds.

In the preferred embodiment the heart rate and respiration rate can be assessed for all incidences so that it constantly updates the historic threshold criteria. There are contingencies set for accepting new data that updates the historic Inactive Rest zone. Data that falls outside being less than 90% of the minimum historic Inactive Rest value or more than 105% of the minimum historic Inactive Rest value is deleted and not used to update the historic Inactive Rest value which is an average of accepted historic Inactive Rest values for each 'Rest' incidence.

Inactive Prone

A single parameter which determines whether someone is prone may be insufficient to distinguish between someone lying down (prone) and someone crawling (which would be evident from an additional speed parameter for example) for instance.

Inactive prone is exactly the same as Inactive Rest but it must exceed either the set thresholds for Inactive Rest (heart rate must exceed 40% of AT heart rate or exceed 37% of maximum heart rate and respiration rate must exceed 12 breaths per minute) or it must exceed the averages for Historic Inactive Rest.

For all inactive classifications, the system may in addition gather any combination of the following data: Elapsed time, time, location, distance, altitude, gradient or slope, steps, gait analysis (including heaviness of footfall—higher force accelerometer data or limping—high contrasts in force measured through an accelerometer for right leg footfall versus left) power, heart rate, R-R interval (or Heart Rate Variability (HRV)) Electrocardiogram (ECG), blood pressure, pulse oxymetry, body temperature, glucose and cholesterol levels are also monitored to be processed as part of the data relating to the inactivity. Other data may also be included such as environmental temperature, humidity, heat index and wind chill, water temperature, wind speeds, weather conditions (rain, snow, fine) and forecast, gas (nitrogen, oxygen etc) concentrations in the air, direction a user is facing, moving backwards or forwards or laterally, location of other users (including information on their activities), location of resources, location of an object or incident, goal targets and mission objectives which may be determined through portable sensors or accessed from another source.

Upon identification of Inactivity the system may output an appropriate signal such as "Inactive Upright Identifie", "Inactive Rest Identified" or "Inactive Prone Identified", in text, auditory or graphical manner or any combination thereof. Within the streams of data recorded during the activity the data now classified under inactive upright, inactive rest or inactive prone is available for immediate processing (and therefore 'real time' feedback) or kept later for post workout analysis.

Walking Exercise

In the example shown walking is classified into the following activities: easy walking, rolling hills, hills, long climb and fat burning zone.

Easy Walking

This activity is identified when the user of the system is (or has been in the case of post exercise analysis) walking at a nominal pace on a substantially flat terrain. It is therefore preferable to monitor the state of the terrain as the first parameter to be able to identify this activity. The effort parameter as stated above and as shown in the 'primary intensity measurement system' column may be speed, heart rate or power or any combination thereof. Speed can be provided as a direct measurement (e.g. km/hr) and/or provided as a measure of stride rate (e.g. step s/minute) where indirect measures of speed such as algorithms that use accelerometers can calculate speed. Terrain can be provided as a measure of the slope and/or the gradient or change in altitude (i.e. a grade in percentage).

The algorithm specifies one or more thresholds criteria that would be tested when utilising the classification system to identify an easy walking activity.

The threshold criteria for an easy walking activity may be set using the values determined during calibration. For instance, a speed or heart rate equivalent to 3-4 on the User rating system may be the threshold criteria set for easy walking. Alternatively or in addition a heart rate of less than 55% of maximum heart rate or less than 60% of AT heart rate, and/or a speed of less than 45% of AT speed and/or power of less than 45% of AT power may be set to identify an easy walking activity.

In addition or alternative to the above threshold criteria, a stride rate threshold that defines an easy walking speed may be set by the algorithm as less than 66 steps per minute. A step in this case is considered as one full cycle of both left and right leg steps (this is however not intended to be limiting and other ways of representing the stride rate may be used).

The algorithm may also define when to stop classifying the exercise data as an easy walking activity. This may be when the stride rate exceeds 66 steps a minute for a specific length of time and/or as shown in the Table 1, when the slope exceeds 2 degrees for, for example over 6 meters of vertical gain, and/or the slope exceeds 2 degrees for, for example a 30 second period or longer.

Furthermore the algorithm may define an edge forgiveness period. This is a short period where exercise data that is being processed and compared against the thresholds drops out of the threshold zone for that activity and then returns within the threshold zone. For example, if the stride rate of the user changes to above 60 steps per minute but returns to less than 60 steps per minute shortly after, then the data gathered for the period where the stride rate was above the threshold should still be considered as part of the easy walking activity and processed with the rest of the data. In preferred embodiments the edge forgives period may be 1-9 seconds. If the stride rate (or speed, heart rate, or power) exceeds the threshold for longer than 9 seconds then the data will no longer be considered as part of the easy walking activity (and another activity may be identified by the algorithms of the classification system at this point).

The types of sensors that may be used to measure speed can be found in GPS or Accelerometer devices. An accelerometer can be used to measure stride rate or algorithms can be applied to accelerometer data to calculate speed. A GPS device, barometer, DEM (digital elevation model) device or inclinometer may be used to measure the change in terrain/altitude. If a GPS device is used then the GPS speed may need smoothing and/or the GPS altitude may require error correction.

Alternatively or in addition to speed, a heart rate parameter may be monitored and used to identify an easy walking activity. The parameter may be measured in beats per minute. The classification system would in this case be built to cater for such a parameter and set appropriate thresholds to define easy walking (as for speed).

A heart rate monitor of some sort would be used as the measurement sensor (less than 60% AT heart rate and greater than 40%, less than 55% of maximum heart rate and greater than 37%) in this case and similar additional data would ideally be collected to aid in interpretation of the activity and guidance. Note that in this case the terrain parameter is still monitored and applicable thresholds are still considered within the algorithm as described for speed above.

In yet another alternative a power parameter may be monitored as the measure for effort. The metrics used would be Watts. Easy walking equates to a power output of less than 45% of AT power (but greater than 25 watts)

Power may be taken directly from a power sensor or can be indirectly determined through an algorithm based on a speed, body weight and slope measure and similar additional data would ideally be collected as for speed and heart rate to aid in interpretation of the activity as shown in the Table 1.

Having three types of primary intensity measure (Speed, Heart Rate and Power) enables compatibility of the system with GPS (that only measures speed, no Heart Rate) or a Heart Rate monitor (no speed), for example.

Flat can be defined as an upward slope of less than 2° (4% gradient where consistent altitude (allowing for Edge Forgiveness) cannot amount to more than a 6 meter altitude gain. A downward slope of as much as −2° (−4% gradient) may be allowed.

For easy walking (and any other suitable activity defined in this specification), the classification may be further broken down into determining whether the user is moving forwards or backwards (which may also include lateral movement) using a digital compass contained in a device that is fixed to the body. This is accomplished by the system knowing the direction the user is facing and then inferring from the movement whether they are moving forwards, backwards or laterally. For instance, movements in a direction in the range of 315 to 45 degrees in relation to where the user is facing may be classified as forward movements, backwards movement may be in the direction of 135 to 225 degrees in relation to where the user is facing, movement to the left may be in the range 225 to 315 degrees and movement to the right may be 45 to 135 degrees.)

Within the streams of data recorded during the activity or exercise the data now categorised as 'easy walking' is available for immediate processing (and therefore 'real time' feedback) or kept later for post workout analysis.

Upon identification of an easy walking activity the system may output an 'easy walking identified' signal in text, auditory or graphical manner or any combination thereof.

Rolling Hills

A rolling hill is defined as a climb of more than 4 meters (when using a or GPS Digital Elevation Model the definition is above 7 meters (due to greater errors in both GPS and DEM) and less than a climb of 20 meters. Speed or Stride rate thresholds can also be applied to the classification system to determine whether the user is walking or running up the hill. Stride rates that are less than 66 strides per minute and speeds that are less than 7 km/hr would denote walking. This activity is identified when the user of the system is (or has been in the case of post exercise analysis) walking up a short hill. It is therefore preferable to monitor the state of the terrain as the first parameter to be able to identify this activity. The effort parameter may be speed, heart rate or power or any combination thereof as in the 'easy walking' activity. The metrics, algorithm thresholds and measurement sensors for the effort parameters are the same as those described for easy walking above.

Terrain can be provided as a measure of the meters ascended, slope and/or the gradient (i.e. a grade in percentage). Meters ascended may be determined using a barometer calibrated for determining change in air pressure to show change in altitude. Slope can be determined as a change in altitude over time which may be converted to slope or gradient. Slope/gradient can also be determined by an inclinometer (mounted of a bicycle handlebar) or by setting a gradient on a device such as a indoor running/walking treadmill. The algorithm associated with this activity defines a rolling hill activity as one where the slope is more than 2 degrees (or 4% gradient) and less than 8 degrees (or 15% gradient). Furthermore this is preferably the case over at least a 7 meter vertical gain but no more than a 20 meter vertical gain. In one embodiment, additionally a period threshold can be set, where a slope of more than 2 degrees is maintained for a period of more than 70 seconds but less than 200 seconds, to help define this activity. If the measured parameters were to fall outside of these thresholds then this suggests the user is no longer walking up the short hill (or is walking up a longer hill).

An edge forgiveness period of for example 1-9 seconds as described for easy walking above may be applied by the rolling hills algorithm.

Upon identification of a rolling hills activity the system may output a 'rolling hill identified' signal in text, auditory or graphical manner or any combination thereof. Within the streams of data recorded during the activity or exercise the data now classified as a 'rolling hill' is available for immediate processing (and therefore 'real time' feedback) or kept later for post workout analysis.

Hills

This activity is identified when the user of the system is (or has been) walking up a medium length hill. A hill may be defined as an increase in elevation of more than 20 meters but less than 30 meters (allowing for edge forgiveness in the preferred embodiment) Therefore the activity is defined in essentially the same way as rolling hills above, except the period threshold is replaced with a slope of more than 2 degrees being maintained for at least 200 seconds but no more than 410 seconds. Also the meters ascended differ but the same procedure is employed.

Stride rate or speed may be used in some embodiments to ensure the user is walking up the hill, with stride rates below 66 strides per minute and speeds below 7 km/hr indicating walking as opposed to running.

Upon identification of an easy walking activity the system may output a 'hill identified' signal in text, auditory or graphical manner or any combination thereof. Within the streams of data recorded during the activity or exercise the data now classified as a 'hill' is available for immediate processing (and therefore 'real time' feedback) or kept later for post workout analysis.

Long Climb

This activity is identified when the user of the system is (or has been) walking or running up a long hill. Therefore the activity is defined in essentially the same way as rolling hills and hills above, except the period threshold is replaced with a slope of more than 2 degrees being maintained for at least 410 seconds. A long climb is also defined is an increase in altitude of more than 30 continuous meters (allowing for edge forgiveness).

The same stride rate or speed system can be used to determine whether the user is walking or not.

Upon identification of a long climb the system may output a 'long climb identified' signal in text, auditory or graphical manner or any combination thereof. Within the streams of data recorded during the activity or exercise the data now classified as a 'long climb' is available for immediate processing (and therefore 'real time' feedback) or kept later for post workout analysis.

Fat Burning Zone/Fast Walking

This activity is identified when the user of the system is (or has been) walking at a fast pace. It is essentially the same as the easy walking activity except the algorithm thresholds associated with speed, heart rate and power are different. In the fast walking activity the speed threshold may be 45-60% of AT speed as it is for power.

The heart rate threshold may be 60-70% of the Anaerobic Threshold heart rate calculated in the Heart Rate Calibration system previously mentioned or 55-65% of maximum heart rate. Fast walking may be defined as the speed or heart rate equivalent of 5 to 6 on the User rating system The slope threshold that defines a fast walking terrain is set by the algorithm as less than two degrees or less than 4% gradient (which is approximately 2 degrees). Flat is defined as an upward slope of less than 2° (4% gradient where consistent altitude (allowing for Edge Forgiveness) cannot amount to more than a 6 meter altitude gain. A downward slope of as much as −2° (−4% gradient) is allowed.

Upon identification of a fast walking activity the system may output a 'fat burning zone identified' signal in text, auditory or graphical manner or any combination thereof. Within the streams of data recorded during the activity or exercise the data now classified as a 'fast walking' is available for immediate processing (and therefore 'real time' feedback) or kept later for post workout analysis.

The direction that the user is moving in; forwards, backwards or laterally can be determined by the system if the user has a digital compass fixed to their body as explained in Easy walking.

Low Speed—Run

This activity is defined when the user of the system is (or has been) running at a low speed. It is principally the same as fast walking and easy walking in that it occurs on the flat. To determine flat, the slope threshold that defines Low Speed Running terrain may be set by the algorithm as less than two degrees or less than 4% gradient (which is approximately 2 degrees) with no continuous ascent of more than 6 meters vertical altitude gain. A downward slope of as much as −8.5° (−16% gradient) may also be regarded as a low speed running activity as would any uphill that fails to qualify as a hill (less than a 6 meter climb).

The difference is primarily based on the fact that the speed is faster. This can be determined using any one or more of the three primary intensity measurements—speed, heart rate and power.

The speed threshold/zone may be 60-90% of the Anaerobic threshold speed calculated through the Speed Calibration system previously mentioned.

The heart rate threshold may be 70-80% of the Anaerobic Threshold heart rate calculated in the Heart Rate Calibration system previously mentioned (65-75% of Heart rate maximum)

The power threshold may be 60-90% of Anaerobic Threshold power calculated using the Power Calibration system previously mentioned.

Alternatively or in addition, low Speed Running may be defined as the speed or heart rate equivalent of 6.5 to 7.5 on the User rating system Stride rate may also be used particularly for defining low speed running when heart rate is the primary intensity measure. The stride rate threshold may be greater than 66 steps (as defined by a complete left right footfall cycle) per minute to indicate that the user it not walking or standing still.

The direction that the user is moving in; forwards, backwards or laterally can be determined if the user has a digital compass fixed to their body as explained in Easy walking.

Upon identification of a low speed running activity the system may output a 'low speed running identified' signal in text, auditory or graphical manner or any combination thereof. Within the streams of data recorded during the activity or exercise the data now classified as a 'low speed running' is available for immediate processing (and therefore 'real time' feedback) or kept later for post workout analysis.

High Speed Run

High Speed Running may be the same as low speed running except the threshold zones change for speed, heart rate and power.

The speed threshold/zone may be 90-95% of the Anaerobic threshold speed calculated through the Speed Calibration system previously mentioned.

The heart rate threshold may be 80-90% of the Anaerobic Threshold heart rate calculated in the Heart Rate Calibration system previously mentioned (75-85% of maximum heart rate).

The power threshold may be 90-95% of Anaerobic Threshold power calculated using the Power Calibration system previously mentioned.

Additionally or alternatively, High Speed Running may be defined as the speed or heart rate equivalent of 7.5 to 8.5 on the User rating system.

High speed running may output a 'high speed running identified' signal in text, auditory or graphical manner or any combination thereof. Within the streams of data recorded during the activity or exercise the data now classified as a 'high speed running' is available for immediate processing (and therefore 'real time' feedback) or kept later for post workout analysis.

Out of Zone: Too Fast

Any speed, heart rate or power recorded on the flat that exceeds the high speed running criteria is regarded and classified as 'Out of Zone, Too Fast' and may output an 'Out of Zone, Too Fast' signal in text, auditory or graphical manner or any combination thereof. Within the streams of data recorded during the activity or exercise the data now categorised as a 'Out of Zone, Too Fast' is available for immediate processing (and therefore 'real time' feedback) or kept later for post workout analysis.

The parameters (mainly effort and terrain in this case) that are used to determine the above classified activities aid the system in defining the activities. They provide a way of separating out the data within the activity session. This data may include many data streams of which only two in this case (terrain and effort data streams) are required to classify the data. More data streams may be captured during the activity period and a combination or all of these data streams may be then used in processing once the activity is determined and for creating 'feedback' to the user.

Non Specific Movement

Non specific movement assesses situations where the user is neither walking nor running and not stationary. The parameters assessed by the system to determine the classification are: effort (heart rate), postural status and stride rate. Speed and power are secondary measures.

Non Specific Movement—Moderate Activity

Heart rate may be greater than 45% but less than 55% of AT heart rate (greater than 37% but less than 60% of maximum heart rate).

Speed may be greater than 2 km/hr but less than 6 km/hr and movements/impacts/stride rate may be less than 40 strides per minute with poor time uniformity.

The user should be upright as assessed by a multi axis accelerometer.

Non Specific Movement—High Activity

Non Specific Movement—High Activity is the same as the Non Specific Movement—Moderate Activity classification except the intensity is higher.

Heart rate may be greater than 55% but less than 70% of AT heart rate (greater than 55% but less than 65% of maximum heart rate). Impacts/movements/stride rate is 40-60.

Non Specific Movement—Very High Activity

Non Specific Movement—Very High Activity is the same as the Non Specific Movement—Moderate Activity classification except the intensity is higher.

Heart rate may be greater than 70% of AT heart rate (greater than 65% of maximum heart rate). Speed may be greater than 2 km/hr but less than 6 km/hr and movements/impacts/stride rate may be greater than 60 strides per minute with poor time uniformity.

It is preferred that for any of the above activities, in addition to effort and terrain data, other data such as elapsed time, time, location, distance, altitude, gradient or slope, steps, gait analysis (including heaviness of footfall—higher force accelerometer data or limping—high contrasts in force measured through an accelerometer for right leg footfall versus left.) power, heart rate, R-R (or HRV) ECG, blood pressure, pulse oxymetry, body temperature, glucose and cholesterol levels are also monitored to be processed as part of the data relating to the classified activity. Other data may also be included such as environmental temperature, humidity, heat index and wind chill, water temperature, wind speeds, weather conditions (rain, snow, fine) and forecast, gas (nitrogen, oxygen etc) concentrations in the air, locations of other users (including information about their activities), location of resources, location of an object or incident, goal targets or mission objectives, direction the user is facing or moving (backwards, forwards, lateral) which may be determined through portable sensors or accessed from another source. This aids in interpretation of the compliance level of the activity for example with a preset plan and in providing future guidance/advice in general.

Note that the above defined activities are the same for both activity status monitoring and weight loss categories.

3.5.2 Activity Status Monitoring—Specialised

Table 2 shows an exemplary classification system for an activity status monitoring category (the general activities being the same as those defined under weight loss and as shown in Table 1). Activity status monitoring may be used for specialised Military, Police, Fire or Rescue services etc applications. The following is definitions of the specialised activities under activity status monitoring (general activities being defined in the previous weight loss classification section).

Sprint—Flat

A sprint is moving at a speed just above a high speed run. If a sprint is used to monitor activity then the 'Out of Zone, Too Fast' classification may not be used. Sprinting is determined by exceeding 101% of AT speed, exceeding 101% of AT heart rate or 95% of maximum heart rate and/or exceeding 105% of AT power.

Additionally or alternatively, the Sprint Running threshold may be the speed, power or heart rate equivalent of 9 to 10 on the User rating system To determine flat, the slope threshold that defines Sprint Running terrain is set by the algorithm for Flat which is defined as an upward slope of less than 2° (4% gradient where consistent altitude (preferably allowing for Edge Forgiveness) cannot amount to more than a 6 meter altitude gain). A downward slope of as much as −2° (−4% gradient) may be allowed.

Upon identification of a sprint running activity the system may output a 'sprint running identified' signal in text, auditory or graphical manner or any combination thereof. Within the streams of data recorded during the activity or exercise the data now classified as 'sprint running' is available for immediate processing (and therefore 'real time' feedback) or kept later for post workout analysis.

Sprint Hill

Sprint hills is the same as Sprint Flat except the slope must be greater than 2 degrees or 4% gradient (allowing for edge forgiveness of 9 secs).

Sprint Running may be defined as the power or heart rate equivalent of 9 to 10 on the User rating system as opposed to speed due to going uphill.

Upon identification of a sprint hill activity the system may output a 'sprint hill identified' signal in text, auditory or graphical manner or any combination thereof. Within the streams of data recorded during the activity or exercise the data now classified as 'sprint hill is available for immediate processing (and therefore 'real time' feedback) or kept later for post workout analysis.

Crawling

Crawling is the same as Inactive Prone in that sensors indicate that the users torso is prone but a smoothed speed (over 15 secs for example) greater than 2 km/hr and/or a power greater than 25 watts is required to indicate that the user is moving.

If movement detected is combined with 'prone' accelerometer data, this may indicate that a solider is crawling for example.

The direction that the user is moving in; forwards, backwards or laterally can be determined if the user has a digital compass fixed to their body as explained in Easy walking.

Upon identification of a crawling activity the system may output a 'Crawling identified' signal in text, auditory or graphical manner or any combination thereof. Within the streams of data recorded during the activity or exercise the data now classified as 'crawling' is available for immediate processing (and therefore 'real time' feedback) or kept later for post workout analysis.

Climbing

Climbing is the same as Inactive Prone but smoothed speed is less than 3 km/hr and vertical meters ascended must exceed 2 vertical meters with a gradient of greater than 15% or 8 degrees.

Upon identification of a climbing activity the system may output a 'Climbing identified' signal in text, auditory or graphical manner or any combination thereof. Within the streams of data recorded during the activity or exercise the data now classified as 'climbing' is available for immediate processing (and therefore 'real time' feedback) or kept later for post workout analysis.

Descent

Descent is exactly the same as Climbing but vertical meters descended must exceed 2 vertical meters with a gradient of greater than 15% or 8 degrees.

Upon identification of a descent activity the system may output a 'Descent identified' signal in text, auditory or graphical manner or any combination thereof. Within the streams of data recorded during the activity or exercise the data now classified as 'descent' is available for immediate processing (and therefore 'real time' feedback) or kept later for post workout analysis.

It is preferred that for any of the above specialised activities, in addition to effort and altitude/terrain data, other data such as elapsed time, time, location, distance, altitude, gradient or slope, steps, gait analysis (including heaviness of footfall—higher force accelerometer data or limping—high contrasts in force measured through an accelerometer for right leg footfall versus left.) power, heart rate, R-R (or HRV) ECG, blood pressure, pulse oxymetry, body temperature, glucose and cholesterol levels are also monitored to be processed as part of the data relating to the classified activity. Other data may also be included such as environmental temperature, humidity, heat index and wind chill, water temperature, wind speeds, weather conditions (rain, snow, fine), gas (nitrogen, oxygen etc) concentrations in the air, locations of other users (including information about their activities), location of resources, location of an object or incident, goal targets or mission objectives, direction the user is facing or moving (backwards, forwards, lateral) which may be determined through portable sensors or accessed from another source. This aids in interpretation of the compliance level of the activity for example with a preset plan and in providing future guidance/advice in general.

There are many other possible permutations for training types and by stating the following this does not mean that these are the only possible activities within activity status monitoring that can be classified.

3.5.3 Running Classification System

Table 3 shows an exemplary classification system for a running category as defined below. To be able to analyse an individual's activity in running, terrain is a requirement in the preferred embodiment. If the runner is running slowly, this could be due to fatigue or due to the fact that they are running up a hill, without terrain it is difficult to effectively analyse the situation. Therefore, for the preferred embodiment the system uses terrain as a primary parameter in classifying all types of running.

In each case when the classifications defined below are identified, including effort and terrain data, other data such as elapsed time, time, location, distance, altitude, gradient or slope, steps gait analysis (including heaviness of footfall—higher force accelerometer data or limping—high contrasts in force measured through an accelerometer for right leg footfall versus left.), heart rate, R-R (or HRV) ECG, blood pressure, body temperature, glucose and cholesterol levels are also monitored to be processed as part of the data relating to the classified activity. Other data may also be included such as environmental temperature, humidity, wind speeds, weather conditions (rain, snow, fine) heat index and wind chill, pulse oxymetry, gas (nitrogen, oxygen etc) concentrations in the air, which may be determined through portable sensors or accessed from another source. This aids in interpretation of the compliance level of the activity for example with a preset plan and in providing future guidance/advice in general.

Upon identification of a classified activity the system may output a identification signal in text, auditory or graphical manner or any combination thereof. Within the streams of data recorded during the activity or exercise the data now classified and is available for immediate processing (and therefore 'real time' feedback) or kept later for post workout analysis.

Each of the following classifications may include stride rate as a $3^{rd}$ parameter for classification. In each case stride rate should be above 66 strides per minute to ensure the user is actually running (especially where heart rate is used as the primary measure).

Inactive

Inactive is exactly the same as Inactive Upright in the Weight Loss/Activity Status Monitoring Section (3.5.1).

Easy

Easy has a similar definition as Low Speed Running in the Weight Loss/Activity Status Monitoring Section (3.5.1). All data collected when descending (altitude is decreasing or slope/gradient is negative) in a workout is collected as easy and so is all data that is uphill but fails to become classified as a form of hill. Descending could form a separate classification.

Rolling Hills

Hill training in general improves the strength endurance of a runner. Rolling Hills has exactly the same definition as Rolling Hills for Walking except in this case the user is running. It is also possible that Rolling Hills Walking and Rolling Hills Running both be used in the Running Classification system with rolling hills walking being under 7 km/hr (or the power calculation for the same speed based on a person's weight and the slope of the hill).

Hills

Hills are exactly the same as Hills under walking in the Weight Loss/Activity Status Monitoring Section (3.5.1). Except in the running configuration the user would be running. As with Rolling Hills above there could be delineation between walking and running hills in this embodiment using the same thresholds as Rolling Hills.

Long Climb

Long climbs have the same definition as for long climbs in the Activity Status Monitoring section except the user is running. Once again there might be a walking and running classification for long climbs using the same thresholds as in rolling hills above.

Hill Efforts

Hill efforts are designed to improve the power of a runner, i.e. their strength at a particular speed. Hill Efforts are very much like Rolling Hills with two exceptions, the slope of the hill required is specific and as is the speed. The hill should have a slope of between 2 and 4° (4-7% gradient). The intensity level should be 80-90% of AT heart rate, 75-85% of maximum heart rate, 90-95% of AT speed and/or 95-105% AT power. Hill Effort running is the speed, power or heart rate equivalent of 7.5 to 8.5 on the User rating system. Hill Efforts may deviate in intensity from this basic premise depending on the training requirements.

Up Tempo

The effort/speed associated with this activity simulates half marathon race pace and is used to help adapt runners to the speed. Up Tempo is exactly the same as High Speed Running in the Activity Status Monitoring section except the intensity is modified. The intensity is the equivalent of 90 to 95% of AT speed and power or 80 to 90% of AT heart rate which equates to 75 to 85% of maximum heart rate. The User rating calibration would provide speeds or heart rates equivalent of 7.5 to 8.5 out of 10 (with 10 being maximum effort).

Anaerobic Threshold

Anaerobic Threshold is very similar to 10 km race pace and is slightly higher than Up Tempo in that the speed should be between 95 to 105% of AT speed or AT power and/or heart rate should be between 99 and 101% of AT heart rate which translates roughly to 85 to 95% of Maximum Heart Rate. Anaerobic Threshold Running is the speed, power or heart rate equivalent of 9 on the User rating system (speeds, heart rates or power are therefore calculated between 8.5 and 9.5 to form a zone).

To determine flat, the slope threshold that defines Low Speed, Up Tempo, and Anaerobic Threshold Running, sprint and race pace terrain is set by the algorithm as less than two degrees or less than 4% gradient (which is approximately 2 degrees). The upward slope cannot amount to more than a continuous 6 meter altitude gain. A downward slope of as much as −2° (−4% gradient) is allowed Sprint Sprinting is used to prepare the runner for surges, starts or sprint finishes when racing and is classified in the same way as Sprint Flat in the Activity Status Monitoring section.

Overspeed

Overspeed is a training task used to improve the leg speed and fluidity of a runner's gait. The key in this case is that the runner is running slightly downhill to gain more speed which drives their leg turnover up increasing stride rate.

The slope can be less than −2 degrees (−4% gradient) but no less than −4 degrees (−7% gradient). In the preferred embodiment stride rate (measured through a pedometer) would be the same as that of 5% higher than AT stride rate. Speed should be 100-105% of AT speed or the power equivalent talking into account speed, body weight and slope. Heart Rate is not used for this classification.

Race Pace

Race Pace may vary in relation to the event the user is racing in.

Bonus Speed

In extra effort that is not planned for a workout but accidently or deliberately done (whether this is recorded in terms of heart rate, speed or power) is collected as bonus or out of zone speed.

For example a runner may meet a friend and have quite a competitive workout which includes speedwork that was not planned. In the preferred embodiment, out of zone data is collected specific to the classification that it matches but if it is not planned in the exercise session it is classed as bonus data.

There are many other possible permutations for training types and by stating the following this does not mean that these are the only possible activities within running that can be classified.

Furthermore, the running classification can also be used for cross country skiing or skating or with the absence of rolling hills, hills, long climbs and hill efforts for ice skating.

3.5.4 Cycling Classification System

Table 4 shows an exemplary classification system for a cycling category as defined below. Cycling like running preferably requires knowledge of the terrain that the user is on during each part of the workout.

Cycling in the preferred system is broken down into the following classifications; Easy, Rolling Hills, Hills, Long Climbs, Hill Spinning, Hill Efforts, Flat Big Gear, Big Gear Time Trial, Up Tempo, Anaerobic Threshold, Power, Sprint and Overspeed.

There are many other possible permutations for training types and by stating the following this does not mean that these are the only possible activities within cycling that can be classified.

Heart rate and power are preferred for determining intensity as speed is more susceptible to environmental conditions.

Other derivatives of exercise not mentioned in the following body of text may also be used to determine alternative classifications to those mentioned.

In each case when the classifications defined below are identified, including effort and terrain data, other data such as elapsed time, time, location, distance, altitude, gradient or slope, poor technique and pedalling technique analysis (including variations in the fluidity of the pedal stroke —variable force data within a pedal stroke or strength imbalances—high contrasts in force for right leg versus left, VERTICAL, tangential, radial forces.), power, heart rate, R-R (or HRV) ECG, blood pressure, body temperature, glucose and cholesterol levels are also monitored to be processed as part of the data relating to the classified activity. Other data may also be included such as environmental temperature, humidity, heat index, wind chill, wind speeds, weather conditions (rain, snow, fine) heat index and wind chill, pulse oxymetry, gas (nitrogen, oxygen etc) concentrations in the air, which may be determined through portable sensors or accessed from another source. This aids in interpretation of the compliance level of the activity for example with a preset plan and in providing future guidance/ advice in general.

Upon identification of a classified activity the system may output a identification signal in text, auditory or graphical manner or any combination thereof. Within the streams of data recorded during the activity or exercise the data now classified and is available for immediate processing (and therefore 'real time' feedback) or kept later for post workout analysis.

Inactive

Inactive is classified if the cycle speed is under 2 km/hr for more than 15 seconds and/or when power is below 25 watts for the same period. Heart rate would be below 60% of AT heart rate (below 70% of maximum heart rate.)

Easy

'Easy' can be defined by intensity (speed, heart rate or power) and terrain, or by intensity, terrain and cadence (pedal revolutions or turnover). 'Easy' uses the same percentage heart rates and speeds as used in easy running.

To be classified as 'Easy' the cyclist must be riding on the flat which as previously defined is a slope threshold set by the algorithm of less than two degrees or less than 4% gradient (which is approximately 2 degrees). It is also defined as no more than a continuous increase of 6 meters vertical ascent climbing (preferably allowing for edge forgiveness). A downward slope of as much as −8.5° (−16% gradient) is allowed as would any uphill that fails to qualify as a hill (less than a 6 meter climb).

As with easy running all descending down hills are also classed as easy as is any uphill riding that does not fall into one of the hill climbing classifications (Rolling hills, hills, long climb, hill spinning and hill efforts).

So to be classified as Easy the cyclist must be at a speed of 65-90% of AT speed, or a heart rate of 70 to 80% of AT heart rate (65-75% of maximum heart rate) or 65-90% of AT power or any combination thereof.

In the preferred embodiment cadence is included as a classification parameter, and is preferably 90 to 105 revolutions per minute for a road cyclist, 85 to 95 pedal revolutions each minute for Time trialling, triathlon and mountain biking and 80 to 95 pedal revolutions per minute for recreational 'fitness' cyclists.

For example, a road cyclist riding on a 1 degree slope that has not ascended continuously and vertically for more than 6 meters at a heart rate of 80% of AT heart rate and at a cadence of 95 pedal revolutions per minute is classified as doing Easy exercise.

Rolling Hills

Rolling Hills may be established in exactly the same way as it is for running Rolling Hills.

Hills

Hills may also be classified in exactly the same way as running Hills.

Long Climbs

Long climbs may also be classified in the same way as running Long Climbs.

Hill Spinning

Hill Spinning is the same as hills and hills long climb in that the vertical meters ascended for a hill need to be above 20 meters but each hill ascended also requires an average cadence above 70 pedal revolutions per minute during the climb.

Hill Efforts

Hill efforts are very similar to hill efforts in running in that the gradient is shallow. The hill needs to have a slope of between 2 and 4° (4-7% gradient) and an intensity of 80-90% of AT heart rate, 75-85% of maximum heart rate, 90-95% of AT speed or 95-105% AT power or any combination thereof is required. Hill Effort Running is the speed, power or heart rate equivalent of 7.5 to 8.5 on the User rating system. Hill Efforts may deviate in intensity from this basic premise depending on the training requirements.

Flat Big Gear

Flat big gear is where a cyclist trains in a big gear to improve strength endurance on flat terrain. The flat terrain definition is preferably the same as has been used throughout this document. To determine flat, the slope threshold that defines Flat Big Gear terrain is set by the algorithm as less than two degrees or less than 4% gradient (which is approximately 2 degrees) with no continuous ascent of more than 6 meters vertical altitude gain. A downward slope of as much as −2° (−4% gradient) is allowed.

The gear size needs to be determined to make sure the gearing is correct. This can be achieved by measuring which gear the user is in directly or indirectly by using distance travelled per pedal revolution or a combination of an intensity parameter (heart rate, power or speed) and a leg turnover parameter which in this case would be pedal cadence.

There are preferably two methods for determining this classified activity:

1. In the first embodiment, intensity (heart rate, power or speed) and cadence is used. An Easy intensity on the flat but a low pedal cadence indicates that the user is in a big gear. Therefore the intensity for the Flat Big Gear is Easy which equates to 70-80% of AT heart rate (65 to 75% of maximum heart rate) and 65 to 90% of AT power (65-90% of AT speed). The cadence in all cases is 65 to 75 pedal revolutions per minute.

2. In the second embodiment intensity (heart rate, power or speed), pedal cadence and distance travelled per pedal turnover are used. The intensity is the same as described above as is the pedal cadence. Distance per Turnover needs to be established based on a Distance per Turnover calibration method which is exactly the same as power and heart rate calibration methods giving a Flat Big Gear Distance per Turnover of 85 to 130% of AT turnover.

Big Gear Time Trial

A Big Gear Time Trial is very similar to Flat Big Gear and is used to train the cyclist's strength and speed following on from Flat Big Gear training. Big Gear Time Trials are carried out on the flat and at a pedal cadence of 65 to 75 pedal revolutions per minute. The fundamental difference between Flat Big Gear and Big Gear Time Trials is the intensity in Big Gear Time Trials are slightly higher. Once again there are preferably two methods of classifying this activity:
1. In one embodiment, the intensity for Big Gear Time Trials is 80 to 90% of AT heart rate (75 to 85% of maximum heart rate) and 90 to 120% of AT power. (90 to 105% of AT speed.) with a cadence of 65 to 75 pedal revolutions per minute.
2. In a second embodiment, the method uses intensity and cadence as mentioned above and includes distance per turnover of 100 to 130% of AT Distance per Turnover.

Up Tempo

Up Tempo is exactly the same as Up Tempo running from an intensity point of view and is conducted on the flat. The only addition may be pedal cadence which would preferably be at 90 to 105 revolutions per minute for a road cyclist, 85 to 95 pedal revolutions each minute for Time trialling, triathlon and mountain biking and 80 to 95 pedal revolutions per minute for recreational 'fitness' cyclists.

Anaerobic Threshold

Anaerobic threshold is the same as Anaerobic Threshold for running in that it is on the flat at the same calculated intensities. Once again cadence may be a third parameter where the pedal turnover is preferably 90 to 105 revolutions per minute for a road cyclist, 85 to 95 pedal revolutions each minute for Time trialling, triathlon and mountain biking and 80 to 95 pedal revolutions per minute for recreational 'fitness' cyclists.

Power

Power is a form of sprint cycling used to train the cyclist for low speed 'jumps' to shake a competitor off their wheel or to out sprint them in a finish where several riders have escaped the field and there are 'cat and mouse' tactics near the finish line. Power is defined as an intensity of greater than 133% of AT power and a cadence of 70 to 95 pedal revolutions per minute on the flat. It can also be defined as a speed change from 20 km/hr to AT speed in under 20 seconds at a cadence of 70 to 95 pedal revolutions per minute, or defined by a heart rate change of more than 15% of AT heart rate in 20 seconds at a cadence of 70 to 95 pedal revolutions per minute, both being on the flat. Flat is defined as an upward slope of less than 2° (4% gradient where consistent altitude (allowing for Edge Forgiveness) cannot amount to more than a continuous 6 meter altitude gain. A downward slope of as much as −2° (−4% gradient) is allowed.

Sprint

Sprinting is the same as power except the starting speed is higher and the cadence is also higher. It is also performed on the flat. Sprinting is designed to train a cyclist for a final sprint in a cycle race where the rider is at maximum effort sprinting for the line. Sprinting can be defined as an intensity where the power is greater than 133% of AT power at a cadence of 95-110 pedal revolutions per minute and can also be defined as a speed greater than 106% of AT speed at a cadence of 95 to 110 pedal revolutions per minute on flat terrain. It can also be defined as a heart rate of greater than 101% of AT heart rate (95% of maximum heart rate) at a pedal cadence of 95 to 110 revs per minute on flat terrain. Flat is defined as an upward slope of less than 2° (4% gradient where consistent altitude (allowing for Edge Forgiveness) cannot amount to more than a continuous 6 meter altitude gain. A downward slope of as much as −2° (−4% gradient) is allowed. Cadence may vary from the above depending on the user; for example are creational user cadence is generally 80-95 rpm and triathlete or mountain biker cadence is generally 85-95 rpm.

Overspeed

Overspeed is designed to improve leg speed which boosts the fluidity of a cyclists pedalling technique and also gives them a greater 'power band' from a cadence point of view when riding. Overspeed is primarily described by pedal cadence and terrain. The pedal cadence must exceed 111 pedal revolutions per minute and the terrain must be flat or slightly downhill. This is defined as a slope of less than 0° (0% gradient where consistent altitude and a downward slope of as much as −4° (−6% gradient) is allowed. Power, heart rate and speed are not primary parameters for this activity.

Bonus Speed

In extra effort that is not planned for a workout but accidently or deliberately done whether this is recorded in terms of heart rate, speed or power is collected as bonus or out of zone speed. For example a cyclist may meet a friend and have quite a competitive workout which includes speed-work that was not planned. Out of zone data is collected specific to the classification that it matches but if it is not planned in the exercise session it is classed as bonus data.

Race Pace

Race Pace varys in relation to the event the user is racing in.

3.5.5 Rowing and Kayaking

Table 5 shows an exemplary classification system for a rowing/kayaking category as defined below. Rowing and kayaking are grouped together because the main component of speed for both sports is the distance per stroke in the water multiplied by the stroke rate.

In this case terrain is not a factor, so stroke rate is substituted as the resistance component. Usually a combination of intensity and stroke rate will describe distance per stroke relatively reliably. Alternatively distance per stroke could be used but this is harder to measure for use as it is affected by moving water whether this is water flowing down a river or tides and currents.

Rowing and Kayaking have the following classifications: Inactive, Easy, Slow Full Pressure, Tempo Load, Up Tempo, Anaerobic Threshold, Starts and Moves and Out Of Zone.

Other derivatives of exercise not mentioned in the following body of text may also be used to determine alternative classifications to those mentioned.

In each case when the classifications defined below are identified, including effort and stroke rate data, other data such as elapsed time, time, location, distance, altitude, gradient or slope, poor technique (including variations in the fluidity of the pedal stroke—variable force data within a stroke or strength imbalances—high contrasts in leg drive force for right leg versus left, right versus left arm in sculling.), power, heart rate, R-R (or HRV) ECG, blood pressure, body temperature, glucose and cholesterol levels are also monitored to be processed as part of the data relating to the classified activity. Other data may also be included such as environmental temperature, water temperature, humidity, heat index, wind chill, wind speeds, weather conditions (rain, snow, fine) heat index and wind chill, pulse oxymetry, gas (nitrogen, oxygen etc) concentrations in the air, which may be determined through portable sensors or accessed from another source. This aids in interpretation of the compliance level of the activity for example with a preset plan and in providing future guidance/advice in general.

Upon identification of a classified activity the system may output a identification signal in text, auditory or graphical manner or any combination thereof. Within the streams of data recorded during the activity or exercise the data now classified and is available for immediate processing (and therefore 'real time' feedback) or kept later for post workout analysis.

There are many other possible permutations for training types and by stating the following this does not mean that these are the only possible activities within rowing or kayak training that can be classified.

Inactive

Inactive is classified if the rowing/kayaking speed is under 2 km/hr for more than 15 seconds or when power is below 25 watts for the same. Heart rate would be below 45% of AT heart rate (below 45% of maximum heart rate.)

Easy

Easy is defined using a combination of intensity and stroke rate. The intensity is 70 to 80% of AT heart rate, (65 to 75% of maximum heart rate), and/or 65 to 90% of AT power or speed. The stroke rate is 18 to 22 strokes per minute (stroke rate can vary depending on the skiff being rowed—e.g. an 8 will tend to have slightly higher stroke rates than a pair for example). This is 6 to 7.5 in a user rating scale.

Slow Full Pressure

Slow Full Pressure is a type of strength endurance training which involves high muscular load with relatively low cardiovascular load. Slow Full Pressure is classified as 70 to 80% of AT heart rate (65 to 75% of maximum heart rate) at a speed or power of 80 to 93% of AT speed or power respectively. The stroke rate is 18 to 22 strokes per minute. 7 to 8 on the user rating scale.

Tempo Load

Tempo Load is designed to promote power or fast strength and is a slightly more intense version of Slow Full Pressure where the intensity is slightly increased. This has a intensity of 80 to 90% of AT heart rate (75 to 85% of maximum heart rate) for a power or speed of 90 to 93% of AT speed and 90-103% AT power. Stroke rate is 18 to 22 strokes per minute (but can be set slightly higher initially) and the user rating scale would be 7.5 to 8.5.

Up Tempo

Up Tempo is the transitional training from strength endurance training to speed and is similar to Tempo Load but uses a higher stroke rate. Up Tempo is the same as other Up Tempo classifications already stated in this document in that it is 80 to 90% of AT heart rate (75 to 85% of maximum heart rate) and/or 90 to 93% of AT power or speed. Stroke rate conforms more closely to race pace stroke rates. The user rating is 7.5 to 8.5 and the stroke rate required is 23 to 32 strokes per minute.

Anaerobic Threshold

Anaerobic Threshold begins to condition the rower to race pace and is a slightly higher intensity being 99 to 101% of AT heart rate (85 to 95% of maximum heart rate) and/or 93 to 105% of AT power and speed. The stroke rate moves up again to 33 to 35 strokes per minute. This rating on the user scale is 8.5 to 9.5.

Race Pace

Race Pace may vary in relation to the event the user is racing in.

Starts

Starts are used to improve the 'off the line' ability in a rowing start which can be quite crucial. This is where a rower moves from stationary to anaerobic threshold pace. So the definition of a start is from no speed or power (or very little, less than 2 km/hr) to 95 to 105% of AT speed or power or from Easy heart rate of less than 75% of AT heart rate (less than 65% of maximum heart rate) to AT heart rate being (99 to 101% of AT heart rate (85 to 95% of maximum heart rate). Stroke rate moves from zero to race pace stroke rate of preferably greater than 34 strokes per minute. The user rating is 9 or greater.

Moves

Moves are brief short bursts of race pace or slightly higher efforts. The intensity is usually greater than 101% of AT heart rate (95% of maximum heart rate) and greater than 105% of AT power or speed. The stroke rate is preferably greater than 34 strokes per minute. The user rating is 9 or greater.

Bonus Speed

Any extra effort that is not planned for a workout but accidently or deliberately done whether this is recorded in terms of heart rate, speed or power is collected as bonus or out of zone speed.

For example a rower may meet someone else out on the water and race them, resulting in quite a competitive workout which includes speedwork that was not planned. Out of zone data is collected specific to the classification that it matches but if it is not planned in the activity session it is classed as bonus data.

3.5.6 Field Sports

Table 6 shows an exemplary classification system for a field sports category as defined below. Field sports are usually about ability to get into position and the ability to out accelerate your opponents therefore understanding and therefore classifying field position and speed for a field sports is useful.

Field and larger court sports break down into 0 to 5 meter speed, 5 to 10 meter speed, 10 to 20 meter speed, 20 to 40 meter speed and finally 40+ meter speed all of which can be analysed from a more or less stationary start or moving start. There are several non sprinting classifications which include tempo speed, jogging speed, walking, stationary and jumping. This information can be measured versus location.

Figure 11A:
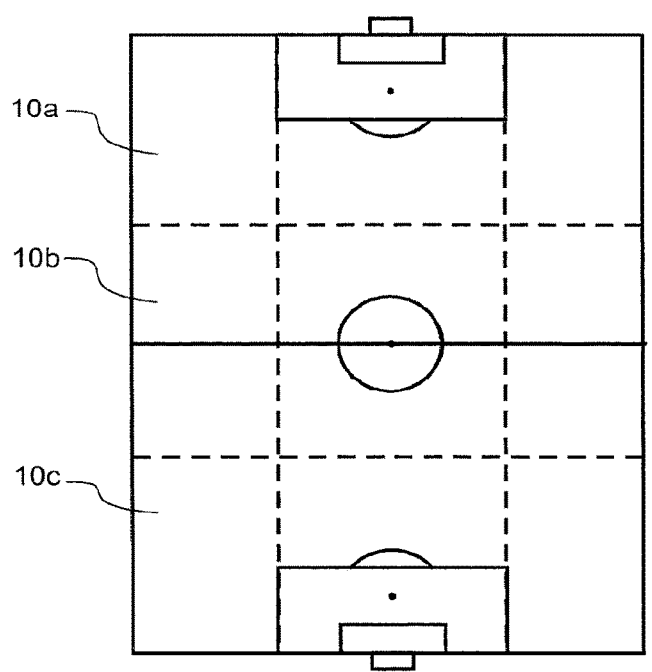
FIGS. 11a-c show schematics of a football field partitioned into different number/sized quadrants for the purposes of field sport classification.
Figure 11C:
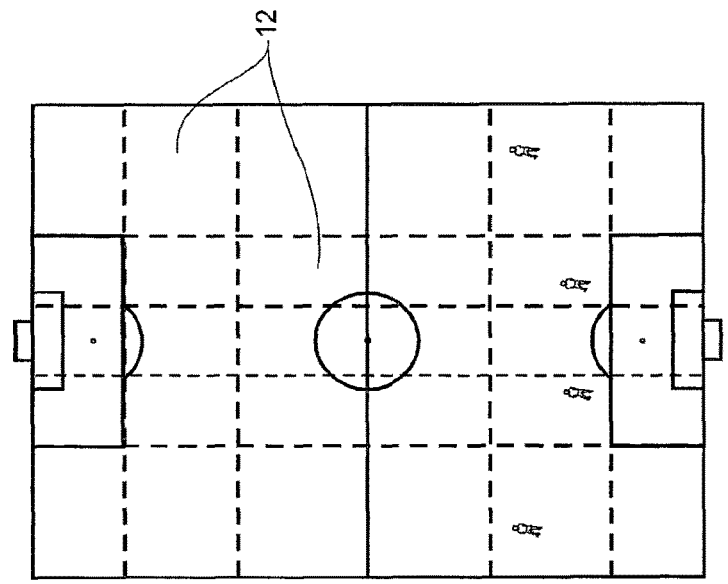
Figure 11B:
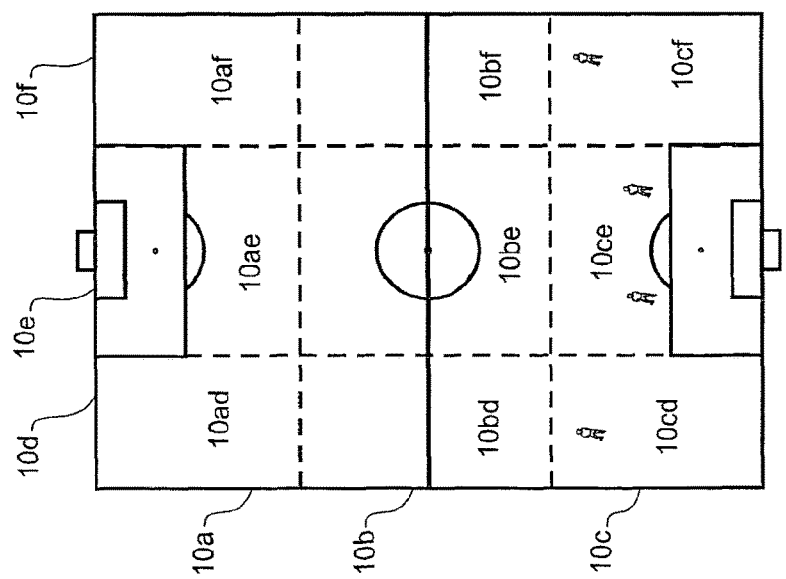

Location:

It is useful to know where on a competition field each activity took place. Referring to FIGS. 18a-c, a field can be broken up into preselected zones to measure activity within. Activities like sprints, jogging, standing, tackles and going to ground are logged in relation to a specific area within the playing field. For example a soccer field can be divided into thirds laterally (FIG. 11a), being an attacking third 10a, midfield third 10b and defensive third 10c. There may also be an 18 yard (depth of the penalty box) area. This can also be further segregated into longitudinal locations being centre field 10e, left 10d and right flanks 10f creating a series of 9 quadrants (FIG. 11b). This can be further broken up into tighter quadrants 12 for more intense analysis (FIG. 11c). The number of quadrants (zones) is dependent on the application and the above examples are not intended to be limiting. The shape of the zones can also be altered if desired.

Parameters:

The following parameters are used to classify data within a game or practice.

Speed and Power are the primary intensity parameters with power inferred from speed and body weight being the preferred embodiment. The secondary measure is location (in zones or quadrants). Other measures include altitude to determine whether the player is upright, lying on the ground or jumping. Another parameter is an ability to determine whether a player is upright or 'on the ground' using a multi axis accelerometer. Stride rate is also a preferred secondary measure in some classified activities.

Field sports involve a multi parameter classification in the following way. Speed or power (or possibly heart rate) is combined with one or many of the following including stride rate, direction the user is facing, location on the field, elapsed time in the game, impacts, upright versus prone, and/or altitude.

In one embodiment, speed is obtained through accelerometer, GPS, transmitter to transceiver/receiver triangulation (similar to indoor location systems) or video motion capture. Stride rate is obtained from the combined time and impacts measured through an accelerometer. The direction the user is facing is obtained through a digital compass. Location can be obtained by GPS, transmitter to transceiver/receiver triangulation or video motion capture systems. Altitude for measurement of jumping and 'going to ground' is obtained by barometer or better still by transmitter to transceiver/receiver triangulation. Tackles are measured in G's using an accelerometer. 'Going to ground' or lying down can also be measured with a multi axis accelerometer fixed to a player.

In each case when the classifications defined below are identified, other data such as elapsed time, time, location, distance, altitude, poor technique (including variations in left and right leg stride—including right leg versus left strength imbalances, running technique issues, foot contact time, stride length, stride rate, force of foot), power, heart rate, R-R (or HRV) ECG, upright/prone, impacts, body temperature may also be monitored to be processed as part of the data relating to the classified activity. Other data may also be included such as environmental temperature, humidity, heat index, wind chill, wind speeds, weather conditions (rain, snow, fine) heat index and wind chill, pulse oxymetry, location of other users, location of the ball or puck, which may be determined through portable sensors or accessed from another source. This aids in interpretation of the performance level of the activity and in providing future guidance/advice.

Upon identification of a classified activity the system may output an identification signal in text, auditory or graphical manner or any combination thereof. Within the streams of data recorded during the activity or exercise the data is now categorised and is available for immediate processing (and therefore 'real time' feedback) or kept later for post workout analysis.

These segments of different activity types within a game/practice with all the data streams captured within the segment allows for much easier and more intense analysis of a players physiological profile and requirements.

20 meter 'flying start' sprint segments for an inside back (first 5/8's in Rugby Union) can be analysed versus a benchmark profile of an international 'champion' player as an ideal. Data such as stride rate and stride length may determine that the reason the player is having difficulty accelerating is that they are over striding in the few strides versus the benchmark profile. It may be determined that a player has international champion level aerobic (jog/running) ability and good extended sprints (20-40 meters) but lacks shorter sprinting ability (5-15 meters) which would diagnose that the player needed to work on their shorter sprints training or that the coach would reassign the player to a position more suited to their physiology.

All the following multi parameter classifications combine speed/power with time and/or location. Some will include direction the user is facing, stride rate, upright/prone, impacts, and altitude. Each classification uses a distance that the data is captured in. Location can be defined as the attacking third of the field, midfield and defensive third of the field but can be further divided into left flank, right flank and centre field as shown in FIG. 11b. This creates 9 quadrants where data can be classified being: attacking left flank 10ad, attacking right flank 10af, attacking centerfield 10ae, let flank midfield 10bd, centre midfield 10be and right flank midfield 10bf and defensive left flank 10cd, defensive right flank 10cf and defensive centerfield 10ce. Further areas include penalty box, centre left and centre right both being classifications within centre field or goal left flank, goal right flank.

'Game' as referred to in the classifications below is intended to mean data that is taken from a game or multiple games of rugby, soccer, hockey etc (i.e. competition data).

Stationary—Upright

Stationary is the same as Inactive Upright and is classified if the speed is under 2 km/hr for more than 15 seconds or when power is below 25 watts for the same. Location can be attacking left flank, attacking right flank, attacking centerfield, let flank midfield, centre midfield and right flank midfield and defensive left flank, defensive right flank and defensive centerfield. Upright can be determined by a multi axis accelerometer attached to the player or an altitude measure (ideally transmitter to transceiver/receiver triangulation). Stride rate should be less than 10 steps per minute.

Stationary—Prone

Stationary prone is used to determine if a player is on the ground with an injury or after a tackle for example. Stationary Prone utilises the same system as used in Inactive Prone in the Activity Status monitoring section where the user must be in a prone position for 0.5 secs or more. Location can be determined in the same way as 'Stationary Upright'. Prone is determined by a multi axis accelerometer attached to the player or an altitude measure (preferably via transmitter to transceiver/receiver triangulation).

0 to 5 Meter Power/Speed Moving 0 to 5 Meter Power/Speed is defined as being greater than 95% of the highest historic game speed average over a distance of 5 or less meters. An initial speed of greater than 40% of highest current game or historic speed for at least 10 seconds is also required. The percentages used have the flexibility to be adjusted by a coach or trainer or speed/effort zones can be used instead. Location can be attacking left flank, attacking right flank, attacking centerfield, let flank midfield, centre midfield and right flank midfield and defensive left flank, defensive right flank and defensive centerfield.

0 to 5 Meter Power/Speed Stationary

This is exactly the same as 0 to 5 Meter Power/Speed moving except that the data is only captured if the power or speed is less than 40% of highest game historic power or speed average for at least 10 seconds immediately before the sprint. The percentages can be adjusted.

Location can be attacking left flank, attacking right flank, attacking centerfield, let flank midfield, centre midfield and right flank midfield and defensive left flank, defensive right flank and defensive centerfield. If Stride rate is used it is preferably to be less than 70 strides per minute immediately before the sprint as well.

5 to 10 Meter Power/Speed Moving

This is defined as being greater than 90% highest game historic average power or speed for 5 to 10 meters. An initial power/speed of greater than 40% of highest current game or historic power or speed for at least 10 seconds is also required. The percentages can be adjusted.

Location can be determined in the same way as '0 to 5 Meter Power/Speed Stationary'

Stride rate is preferably higher than 70 strides per minute.

5 to 10 Meter Power/Speed Stationary

Data is captured only if power/speed is greater than 90% highest game historic power or speed average for 5 to 10 meters and the initial power or speed immediately before the sprint is greater than 40% of highest current game or historic power or speed for at least 10 seconds. The percentages used have the flexibility to be adjusted by a coach or trainer or speed/effort zones can be used instead. Location can be attacking left flank, attacking right flank, attacking centerfield, let flank midfield, centre midfield and right flank midfield and defensive left flank, defensive right flank and defensive centerfield. If Stride rate is used it is preferably less than 70 strides per minute immediately before the sprint as well.

10 to 20 Meter Power/Speed Moving

This is the same as the 5 to 10 Meter Speed Moving description except that the power or speed is defined as greater than 85% highest game historic average power or speed for 10 to 20 meters. An initial power/speed of greater than 40% of highest current game or historic power or speed for at least 10 seconds is also required. The percentages used have the flexibility to be adjusted by a coach or trainer or speed/effort zones can be used instead.

Location can be attacking left flank, attacking right flank, attacking centerfield, let flank midfield, centre midfield and right flank midfield and defensive left flank, defensive right flank and defensive centerfield. Stride rate is preferably above 70 strides per minute.

10 to 20 Meter Power/Speed Stationary 10 to 20 Meter Power/Speed Stationary Data is recorded only if power/speed is greater than 85% highest current game or historic power or speed for 10 to 20 meters and the initial power or speed immediately before the sprint is greater than 40% of highest average game historic power or speed for at least 10 seconds. the percentages can be adjusted. Location can be determined in the same way as '10 to 20 Meter Power/Speed Moving'. If stride rate it is preferably less than 70 strides per minute immediately before the sprint as well.

20 to 40 Meters Power/Speed Moving

This is the same as the other Power/Speed Moving descriptions, except the distance the sprint is measured over is longer and the intensity is slightly lower, preferably being greater than 80% of highest game historic average for power/speed. The same definition for power or speed immediately before the sprint applies. The percentages used have the flexibility to be adjusted by a coach or trainer or speed/effort zones can be used instead.

Location can be attacking left flank, attacking right flank, attacking centerfield, let flank midfield, centre midfield and right flank midfield and defensive left flank, defensive right flank and defensive centerfield.

20 to 40 Meters Power/Speed Stationary

Exactly the same as the 10 to 20 meter definition except the speed versus highest game historic power or speed average is 80%. The percentages can be adjusted by a coach or trainer.

Location can be determined in the same way as '20 to 40 Meters Power/Speed Moving'. Stride rate can also be used.

40+ Meters Power/Speed Moving:

The same as the previous Moving descriptions except over more than 40 meters at a power or speed greater than 75% of highest game historic power/speed average. The percentages used have the flexibility to be adjusted by a coach or trainer or speed/effort zones can be used instead. Location can be attacking left flank, attacking right flank, attacking centerfield, let flank midfield, centre midfield and right flank midfield and defensive left flank, defensive right flank and defensive centerfield.

40+ Meters Power/Speed Stationary:

As for 20 to 40 Meters Power/Speed Stationary except at more than 75% based on game historic speed or power average.

Location and the percentages can be determined in the same way as '40+ meters Power/Speed Moving'.

The following 4 classifications; tempo speed, jogging, slow jogging and walking all could be further broken down by the system into determining whether the user is moving forwards or backwards (which may also include lateral movement) using a digital compass contained in a device that is fixed to the body. This is accomplished by knowing the direction the user is facing and then inferring from the movement whether they are moving forwards, backwards or laterally. For instance, movements in a direction in the range of 315 to 45 degrees in relation to where the user is facing can be classified as forwards movement, backwards movement is in the direction of 135 to 225 degrees in relation to where the user is facing, movement towards the left is in the range of 225 to 315 degrees, and movement towards the right is 45 to 135 degrees.

Tempo Speed

Tempo Speed is all running that is greater than 60% of highest game historic average speed/power that is not captured by the sprint classifications. Classifications can be broken further into moving forwards (315 to 45 degrees), moving backwards (135 to 225 degrees) and lateral movement, i.e. right (45 degrees to 135 degrees) and left (225 to 315 degrees). The speed/effort percentages used have the flexibility to be adjusted by a coach or trainer or speed/effort zones can be used instead. Location can be attacking left flank, attacking right flank, attacking centerfield, let flank midfield, centre midfield and right flank midfield and defensive left flank, defensive right flank and defensive centerfield. Stride rate is preferably greater than 70 strides per minute.

Jogging

Jogging is the same as tempo speed except it is defined as less than 60% of highest game historic average speed or power but greater than 55%. The speed/effort percentages used have the flexibility to be adjusted by a coach or trainer or speed/effort zones can be used instead.

Location can be attacking left flank, attacking right flank, attacking centerfield, let flank midfield, centre midfield and right flank midfield and defensive left flank, defensive right flank and defensive centerfield.

Slow Jogging

This is the same as jogging above except it is defined as 40 to 55% of highest game historic average speed or power.

The speed/effort percentages used have the flexibility to be adjusted by a coach or trainer or speed/effort zones can be used instead.

Location can be attacking left flank, attacking right flank, attacking centerfield, let flank midfield, centre midfield and right flank midfield and defensive left flank, defensive right flank and defensive centerfield.

Walking

Walking is the same as jogging except for the following differences. It is characterised by less than 40% of highest game historic speed or power averages but greater than 2 km/hr or 25 watts for more than 15 seconds. Location can be attacking left flank, attacking right flank, attacking centerfield, let flank midfield, centre midfield and right flank midfield and defensive left flank, defensive right flank and defensive centerfield. Time can be $1^{st}$ half versus $2^{nd}$ half or narrower time periods within a game. The speed/effort percentages used have the flexibility to be adjusted by a coach or trainer or speed/effort zones can be used instead.

Stride rate is preferably below 70 strides per minute.

Jumping—Vertical

This activity is determined by a vertical altitude change by more than 30 cm and a power output increase by more than 100 watts with no stride rate. The altitude change and power in watts can be adjusted by the coach or trainer. Location can be attacking left flank, attacking right flank, attacking centerfield, let flank midfield, centre midfield and right flank midfield and defensive left flank, defensive right flank and defensive centerfield.

Jumping—Horizontal

This activity is determined by a continued horizontal movement with very little to no stride rate. Location, power and altitude can be determined in the same way as 'Jumping—Vertical'.

Sidestep

A sudden change in direction while sprinting can be determined to be a sidestep. This is where direction changes by more than 45 degrees detected by a digital compass fixed to the body of a player during a sprinting classification in less than 1.5 secs. Location can be attacking left flank, attacking right flank, attacking centerfield, let flank midfield, centre midfield and right flank midfield and defensive left flank, defensive right flank and defensive centerfield.

Tackle

A tackle is an impact measured through an accelerometer with an impact exceeding 40 Gs. The impact in G's can be adjusted by a coach or trainer. Location can be attacking left flank, attacking right flank, attacking centerfield, let flank midfield, centre midfield and right flank midfield and defensive left flank, defensive right flank and defensive centerfield.

Preferably for the purposes of determining sprinting, jumping and tackling the update rate for the activity data is 0.25 s or less. Furthermore, altitude is preferably measured by a transmitter and transceiver/receiver network in field sport applications.

3.5.7 Horse Training

Table 7 shows an exemplary classification system for a horse training category as defined below. When training horses the same problems for training occur that do in humans. It is very difficult to apply science to screeds of data on a horse without classifying each type of training. This is further exacerbated by the fact that the trainer is not actually doing the training themselves so it is harder to get an understanding on what is happening on a day to day basis through the training. Similar classifications may be applied to horse training.

In the preferred embodiment this category of classifications only requires one parameter for the purposes of automated analysis and feedback.

The classified activities of one embodiment are; Inactive, Walk, Trot, Canter, Gallop, Fast Gallop, and Sprint.

The following classification does not discount the possible use of stride rate and stride length for purposes of classification also.

Inactive—Stationary

Stationary is the very similar to Inactive Upright. It is a period of inactivity which may be determined when a horse shows very low levels of movement. For examples speeds that are below 2 km/hr or 0 km/hr indicate very little movement. In one embodiment, heart rate can be used and would be below 45% of AT heart rate (less than 37% of maximum heart rate).

Walk

A walk is classified as less than 55% of AT heart rate (less than 50% of maximum heart rate) or less than 14% of AT speed.

Trot

A trot is classified as 56-70% of AT heart rate (51 to 60% of maximum heart rate) or 14 to 33% of AT speed.

Canter

A Canter is described as 71 to 85% of AT heart rate (61 to 70% of maximum heart rate) or 33 to 65% of AT speed.

Gallop

A Gallop is 85 to 95% of AT Heart Rate (70 to 80% of maximum heart rate) or 65 to 95% of AT speed.

Fast Gallop

A Fast Gallop is described as 95 to 105% of AT speed (80 to 90% of maximum heart rate) or 65 to 105% of AT speed.

Sprint

A sprint is defined as greater than 105% of AT heart rate (greater than 90% of maximum heart rate) or greater than 105% of AT speed.

3.5.7 Pedometer Classification Embodiment

Background and Limitations:

A pedometer uses a multi axis accelerometer and counts a step by measuring an impact, like a foot strike and counts each in a cumulative fashion which has been made very popular by for example the '10,000 step programme' where the user as a health initiative must take 10,000 steps per day.

Impacts measured through an accelerometer oscillate from low force to high force and there are known algorithms that calculate the peak force in the oscillation which designates a step.

While there are many pedometers available on the market, very few can do anything more than count steps. Further, pedometers cannot tell the difference between a user tap dancing or running, driving along in a car on a bumpy road and running.

At lower intensities it can be difficult to differentiate between the above mentioned conditions. Driving on a bumpy road in a car may cause the pedometer to 'think' that the user is doing some walking or running activity even though they are sitting in a car.

Time Uniformity:

To further improve the accuracy of determining what the user is doing a time variability/uniformity measure can also be employed as a filter to determine whether the user is in the car or walking. Time between 'steps' can be measured to differentiate between steps and false movements. True walking or running can be crudely distinguished by the degree of uniformity in the impacts. The more random the impacts the more likely the user is not walking or running. By rights, walking and running lend themselves to a high degree of time uniformity between steps. Therefore random impacts such as doing the housework that does not have a continuous period of low stride rate variability can be disregarded by an algorithm as not walking or running.

The way this is achieved is that the device measures each impact and logs the time between each impact and the next. A group of timed results from measures of the times between each impact are then averaged and the greater the level of uniformity (e.g. less than 30 milliseconds between steps) is more likely to indicate that the user is walking or running. In this way a more precise estimate of the user's activity can be defined.

Very low stride rates, for example below 15 strides per minute are also an indicator that the user is not walking or running.

Using Pedometers to determine Intensity

Pedometers are also currently unable to determine the intensity at which the user is walking or running at. To determine intensity you must first determine stride rate. Stride rate can also be measured by a pedometer (although stride rate is often determined as the time between a single leg's foot strikes so 180 impacts in a minute would be referred to as a stride rate of 90 strides per minute). Stride rate and intensity are closely linked where: 55 strides per minute can be classed as walking, 75 strides per minute can be classed as easy running, 84 strides per minute can be classed as moderate running, and 90 strides a minute can be classed as running hard for most people. This means that stride rate can be used as a crude measure of cardiovascular intensity.

Multiparameter Classification

The classification is a combination of the time uniformity between steps (impacts) and the number of steps per minute taken. If the uniformity is below 30 milliseconds, the stride rate is then classified depending on the stride rate.

All walking or running should be in the preferred embodiment continuous for 30 seconds to begin being classified by the system within a stride rate zone. As with the other classifications there is edge forgiveness that allows a user to be out of zone temporarily for preferably up to 9 seconds if they were in the zone before that.

Classifications:

The preferred classifications and definitions (threshold criteria) for this particular category are as follows:

Inactive Rest
Inactive Stationary
Slow Walk
Walk
Fast Walk
Jog
Moderate Intensity Run
High Intensity Run
Non specific movement—Moderate Activity
Non specific movement—High Activity
Non specific movement—Very High Activity Table 8 shows an exemplary classification system for a pedometer category as defined below.

Inactive Rest:

Inactive rest involves 2 measures: the accelerometer must show that the user (or at least the device is horizontal) and the stride rate is close to zero. (i.e. impact uniformity is greater than 30 ms and stride rate is less than 15 strides/impacts/movements per minute.)

Inactive Stationary:

This shows that the user is upright and the stride rate is close to zero. (i.e. impact uniformity is greater than 30 ms and stride rate is less than 15 strides/impacts/movements per minute.)

Slow Walk:

The system identifies a stride variability that is 30 milliseconds or below and the stride rate is between 30-40 strides per minute.

Walk:

The system identifies a stride rate variability of 30 milliseconds or below and the stride rate is 40 to 55 strides per minute.

Fast Walk:

The system identifies a stride rate variability below 20 milliseconds and a stride rate of 56 to 66 strides per minute.

Jog:

Jogging is determined when stride rate is 67 to 75 strides per minute and stride rate variability is under 10 milliseconds.

Moderate Intensity Run:

This is determined by a stride rate that is 76 to 86 strides per minute and the variability is below 10 milliseconds.

High Intensity Run:

High Intensity Running has a stride rate of between 87 to 95 strides per minute and once again the variability is under 10 milliseconds.

Sprint:

Sprinting is classified when stride rate is 96 or above strides per minute with a variability of under 10 milliseconds Non Specific Movement—Moderate Activity Non specific movement assesses situations where the user is neither walking nor running and not stationary. Impacts/Stride rate/movements is greater than 15 but less than 40 strides or impact/acceleration peaks recorded per minute and there is poor time uniformity. (Greater than 40 ms)

The user is identified by the system upright as assessed by a multi axis accelerometer.

Non Specific Movement—High Activity

Non Specific Movement—High Activity is the same as Non Specific Movement—Moderate Activity except the number of impacts/accelerations is higher. Impacts/accelerations/Stride rate is greater than 40 but less than 60 strides or impact/acceleration peaks recorded per minute.

Non Specific Movement—Very High Activity

Non Specific Movement—Very High Activity is exactly the same as above except the impacts/Stride rate/movements is greater than 60 strides or impact peaks recorded per minute.

Other Options:

Total G force or combinations of the forces in the multi axis accelerometer may also be used as a substitute for time variability/uniformity calculations. Below 20G is an indication in most cases that the user is walking and above 20G indicates running.

The other parameter that might be added to the classification is whether the user is upright or horizontal to further strengthen the understanding of the situation.

3.6 Definitions for Sensor types:

The system is able to be configured to many different types of sensors and therefore is not bound to a specific device but rather may use many different types of devices so long as they contain the required sensors and provide the right parameters. It may occur also that the system utilizes data from sensors from several different devices as is the case with using a smart phone with internal GPS and heart rate data from a Zephyr HRM BT or the barometric, temperature, GPS and heart rate data from a FRWD B series device combined with the internal accelerometer found in a smart phone.

Each activity sensing category: Activity Status Monitoring, Weight Loss and Walking, Running, Cycling, Rowing and Kayaking, Horse Training and Pedometer Monitoring will now be covered in terms of sensors required and current devices that are available in the market that could utilize the system of the invention. The following exemplary devices are not intended to limit the scope of the invention and other devices capable of providing the correct measurements for the system algorithms may be used instead and as required by the particular application.

3.7.1 Activity Status Monitoring: (Health, Military, Fire and Rescue Services)

For Easy Walking, Rolling Hills Walking, Hills Walking, Long Climb Walking, Fast Walking, Low Speed Run, Rolling Hills Run, Hills Run, Long Climb Run, High Speed Run, Out of Zone—Too Fast the sensor requirements are the same. They all require some measure of altitude change combined with an intensity measure which can include measurements of speed, power or heart rate. This also applies for specialist 'services' classifications also contained in the Activity Status Category; Very High Speed Run, Sprint Flat, Sprint Hills.

Altitude Change:

Altitude change can be measured in many different ways through current sensor devices. These include barometers, inclinometers, Digital Elevation Models and GPS. Altitude change is a way in which a sensor can determine the terrain the user is on. For example an increase in altitude or gradient indicates that the user is moving uphill, a decrease in vertical meters or a decline means the user is going downhill and no altitude change or a flat gradient or slope means the user is on the flat.

Many devices currently contain digital barometers and thermometers. Examples of this include Suunto sports watches (e.g. Suunto X6 & T6), the Timex Altitude Barometer Adventure Tech watch, the Casio Pathfinder series of watches and Polar Heart Rate devices (e.g. RS800, CS600 etc).

There are also handheld barometers such as the Nova Lnyx 230-M202 and VWR handheld digital barometer 4198, both of which use barometric pressure to measure altitude.

Suunto and some cycle computer companies include inclinometers on their devices to measure slope/gradient change.

A digital elevation model (DEM) is a digital representation of ground surface topography or terrain. Various data sets are available of differing accuracy levels based on satellite surveys of the earth including the Shuttle Radar Topography mission in 2000. Once the coordinates of a user are known their position can be overlaid onto the topography of their location in real time or in post processing. Digital Elevation Models (sometimes know as Digital Terrain Models) are used for post processing of data by companies like Bones in Motion and Sportsdo.

Garmin uses GPS in its Forerunner 205, 305 and 405 series watches to show altitude. Garmin also have devices like the Garmin eTrex Summit HC which are handheld and contain a barometer for altitude. GPS altitude is obtained by the triangulation of satellites in the sky overhead at the time.

Intensity:

Speed

Speed can be measured a number of ways through a number of sensors from crude accelerometer algorithms like in the Zephyr HRM BT, Nike+ and the Timex Pedometer with Speed, through to more sophisticated algorithms like Dynastream use in their speed pods which are licensed to companies like Polar for their RS800, FT80 and 625 products, and like the Adidas micoach Pacer and Suunto T6.

Other devices such as Fitbit, Fitlinxx Actiped and Directlife track activity through accelerometers. Bodymedia's Fit system, Mytrak's M2 and Polar's FA20 all track movement but not necessarily speed.

GPS can also be used to obtain speed data and is used in a host of devices such as the Polar G3 GPS sensor, the Garmin Forerunner 205, 305 and 405 models as well as many apps like Runkeeper, Sportsdo and Bones in Motions Motion X app that rely on either mobile phones with internal GPS or linked to an external GPS.

With Federal Communications Commission requirement after the 9/11/01 terrorist attacks for location availability in all mobile phones in the US in the future, there will be a greater proliferation of phones with internal GPS.

There are devices like the Mobimotion Spurty chest strap that contains both a heart rate monitor and GPS that Bluetooth data to a phone and many other devices that accept and log Bluetooth data such as the FRWD W and B series.

In the case of military, fire and rescue services, the system could switch from outdoor location to indoor location detection. Crude speed measures could utilise infrared, ultrasonic, RFID, UWB and signal strength systems.

Power

Power for a walker or runner currently can only be inferred by applying a Power algorithm to the data based on speed, the user's weight and the slope or gradient at the time. It may not be too long before power will be more directly measured using force plates in shoes or by converting acceleration data in a shoe to power.

Crude power measures may be able to be inferred from the above mentioned indoor location detection systems.

Heart Rate

Heart rate can be measured directly currently through a strap that contains 2 electrodes that is placed across the chest and was originally designed by Polar Electro which filed its patent in 1979 and is the world leader in wireless chest strap heart rate monitors. The patent has now expired and many other companies use this technology including Timex, Suunto, Garmin, Cardiosport, Impulse and Zephyr.

There are now many Heart Rate Monitor straps like the Zephyr HRM BT and the Mobimotion Spurty chest strap that do not have a data receiver but rather Bluetooth data to devices like a mobile phone. Still other devices like the SMHeartLink act as a bluetooth receiver for the Apple iphone to accept heart rate data from a heart rate strap and the FWD B series devices that are able to receive broadcast heart rate data from most wireless heart rate straps and resend the data to a phone via BluetoothOther devices receive broadcast data using the ANT+ signal.

There are other methods to obtain heart rate which includes a strapless heart monitor like the Mio heart rate monitor that requires the user to place 2 fingers on the electrodes on the watch face to obtain heart rate measurement.

It is possible to obtain heart rate through infrared where light change is used to measure heart beats and also disposable electrodes as opposed to straps.

R-R (Relaxation Rate) or HRV (Heart Rate Variability) could also be used to measure intensity on the body. Heart rate variability measures the average of the time (in ms) between a series of heart beats and the more intense the effort the more uniform the time between heart beats.

FRWD, and some Suunto and Polar devices are able to measure heart rate variability.

It is conceivable that in the very near future heart rate may be able to be measured through the wrist, finger or via some other means which may include Respiration Rate. Respiration rate is calculated by measuring expansion of the chest using a chest strap as used in the Zephyr Bioharness. Another method for measuring heart rate as in the Firstbeat licensed system to Suunto and FRWD derives respiration rate and ventilation (which could also be used to measure intensity) through heart rate which increases during inhalation.

Stride Rate

Stride rate may also be used as an extra classification parameter. This involves the use of an accelerometer that records the repetitive impact for each stride which is then summed over 1 minute of time providing a measure of strides per minute. Stride rate is a handy extra measure as it can be used to determine the speed of leg movement which further contributes to building a picture of what the user is doing. A stride rate of 55 strides per minute indicates that the user is walking, 80 strides per minute is easy running, and 90 strides per minute would be fast running for example. The Polar RS800 measures and displays stride rate in real time and most smart phones contain accelerometers these days which can be used to measure stride rates on a phone by counting impacts over time.

There are 3 inactive classifications within Activity Status Monitoring; Inactive Upright, Inactive Rest and Inactive Prone. None of these use altitude change to classify the activity. But rather use speed, heart rate (or respiration rate) and an accelerometer.

Positional Status (Accelerometer)

All Inactive classifications require a positional status measurement via an accelerometer as seen in most smart phones these days which use 2 or 3 axis sensors within the accelerometer to determine whether the device is upright or prone which can in turn determine whether the user (or device at least) is vertical or horizontal so long as the device is in a fixed position on the user.

Movement (Speed)

Speed can be established using an accelerometer or GPS to determine whether the user is moving or stationary. Power can be inferred from speed.

Intensity

Intensity can be determined further if needed by heart rate, respiration rate or ventilation rate as explained in the Intensity section above.

Through this matrix a measure of very low intensity may indicate that the user is at rest and a higher intensity will indicate that the user is mildly active even if speed shows they are not moving. A horizontal positional status combined with no movement and a very low intensity indicates that the user is lying down and at rest.

There are 3 other specialist 'services' classifications; Crawling, Climbing and Descending. Crawling is simply determined by a positional multi axis accelerometer sensor that is fixed on the body (e.g. the belt on the torso) that indicates that the user is horizontal and speed via GPS or an accelerometer indicates that the user is moving slowly indicating crawling.

Climbing and Descending are shown by no or very little horizontal speed as measured by GPS and or accelerometer and a change in altitude by GPS, Barometer, DEM or inclinometer depending on whether the altitude change is purely vertical or up or down a very steep slope.

Direction that a user is facing can be determined by a digital compass like those now present in many smart phones like the iphone and new android operating system present on some smart phones. If the device is fixed to the user, direction the user is facing can be inferred.

3.7.2 Weight Loss—Walking and Running Classification

All weight loss classifications use exactly the same sensor measurement systems as Activity Status Monitoring. The devices that hold the sensors may vary though. Devices such as BodyMedia's fit system device and the Mytrak M2 are portable weight loss recreational fitness devices. The Polar FA20 activity tracker for example can also be used to determine calories burned. There are 2 wrist devices built by Adidas and Nike known as the micoach Zone and the Nike Sportband which also contain accelerometers.

Weight loss may include the use of machines that can simulate altitude change (going up or down a hill) in various mechanical ways (like using a predetermined incline) for determining gradient or slope in equipment like treadmills Treadmill manufacturers can preset inclines on their treadmills and program them to show various inclines based on an inbuilt program or through manual adjustment by the user. There are now various flash thumb drive USB plug-in devices that record training conducted on treadmills and other gym equipment.

3.7.3 Running Classification

Running has a series of classifications very similar to the Activity Status Monitoring and Weight Loss. The inactive classification is the same as the Inactive Upright classification for both previous classification systems.

The other classifications: Easy, Rolling Hills, Hills, Long Climbs, Hill Efforts, Up Tempo, Anaerobic Threshold, Sprints and Overspeed use altitude change and intensity (speed, power or heart rate) and can use stride rate as another method of determining intensity for classification of activity types.

Altitude Change

All the classifications incorporate the sensors in the same way as mentioned above in Activity Status Monitoring. Devices that contain a barometer or GPS can all determine altitude change like the Suunto and Polar Products as well as Mobimotion. A DEM can be used with any GPS compliant device like a mobile phone and altitude can be determined from GPS as in the Garmin devices.

Intensity

Speed

Devices like the Nike+, Nike Sportband, Adidas micoach Zone and Pacer, Suunto and Polar devices which contain accelerometers are designed to measure running speed. Mobimotion, FRWD and Polar G3 GPS devices and phone applications that utilize internal or external GPS for determining speed like Bones in Motion, AllsportGPS and imapmyrun are also specially designed for running.

Health Applications like Fitbit, Fitlinxx Actiped and Directlife, Bodymedia's Fit system, Mytrak's M2 and Polar's FA20 are not designed for running.

Heart Rate

The basis of Heart Rate sensor technology does not change with use in different sports and is therefore the same as Activity Status Monitoring.

Stride Rate

As above, Stride Rate can also be used as another form of intensity measure utilizing an accelerometer in a speed pod like the Polar RS800 or an accelerometer contained in a phone. Adidas measure stride rate using a waist mounted Pacer and the wrist version known as the Zone.

The Running classification 'Overspeed' requires altitude change, intensity AND stride rate for classification.

3.7.4 Field Sports

Field sports have some demand for altitude change (determining the fact that the player is jumping vertically, horizontally or is on the ground.) Very accurate understandings of speed and speed change are also vital to analysis of activity.

Field sports can use exactly the same technology as the running descriptions above with 2 extra possibilities.

Players can wear transmitters that can be triangulated on the side of the playing field by receivers that can be used to calculate speed. Sophisticated video motion capture can be used to do the same thing.

A digital compass may also be employed to measure direction the user is facing and therefore the user's movement (i.e. backwards, lateral etc).

3.7.5 Rowing and Kayaking:

Rowing and kayaking once again have no need for a measure of altitude change to ascertain resistance so stroke rate is substituted for measuring altitude change. Inactive, Easy, Slow Full Pressure, Tempo Load, Up Tempo, Anaerobic Threshold, Starts and Moves are all measured in the same way.

Stroke Rate:

Stroke rate is usually measured in rowing based on a magnet being attached to and under the rowers moving seat and a sensor is placed in the boat directly below the seat. A stroke is sensed every $2^{nd}$ time the magnet passes over the sensor. This count is then measured versus one minute which provides the ability to measure strokes per minute. Strokes per minute can be measured more directly at the rigger, by force sensors in the blade of the oar, or by the increase in boat oscillation speed, or be change in force measured by an accelerometer as the rower takes a stroke.

Similar methods can be applied to Swimming as evidenced by the Speedo Strokz Stroke Counter that was available in the late 1990's.

The seat magnet and sensor is commonplace in rowing and there is now new Surge Rate technology incorporating a 3 axis accelerometer to measure the change in force that denotes a kayaker or rower's stroke, thereby allowing stroke rate to be determined when combined with time as in Nielsen Kellerman Rowing and Kayaking devices like the Stroke Coach, Cox Box and Speed Coach.

Stroke Rate can also be mechanically measured in indoor rowing machines such as a Concept 2 rowing ergometer, by measuring a change in power or speed in the fan used for resistance, by a change in direction of the chain/cable attached to the rowing handle, or by using the magnet and sensor under the rower's seat.

It may also be possible to fix an accelerometer to a kayaker's paddle shaft to measure the oscillation in the blade entering the water on the left and right sides of the boat.

Intensity:

Speed:

Speed can be measured via GPS or an impeller to measure speed through the water. Speed can be measured for an indoor rowing ergometer by the braking pressure for braked devices or by the speed at which the fan spins at.

Impellers are used in Nielsen Kellerman products like the Stroke Coach, Cox Box and Speed Coach for rowing. The Garmin Forerunner series are often used by kayakers which utilize GPS.

Heart Rate:

Heart rate is measured by a receiver of some kind like a Polar or Garmin heart rate monitor. They can also be incorporated into a device measuring all required data like the receiver used in Concept 2 rowing ergometers taking transmitted heart rate data from a chest strap which is then incorporated into the devices measurement. The Garmin Forerunner 305 and 405 both obtain heart rate data which can be used by Kayakers.

3.7.6 Cycling: (Applies to Triathlon, Mountain Biking, Road, Track and BMX Cycling)

Cycling incorporates slightly different technology to running in that the data must be obtained from a bicycle.

The same basic concept applies as it did for running in that the user must use a combination of altitude change and intensity with an extra classification being cadence.

The following classifications require altitude change and Intensity; Easy, Rolling Hills, Hills, Long Climbs, Hill Efforts, Up Tempo, and Anaerobic Threshold.

The following classifications require altitude change, Intensity and cadence; Flat Big Gear, Big Gear Time Trial, Power, and Sprint.

Altitude Change:

Altitude change can be determined in exactly the same way as in running through a barometer, GPS, DEM or inclinometer. In this case inclination can be used very effectively when mounted on a bicycle which is perfectly level on the flat. Devices like the Sigma BC 2209 MHR and Garmin Edge 705 contain a barometer for altitude measure. The Sigma Rox 8.0 uses an inclinometer as well as a barometer to measure slope or gradient.

There are various cycle ergometers which use various systems to create the equivalent of altitude change. These can be complete bike ergometers or machines that a bike is placed into. The cycle simulator manufacturers can program their devices to increase resistance to simulate gradient or slope through mechanical braking (e.g. Monarch and Cateye CS1000) or electronic braking (e.g. Tracx and Computrainer) and can also use real incline change.

Intensity:

Speed:

Speed for cycling is achieved by attaching a magnet to a spoke on the front or rear wheel of the bike of known circumference and each time the magnet passes a sensor on the forks or rear stay on the bike the distance is added. The distance versus time gives speed. Speed can also be measured through GPS and even converted back through power or calculated from wind speed. Most bike computers use a magnet on the spokes like the Polar CS300. Indirectly it would be possible to calculate speed from knowing the gear the rider is in.

Power:

Power is usually a direct measure in cycling. Power measurement for cycling was pioneered by SRM who use strain gauges attached to the large front sprockets (chainrings) at the bottom bracket attached to the pedal cranks. PowerTap use a system originally used in the Look Max One where the power is measured in the hub of the rear wheel. Ergomo use power measured from the bottom bracket directly.

There have been several indirect measurements of power most notably being the Polar system (e.g. 625X or 725 products) which measures the strain on the chain as the cyclist is riding. Other cycle computers indirectly compute power by measuring a combination of speed, weight and slope or gradient.

An indirect way of assessing power is present in the Shimano Flight Deck and in the Australian Institute of Sport system which measures the gear that the rider is in allowing a calculation of distance per pedal stroke. In each case the gear that the rider is in, is known and the distance for each gear for a pedal turn is fixed.

Heart Rate:

Heart rate measurement is available on many cycle computers (e.g. Polar CS300, Sigma Rox 8.0, SRM).

Cadence or Distance per Pedal Stroke:

Cadence is a useful extra measure which usually involves a magnet on the pedal arm (crank) passing a sensor on the chain stay of the bike. This can indicate one pedal revolution and when used in conjunction with time creates a pedal cadence measure in revolutions per minute. Distance per pedal stroke is another very useful measure that can be calculated by knowing the gear that the rider is in (e.g. Shimano Flight Deck) or by knowing the distance travelled in a pedal revolution which involves a cadence measure and a distance measure (which is based on the speed measure).

The SRM system incorporates altitude change, speed, power, heart rate and cadence as measures for example.

3.7.7 Horse Training

Horse training is the relationship in most cases between heart rate and speed or power and terrain is used occasionally.

For Inactive, Walk, Trot, Canter, Gallop, Fast Gallop and Sprint the following combination of Speed or Power and Heart Rate applies:

Speed:

Speed for horse training is measured through GPS devices like GPS-Speed Genie GT31, the GPSsports Spi Pro or FRWD. Theoretically a speed pod may become available for horses. For trotting a magnet can be fixed to a wheel and a sensor can be fitted to the sulky to calculate speed.

Power:

Power could potentially be employed for horses but currently there is no such product.

Intensity:

Heart Rate:

Heart rate has been measured for horses for over 15 years using various Polar Equine Heart Rate monitors like the Polar Equine RS800CX G3 or the CS600X for trotting.

Stride Rate and Length would also make excellent data for classification but are as yet unavailable.

Hill Efforts combines terrain (a change in altitude as discussed previously) and speed, power or heart rate.

3.7.8 Pedometer Monitoring:

Pedometer monitoring uses a multi axis accelerometer which can be found in smart phones but may also be present in other Pedometer like devices such as the Polar FA20, the Directlife system, Fitbit, Fitlinxx Actiped, Bodymedia's Fit system and Mytrak's M2 device which all track movement.

4. Interpretation:

Uses of the Activity Classification Method

The Activity Classification Method can be used in 2 instances;

'Command and Control' and 'Automated Coaching'.

Command and Control is where activity classification provides information on activities to be assessed by an individual for example, rescue services and many team sport situations.

Automated coaching is where activity classification is combined with automated interpretation which can then be used to provide direction to a user in terms of 'coaching advice' and modification of an activity plan. Coaching Advice can occur without using a plan.

It is this second instance that we will now describe.

Coaching Advice:

The process for obtaining 'Automated Coaching' advice and Activity/Training Plan Modification is as follows:

1. Raw data and derived data from data streams within detected Training Type segments are put against a series of multiple zones simultaneously which are linked to coaching advice
2. Where a match occurs, Coaching advice and Plan Modification are generated for the criteria that was analyzed Interpretation System Flexibility; Multi Sport and Multi Sensor Each Training Type can be interpreted in terms of compliance, technique and performance. The following shows how interpretation can be used for the Running Training Types; Easy, Rolling Hills, Hills, Up Tempo and Anaerobic Threshold but these are not the exclusive areas for analysis and other measures could be used.

The interpretation also has the flexibility to be sensor agnostic. Interpretation is 'richer' or 'poorer' dependent of the data received meaning more sensors providing more data (speed, heart rate, altitude, stride rate) means more interpretation is possible and less sensors (speed and DEM only) means less interpretation is possible.

It is easy to convert the system for most acyclic sports like cycling, rowing, kayaking, mountain biking, cross country skiing, skating, and most team sports. It can also be used to determine and 'coach' in more health and activity related situations.

Raw and Derived Data Parameters

To show the scope of the invention and it's uses, we will now provide a brief description to demonstrate interpretation.

Raw and derived data for some of the possible measures will now be described:

Duration:

Duration is the number of minutes a classified Training Type segment occurs for or the accumulated time for Training Type segments of the same label. (e.g. one segment of Up Tempo might be 2 mins long or three segments of Up Tempo might add up to 5 mins and 20 seconds) (Applies to Up Tempo and Anaerobic Threshold Training Types)

Number of Repetitions Completed:

This is a count of the number of training type activity segments that have begun and stopped during an activity session. (e.g. the system may have detected the Up Tempo Training Type activity segment 5 times during the workout while the user was training so the number of repetitions (reps) completed was 5.) (Applies to Up Tempo and Anaerobic Threshold Training Types)

Number of Hills Completed:

This is a count of the number of hill segments detected and completed within a workout. Rolling Hills are detected by a continuous increase of more than 6 meters and less than 20 meters and Hills are detected as an increase of more than 20 meters as covered by the Activity Classification Method. (Applies to Rolling Hills and Hills Training Types)

Cumulative Vertical Meters Ascended:

This is a measure of the number of meters ascended over an entire workout for Rolling Hills and Hills independently. (e.g. Rolling Hills could involve 3 climbs; the first being 15 meters, the $2^{nd}$ being 15 meters and the $3^{rd}$ being 10 meters which means a cumulative vertical meters ascended for Rolling Hills of 40 meters.) (Applies to Rolling Hills and Hills Training Types)

Many other possible areas can be measured within the bounds of performance, technique and compliance.

The Anatomy of a Training/Activity Plan:

Coaching advice can occur in relation to a Training/Activity Plan or can provide more limited feedback without the user having a plan.

We will start with some definitions to provide context on how an Training Plan would work:

Training Plan

A Training Plan is a calendar of workouts or activity sessions over a series of days for an extended period of time, usually for a number of months. The plan is designed to generate the largest improvements specific to a chosen goal for the least time, effort and impact on the body. This is achieved by manipulating workouts and training types in terms of volume and timing over an extended period of time allowing the body to gradually adapt to the various physical stimuli placed on it.

Workout

A workout is an activity session on a particular day which contains a set of different types of activities called Training Types. The workout is usually for a set duration or distance.

Training Types

Training Types occur within a workout, which are training tasks to be performed within the workout/session.

Workouts contain Training Types of set durations, efforts and the number of times the activity should be repeated within a workout which are also known as repetitions. (reps)

A workout may be 60 mins in duration and contain the Training Types; Hills and Up Tempo. The repetitions might be 4 hills and 2×2 mins at Up Tempo. This means that within the 60 mins workout or activity the user has a prescription to complete 4 hills and do 4 mins of Up Tempo broken into 2 parts. Using the Activity Classification method which detects Training Types, the user can choose when it is most appropriate to complete a Training Type within a session.

Training/Activity Plan, Workout, Training Types Combination

A Training Plan is made up of a series of workouts that contain Training Types, set within a calendar over a series of months that describe the activity tasks required to achieve a goal whether this be to compete in an sporting event, lose weight or maintain health.

The interpretation can be compliance, technique or performance based.

Compliance measures are used to determine how closely a user follows their Training Plan. If the actual data closely matches the plan, compliance is high; if data does not closely match the plan, compliance is low. Compliance is made up of the number of hills completed and cumulative vertical meters ascended for Rolling Hills and Hills Training Types. Duration and reps completed are the elements that make up compliance for Up Tempo and Anaerobic Threshold. There is no compliance measure for the Easy Training Type. Compliance can only be measured against a Training Plan.

Technique measures can include measurements of how the user conducts themselves within the workout. Stride rates, heaviness of foot strike and many other components can be used to provide feedback on technique. Technique measures can occur whether the user is following a plan is not.

Performance measures are also possible where fatigue and improvement can be ascertained. Elevated heart rates for a particular speed indicate fatigue for example and there are many other methods available within the prior art (e.g. R-R, VO2max, EPOC, Training Effect, Heart Rate Decoupling) that can be used. Performance measures can occur whether or not the user follows a training plan.

Coaching Advice:

Training Types Used for Coaching Advice:

Measures of each Training Type occur separately and therefore independent analysis occurs for:

Easy
Rolling Hills
Hills
Up Tempo
Anaerobic Threshold

These Training Types have been described in the Activity Classification method.

Sample Plan for the Workout

Below is an example of a workout that is part of a Running Training Plan, where the workout duration and the number of reps/durations for all the training types are used within the workout.

| Training Types & Workout Duration | Planned |
|---|---|
| Workout Duration: | 60 mins |
| Anaerobic Threshold | 0 |
| Up Tempo | 4 reps (of 4 mins) |
| Hills | 3 hills (>20 vertical meters) |
| Rolling Hills | 0 |

The above describes a 60 min workout that has 4 periods of 4 mins of the Up tempo Training Type in it totaling 16 mins at Up Tempo and 3 hills of 20 meters making approximately 60 meters. There is no Anaerobic Threshold Speed training or Rolling Hills to be done within the workout today.

The workout therefore uses 2 Training Types; Up Tempo and Hills. The other 2 Training Types are not being used; Anaerobic Threshold and Rolling Hills.

It is against this set of tasks that the user's activity is measured.

Data that shows that the user followed the Training Plan closely shows high compliance and data that does not match the plan closely enough and/or has missing tasks or tasks completed that were not scheduled within the plan will indicate poor compliance.

The following is a table of the plan versus what was actually done in the workout:

TABLE 9

| Training Types & Workout Duration | Planned | Actual |
|---|---|---|
| Workout Duration: | 60 mins | 70 mins |
| Anaerobic Threshold (85-95% HRmax* on flat) | 0 | 0 |
| Up Tempo (75-85% HRmax* on flat) | 4 reps (of 4 mins) = 16 min | 3 reps (18 mins) |
| Hills (>20 vertical meters) | 3 hills (60 meters) | 2 hills (80 meters) |
| Rolling Hills (>6 vertical meters, <20 meters) | 0 | 0 |

*HRmax = maximum heart rate

We will now go through the analysis for each Training Type and Total Workout duration that was specified in the plan compared to what was actually performed by the user:

EXAMPLE 1

Workout Duration

The plan for the workout called for 60 mins of running. The actual exercise duration was 70 mins. The user did 10 mins more training than the program specified.

This means that the user did 116% of what they should have done for the plan. (70 mins divided by 60 mins equals 116% of the plan.)

Workout Duration Data Thresholds:
The 116% is applied against a set of thresholds
Less than 85%
85% to 95%
95% to 105%
Greater than 105%
116% fits into the 'greater than 105%' threshold.
Less than 85% "Exercise Duration was far below the plan, please follow the plan carefully"
85% to 95% "Exercise Duration was slightly below the plan, please follow the plan carefully"
95% to 105% "Exercise Duration was correct well done!"
Greater than 105% "Exercise Duration exceeded plan, please follow the plan carefully"
The coaching feedback/advice would be:
"Exercise Duration exceeded plan, please follow the plan carefully"

Timing of 'Coaching Advice'—Real Time or Post Workout:

The coaching advice for workout duration occurs immediately upon completion of the workout on a device or could be provided on a website or device for post workout feedback. A real time comment could occur however, if the workout duration is exceeded. In the example, when the users workout duration exceeds 5% greater than the prescribed workout duration of 60 mins which is 63 mins a real time comment can be given "Prescribed workout duration exceeded."

EXAMPLE 2

Up Tempo Training Type

The workout plan was for 4 repetitions of 4 mins making a total of 16 mins of the Training Type; Up Tempo.

Up Tempo is a Training Type that occurs at about 75-85% of effort. (as defined by the calibration system within the Activity Classification method). This is above the Easy Training Type of 65-75% of effort. During a workout the runner spends most of their time at Easy but may decide to increase their effort to 75-85% of maximum to do the Up Tempo Training Type.

Up Tempo is determined by a heart rate or speed training zone which must occur on flat terrain as per the classification description. 75-85% of maximum might equate to a heart rate of 175-185 bpm or a speed of 12.5-13.5 km/hr as calibrated by the Activity Classification method. (both heart rate and speed parameters might be combined to define effort).

The runner therefore moves their effort up and heart rate reaches 175 bpm on the flat. The classification system identifies that the user has now moved into the Up Tempo Training Types zones (on the flat) and will begin to log recorded data that occurs as an Up Tempo Training Type segment.

For the next 4 mins the runner focuses on keeping their heart rate within the training zone of 175 to 185 bpm on the flat. After 4 mins the user slows down again and their heart rate drops below 175 bpm which means that it has fallen out of the Up Tempo Training Type and back into the Easy Training Type. At this point the system discontinues logging the Up Tempo Training Type. Therefore the logged duration of the Up Tempo Training Type segment is 4 mins.

In this case the user logged Up Tempo 3 times as opposed to the 4 repetitions that were planned within the workout. There were correct and incorrect rep durations of 4 mins, 11 mins and 3 mins making a total of 18 mins.

Up Tempo Compliance Utilizes 2 Measurement Areas:
Up Tempo Duration
And repetitions completed Up Tempo Duration Data Calculation:

The planned workout duration for Up Tempo was 16 mins and 18 mins was completed during the workout. (see Table 9)

18 mins divided by 16 mins equals 112% meaning that 12% more Up Tempo Duration training occurred than was planned.

Up Tempo Duration Data Thresholds

| | (=>, <) | takes most significant comment (i.e. compliance: <-1.5% or >1%, performance: <-2% or >0.2%, if 2 significant comments split (hi/lo, lo/lo, hi/hi) = most % biggest change |
|---|---|---|
| 1 | <-2% | Part of going fast is getting used to the speed. Up Tempo is used to aid you in acquiring speed endurance. Look at the duration targets in the plan more carefully. |
| 2 | (-2% to -1%) | You can't get faster without speed and Up Tempo is a good low impact way to do this. Use the training program for guidelines on how much you should do. |
| 3 | (-1% to 1%) | Good work! |
| 4 | 1% to 5% | Too much speedwork is a bad thing. Apart from increasing chance of injury, it causes high fatigue, upsets your energy for other workouts and can predispose you to illness. |

The correct coaching advice for 12% more for Up Tempo Duration training done than scheduled is 4 (see table above):

"Too much speedwork is a bad thing, apart from increasing chance of injury, it causes high fatigue, upsets your energy for other workouts and can predispose you to illness."

Up Tempo Repetitions Completed Data Calculation:

The plan was for 4 repetitions of 4 mins at Up Tempo (see FIG. 1) and the actual training carried out training was 3 repetitions of 4 mins, 11 mins and 3 mins.

4 repetitions were supposed to be completed and only 3 were completed.

3÷4=75% meaning 25% less (-25%) Up Tempo Repetitions completed occurred than planned. Up Tempo Repetitions Completed Data Thresholds:

| 1 | <-2 | You need to progressively increase the number of reps of a training type that you do to get improvement. The training program will guide you on this |
|---|---|---|
| 2 | (-2 to -1%) | To get faster there has to be some increase in the number of reps run for this training type within a workout. |
| 3 | (-1-1%) | Nice work, keep moving the number reps of Up Tempo run up gradually over time. |
| 4 | 1% to 5% | If you didn't plan to do extra Up Tempo, you might be pushing it a little hard as you seem to be jumping up into Up Tempo too often. |

The correct coaching advice for −25% Up Tempo Reps Completed is 1 (see table above):

"You need to progressively increase the number of reps of a training type that you do to get an improvement. The training program will guide you on this."

Timing of 'Coaching Advice'—Real Time or Post Workout:

Coaching feedback can occur in real time if the user exceeds the total duration of Up Tempo scheduled in the plan. The following advice would be given: "Too much Up Tempo speedwork, this can overtrain you or cause injury. Discontinue Up Tempo training." This would occur immediately after the planned Up Tempo duration is exceeded by more than 5%. For 16 mins of the planned Up tempo, a 5% increase is 16.8 mins or 16 mins 48 secs. If the duration for a particular rep is exceeded by more than 10% which for a 4 mins repetition is 4.4 mins or 4 mins 24 secs, the commentary is "Planned Rep duration exceeded, slow down" and if the planned duration matches within + or −10% (e.g 4 mins+/−24 secs) the real time comment is "Excellent, your rep duration was correct". If the rep duration is less than −10% (e.g. 3 mins 36 secs) the comment is: "Rep Duration too short"

After the completion of each repetition, a data summary is provided which includes the duration of the repetition. For example at the end of the repetition of Up Tempo the commentary is: "$1^{st}$, $2^{nd}$, etc Up Tempo Rep Completed Xmins"

EXAMPLE 3

Hills Training Type

The workout plan was for 3 Hills. (meaning a minimum of 60 vertical meters ascended). Hills are measured if the continuous ascent for a user travelling faster than 7 km/hr exceeds 20 meters of continuous climbing. 3 Hills means a minimum of 60 vertical meters ascended. The user runs to the hill and after 6 meters of vertical ascent a hill is detected, when the user exceeds 20 meters the Training Type is classed as Hills Training Type and is logged as such until the user reaches the top at say 27 meters. When the user reaches the top and the terrain plateaus, the system detects that the user has stopped climbing.

At this point the system discontinues logging the Hills Training Type.

Therefore, the logged vertical meters ascended is in this case 27 meters for a Hills Training Type segment.

The user incorrectly logged 2 hills totaling 80 vertical meters of climbing, 1 of 27 meters and the other of 53 meters. (see Table 9)

Hills Compliance Utilizes 2 Measurement Areas:
  Number of Hills Completed
  And Cumulative Vertical Meters Ascended
  Number of Hills Completed Data Calculation:
  The planned number of Hills was 3 and only 2 Hills were completed. (See FIG. 1)
  2÷3=66% or 34% less (−34%) Hills than planned.
  Number of Hills Completed Data Thresholds:

| | takes most significant comment (i.e. compliance: <−1.5% or >1%, performance: <−2% or >0.2%, if 2 significant comments split (hi/lo, lo/lo, hi/hi) = most % biggest change |
|---|---|
| (=>, <) | |
| 1 <−2% | Without a steady increase in your hillwork, you don't get the stiumlus that drives your strength endurance up. Increase the number of hills you do gradually each session. |
| 2 (−2% to −1%) | To get stronger you need more load and in this case that means slightly more hills each time you do a hills session. |
| 3 (−1% to 1%) | Great Work! |
| 4 >1% | Overdoing your training is not beneficial, it is more likely to lead to injury, illness or fatigue! Follow the training plan more closely please. |

The correct coaching advice for −34% less Hills completed than scheduled is 1 (see table above): "Without a steady increase in your hill work you don't get the stimulus that drives your strength endurance up. Increase the number of hills you are doing gradually each session."

Cumulative Vertical Meters Ascended Data Calculation:

The plan was for approximately 60 vertical meters of climbing to be done and 80 vertical meters was climbed. (See Table 9)

80÷60=133% meaning 33% more meters climbed than planned.

Cumulative Vertical Meters Ascended Data Thresholds:

| 1 <−2 | To get an improvement in your strength endurance you need more load and in this case it means slightly more climbed vertical meters each time you do a hills session. |
|---|---|
| 2 (−2 to −1%) | Getting stronger strength endurance wise is not made without some increase in the volume of meters climbed in training. |
| 3 (−1-1%) | Nice work, keep building on the number of vertical meters ascended you do gradually over time. |
| 4 >1% | Doing more climbing than is in the training plan is counter productive, you are far more likely to disrupt the balance of the program, get fatigued or worse injured. Follow the plan. |

The correct coaching advice for 33% more vertical meters climbed than was planned for Hills is 4 (see table above):

"Doing more climbing than is in the training plan is counterproductive, you are far more likely to disrupt the balance of the program, get fatigued or worse, get injured. Follow the plan."

Timing of 'Coaching Advice'—Real Time or Post Workout:

Coaching feedback can occur in 'real time' if the user exceeds the vertical meters of the Hills vertical meters scheduled in the plan by 20% or more (60×120%=72 meters). The following advice would be given: "Too much Hill work, this can overtrain you or cause injury. Discontinue Hill Training" This would occur immediately after 72 meters was exceeded.

At the completion of each Hill a data summary is provided which includes the vertical meters climbed and the number of Hills climbed to that point. For example at the completion of the $1^{st}$ Hill of 27 meters the commentary is: "$1^{st}$ Hill completed, 27 meters, Cumulative Vertical Meters: 27 meters."

EXAMPLE 4

Easy Training Type

All training that is not Up Tempo, Anaerobic Threshold, Rolling Hills or Hills is classed as Easy Training Type. As the user goes through a workout they will complete other Training Types. In this case the user did 3 repetitions of 4 mins, 11 mins and 3 mins of Up Tempo and 2 Hills totaling 80 meters. In between each of these Training Types the user was still running although more gently in the Easy Training Type. Therefore multiple segments of the Easy Training Type were produced in this workout. If we include a warm up and a warm down and count Easy segments between other Training Types the number of Easy Training Type segments is 6 repetitions.

Compliance Count Ups:

An assessment of what Training Types need to be completed during the workout is made every 20 mins. This means that the system works out what scheduled training has been completed and what has not been completed allowing the user some explanation of what is left to train. Because the classification system outlined previously can automatically detect a Training Type, it allows the user to do Training Types when it is most suitable so it is useful to be informed of what Training Types are left to train as the user moves through the workout.

For example, after 20 mins of training the user may have completed 1 repetition of Up Tempo and have completed 1 Hill. The system analyses this against the plan of 4 Up tempo repetitions and 3 Hills and the comment is "Training to complete; 3 Up tempo and 2 Hills, Time: 20 mins." The same system can be applied to more detailed performance and technique coaching.

5. System Requirements

It will be appreciated that the system of the invention may be implemented on any suitable hardware system, platform or architecture. The hardware system may be provided on-board a device used by the user or on a remote server for example, and preferably comprises at least a processor for running the classification system and in particular the algorithms, at least one memory component for storing at least the algorithms and the threshold criteria, and interface circuitry for communicating with external components that either directly or indirectly provide sensor output data. It will be appreciated that the processor may be any form of programmable hardware device, whether a CPU, Digital Signal Processor, Field-Programmable Gate Array, Microcontroller, Application-Specific Integrated Circuit, or the like.

There are 3 possible configurations for housing the classification system.

The data is processed 'on board' a measurement device (i.e. the classification system is within the measurement/monitoring device), Data is processed via manual (controlled by user) or automatic transfer (upload and download) of data via a communications network (e.g. telecommunications, wifi etc) to a remote server that contains the classification system, or manual or automatic transfer of data to a home computer that either contains the system or that transfers (upload and download) the data to a remote server that contains the system.

They system may house the infrastructure for the classification and allow a person, trainer or coach to input the one or more parameters and/or the one or more associated thresholds that define an activity.

Figure 10:
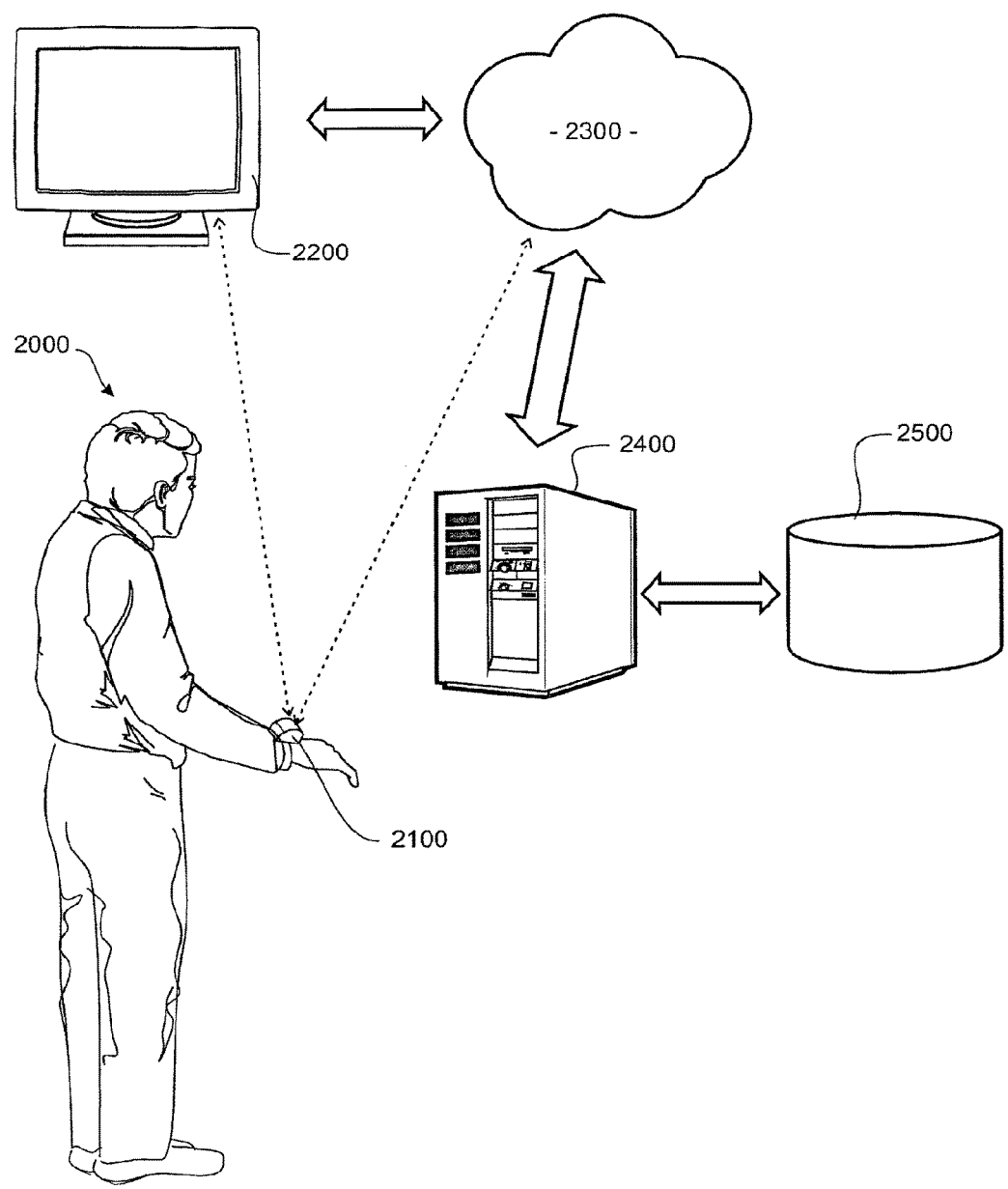
FIG. 10 is a block diagram showing the components associated with the system of the invention.

FIG. 10 shows an exemplary diagram of a user 2000 exercising or engaging in one or more activities (i.e. engaging in an activity session) whilst wearing one or more parameter sensing devices 2100 (which can be any combination of devices as explained in the sensor types section above). The device(s) 2100 collect information on the activity session and in particular data streams associated with the parameters required to classify the activities performed during the user's exercise/activity session. The device(s) 2100 may automatically process the data 'on board' (or manually when the user prompts the device to process the data for example) if the classification system is housed within the monitoring device(s). Alternatively or in addition the data may be automatically sent over to an analysis system 2400 (which may reside in a remote server or a home computer), either wirelessly or via cables, and if sent to a remote server preferably e.g. via a network. Instead of automatic transmission of the data, the user may upload the data manually to a home computer 2200 connected to the analysis system 2400 via a network 2300 or even directly to a remote server where the analysis system resides. The system (whether in the monitoring device, personal computer or remote server or elsewhere) processes the data by accessing memory 2500 (again this may be in the monitoring device, personal computer or remote server and is not necessarily in the same place as the processing circuitry) containing the classification system algorithms and threshold criteria (and preferably user information) to determine the activities conducted and the level of performance as described above. The system 2400 may then interpret this data and any other activity data provided by the devices 2100 to provide feedback to the user and/or alter a training program stored in memory 2500. The analysis system 2400 may communicate to the user's computer or devices 2100 via any communication means known in the art.

The invention is also intended to cover a method of analysing an exercise session as employed by the system described above.

Classification Tables

TABLE 1

| | Weight Loss - Walking/Running Classification System | | | | | |
|---|---|---|---|---|---|---|
| Classification of Activity Type | Primary Intensity measurement system | Metrics Used (Parameters) | Algorithm | Measurement Sensor/s GPS Speed would need smoothing. | Example of Output | Edge Forgiveness is a period where Activity Type can 'drop out' of zone without ending the Identification Period for that Activity Type |

| Activity | Classification of Activity Type | Primary Intensity measurement system | Metrics Used (Parameters) | Algorithm | Measurement Sensor/s | Example of Output | Type |
|---|---|---|---|---|---|---|---|
| Inactive | Inactive Upright | Speed or Power (GPS, Accelerometer, indoor/mechanical) | Positional Status AND | also Historic Averages, and Calibration | GPS Altitude would require error correction. | Inactive Upright Identified | Collected Raw Data over the Identified Activity Period |
| | | | | Upright | Accelerometer | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | | Speed or | Speed <2 km/hr for more than 15 sec | GPS or Accelerometer | | |
| | | | or Power | Power <25 w for more than 15 sec | Power (direct or indirect) | | |
| | | | Stride Rate: | <10 strides per minute | Accelerometer | | |
| | | Heart Rate & Speed or Power | Heart Rate AND Positional Status AND | >30% <45% of AT heart rate >30% <45% HR max | Heart Rate | Inactive Upright Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | | | | Upright | Accelerometer | | |
| | | | Speed or | Speed <2 km/hr for more than 2 mins | GPS or Accelerometer | | |
| | | | or Power | Power <25 w for more than 15 sec | Power (direct or indirect) | | |
| | | | Stride Rate: | <10 strides per minute | Accelerometer | | |
| | | Heart Rate & Accelerometer | Heart Rate AND Movement Detected AND | >30% <45% of AT heart rate >30% <45% HR max | Heart Rate | Inactive Upright Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force |
| | | | | less than pedometer measure of 5 strides/min | Accelerometer | | |

TABLE 1-continued

Weight Loss - Walking/Running Classification System

| Activity | Classification of Activity Type | Weight Loss - Walking/Running Classification System Primary Intensity measurement system | Metrics Used (Parameters) | Algorithm also Historic Averages, and Calibration | Measurement Sensor/s GPS Speed would need smoothing. GPS Altitude would require error correction. | Example of Output | Edge Forgiveness is a period where Activity Type can 'drop out' of zone without ending the Identification Period for that Activity Type Collected Raw Data over the Identified Activity Period |
|---|---|---|---|---|---|---|---|
| | | | Positional Status | Upright | | | Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | | Stride Rate: | <10 strides per minute | Accelerometer | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force |
| Inactive Rest | | Speed (GPS, Accelerometer, indoor/mechanical) or Power & Heart Rate (or respiration rate) | Positional Status AND Speed | Prone Speed <2 km/hr for more than 15 sec | Accelerometer Accelerometer GPS or Accelerometer | Inactive Rest Identified | Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | R-R could be used | or Power AND Heart Rate or or Respiration Rate | Power <25 w for more than 15 sec <40% of AT heart rate <37% HR max <12 breaths a minute | Power (direct or indirect) Heart Rate Heart Rate or Direct | | |
| | | Accelerometer & Heart Rate (or Respiration Rate) | Positional Status AND Heart Rate or or Respiration Rate | Prone <40% of AT heart rate <37% HR max <12 breaths a minute | Accelerometer Heart Rate Heart Rate or Direct | Inactive Rest Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users |

TABLE 1-continued

Weight Loss - Walking/Running Classification System

| Activity | Classification of Activity Type | Weight Loss - Walking/Running Classification System | | | Measurement Sensor/s GPS Speed would need smoothing. GPS Altitude would require error correction. | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm | | | Collected Raw Data over the Identified Activity Period |
| | Inactive Prone | Speed (GPS, Accelerometer, indoor/mechanical) or Power & Heart Rate (or respiration rate) | Positional Status AND | also Historic Averages, and Calibration | | | (including information on their Activities), Direction to User is Facing, Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | | Prone | | Inactive Prone Identified | |
| | | | Speed | Speed <2 km/hr for more than 15 sec | Accelerometer GPS or Accelerometer | | |
| | | | or Power AND | Power <25 w for more than 15 sec | Power (direct or indirect) | | |
| | | | Heart Rate or | >40% of AT heart rate >37% HR max | Heart Rate | | |
| | | R-R could be used | or Respiration Rate | >12 breaths a minute | Heart Rate or Direct | | |
| | | Accelerometer & Heart Rate (or Respiration Rate) | Positional Status AND | Prone | Accelerometer | Inactive Prone Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | Heart Rate or | >40% of AT heart rate >37% HR max | Heart Rate | | |
| | | | or Respiration Rate | >12 breaths a minute | Heart Rate or Direct | | |
| Walking | Easy Walking | | Altitude change (slope, gradient) | Slope <2 degrees (4% gradient) and >−2 degrees (−4%) stop: gradient >2 degrees over 6 meters vertical gain | GPS, Barometer, DEM, Inclinometer | Easy Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |

TABLE 1-continued

Weight Loss - Walking/Running Classification System

| Activity | Classification of Activity Type | Weight Loss - Walking/Running Classification System | | | Measurement Sensor/s GPS Speed would need smoothing. | Edge Forgiveness is a period where Activity Type can 'drop out' of zone without ending the Identification Period for that Activity | |
|---|---|---|---|---|---|---|---|
| | | Primary Intensity measurement system | Metrics Used (Parameters) | Algorithm also Historic Averages, and Calibration | | Example of Output | Type Collected Raw Data over the Identified Activity Period |
| | | Speed (GPS, Accelerometer, indoor/mechanical) or Power | | stop: gradient >2 degrees > 30 secs | GPS Altitude would require error correction. | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | AND | with 'edge forgiveness' (1-9 secs) | | | Weather Forecast, Location of other Users (including information on their Activities), Direction to User is Facing, |
| | | | Speed or | <45% of AT speed | GPS or Accelerometer | | |
| | | | or Power Possible Extra Parameter: | <45% of AT Power | Power (direct or indirect) | | |
| | | | Stride Rate: | >40 and <66 steps a min (1 full cycle L & R legs) Speed or Heart Rate equivelant to Intial Calibration of 3-4 of Max Effort via User Rating | Accelerometer | | |
| | | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Easy Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | Heart Rate | AND | with 'edge forgiveness' (1-9 secs) <60% of AT heart rate <55% HR max (AT HR - 40 bts & AT HR - 110 bts) | Heart Rate | | |
| | | | Heart Rate Possible Extra Parameter: | | | | |
| | | | Stride Rate: | <66 steps a min (1 full cycle L & R legs) Speed or Heart Rate equivilent | Accelerometer | | |

TABLE 1-continued

Weight Loss - Walking/Running Classification System

| Activity | Classification of Activity Type | Weight Loss - Walking/Running Classification System Primary Intensity measurement system | Metrics Used (Parameters) | Algorithm | Measurement Sensor/s GPS Speed would need smoothing. GPS Altitude would require error correction. | Example of Output | Edge Forgiveness is a period where Activity Type can 'drop out' of zone without ending the Identification Period for that Activity Type |
|---|---|---|---|---|---|---|---|
| | | | | also Historic Averages, and Calibration to Initial Calibration of 3-4 of Max Effort via User Rating | | | Collected Raw Data over the Identified Activity Period |
| | Rolling Hills - Walking | | Altitude change (slope, gradient) | gradient >2 degrees (4%) gradient) <8 degrees (15%) > 7 m, <20 m vertical gain | GPS, Barometer, DEM, Inclinometer | Rolling Hill Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | | gradient >2 degrees >70 secs, <200 secs | | | |
| | | | AND | with 'edge forgiveness' (1-9 secs) | | | Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power | Speed or or Power | <7 km/hr <power calc for 7 km/hr taking into account and slope | | | |
| | | No Heart Rate | Possible Extra Parameter: Stride Rate: | <66 steps a min (1 full cycle L & R legs) | | | |
| | Hills - Walking | | Altitude change (slope, gradient) | gradient >2 degrees (4%) gradient) <8 degrees (15%) > 20 m, <30 m vertical gain | GPS, Barometer, DEM, Inclinometer | Hill Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | | gradient >2 degrees >200 secs <410 secs | | | |
| | | | AND | with 'edge forgiveness' (1-9 secs) | | | Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power | Speed or or Power | <7 km/hr <power calc for 7 km/hr taking into account and slope | | | |

TABLE 1-continued

Weight Loss - Walking/Running Classification System

| Activity | Classification of Activity Type | Weight Loss - Walking/Running Classification System | | | Measurement Sensor/s GPS Speed would need smoothing. GPS Altitude would require error correction. | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics | Used (Parameters) also Historic Averages, and Calibration | | | Collected Raw Data over the Identified Activity Period |
| | Long Climb - Walking | No Heart Rate | Possible Extra Parameter: Stride Rate: Altitude change (slope, gradient) | <66 steps a min (1 full cycle L & R legs) gradient >2 degrees (4%) gradient) <8 degrees (15%) >30 m vertical gain gradient >2 degrees >410 secs | GPS, Barometer, DEM, Inclinometer | Long Climb Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | AND | with 'edge forgiveness' (1-9 secs) | | | Environmental Temp, Heat Index, Wind Chill, Altitude, Slope/Gradient, Wind Speed, Weather (rain etc), Distance |
| | | Speed (GPS, Accelerometer, indoor/mechanical) or Power | Speed or or Power | <7 km/hr <power calc for 7 km/hr taking into account and slope | | | Weather Forecast, Location of other Users (including information on their Activities), Direction to User is Facing, |
| | Fat Burning Zone | No Heart Rate | Possible Extra Parameter: Stride Rate: Altitude change (slope, gradient) | <66 steps a min (1 full cycle L & R legs) Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Fast Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | AND | with 'edge forgiveness' (1-9 secs) | | | Environmental Temp, Heat Index, Wind Chill, Altitude, Slope/Gradient, Wind Speed, Weather (rain etc), Distance |
| | | Speed (GPS, | | | | | |

TABLE 1-continued

Weight Loss - Walking/Running Classification System

| Activity | Classification of Activity Type | Primary Intensity measurement system | Metrics Used (Parameters) | Algorithm | Measurement Sensor/s | Example of Output | Type |
|---|---|---|---|---|---|---|---|
| | | | | | GPS Speed would need smoothing. | | Edge Forgiveness is a period where Activity Type can 'drop out' of zone without ending the Identification Period for that Activity |
| | | | | also Historic Averages, and Calibration | GPS Altitude would require error correction. | Collected Raw Data over the Identified Activity Period | |
| | | Accelerometer, indoor/mechanical) or Power | Speed or | 45-60% of AT speed | GPS or Accelerometer | | Weather Forecast, Location of other Users (including information on their Activities), Direction to User is Facing, |
| | | | or Power Possible Extra Parameter: | 45-60% of AT Power | Accelerometer Power (direct or indirect) | | |
| | | | Stride Rate: | <66 steps a min (1 full cycle L & R legs) Speed or Heart Rate equivlent to Intial Calibration of 5-6 of Max Effort via User Rating | Accelerometer | | |
| | | | Altitude change (slope, gradient) | Slope <2 degrees (4% gradient) and >-2 degrees (-4%) | GPS, Barometer, DEM, Inclinometer | Fast Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | Heart Rate | | stop: gradient >2 degrees over 6 meters vertical gain | | | Environmental Temp, Heat Index, Wind Chill, Altitude, Slope/Gradient, Wind Speed, Weather (rain etc), Distance |
| | | | | stop: gradient >2 degrees > 30 secs | | | Weather Forecast, Location of other Users (including information on their Activities), Direction to User is Facing, |
| | | | AND | with 'edge forgiveness' (1-9 secs) 55-70% of AT heart rate 55-65% HR max (AT HR - 20 bts) & AT HR - 50 bts) | Heart Rate | | |
| | | | Heart Rate Possible Extra Parameter: | | | | |
| | | | Stride Rate: | <66 steps a min (1 full cycle L & R legs) Speed or Heart Rate equivlent to Intial Calibration of 3-4 of Max Effort via User Rating | Accelerometer | | |
| Running | Low Speed - Run | | Altitude change (slope, gradient) | Slope <2 degrees (4% gradient) and >-2 degrees (-4%) | GPS, Barometer, DEM, Inclinometer | Low Speed Run Identified | Speed, Terrain, Elapsed Time, Time of Day, Location, Altitude, Movement Incidence, Force of Movement, Turnover, Distance per Turnover |

TABLE 1-continued

Weight Loss - Walking/Running Classification System

| Activity | Classification of Activity Type | Weight Loss - Walking/Running Classification System Primary Intensity measurement system | Metrics Used (Parameters) | Algorithm also Historic Averages, and Calibration | Measurement Sensor/s GPS Speed would need smoothing. | Example of Output | Edge Forgiveness is a period where Activity Type can 'drop out' of zone without ending the Identification Period for that Activity Type Collected Raw Data over the Identified Activity Period |
|---|---|---|---|---|---|---|---|
| | | Speed (GPS, Accelerometer, indoor/mechanical) or Power | | stop: gradient >2 degrees over 6 meters vertical gain | GPS Altitude would require error correction. | | HR, R-R (HRV), ECG, BP, Respiration Rate, Body Temperature, Glucose & Cholesterol Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | | stop: gradient >2 degrees > 30 secs | | | Weather Forecast, Location of other Users (including information on their Activities), Direction to User is Facing. |
| | | | AND | with edge 'forgiveness' (1-9 secs) | | | |
| | | | Speed or | 60-90% of AT speed | GPS or Accelerometer | | |
| | | | or Power Possible Extra Parameter: | 60-90% of AT Power | Power (direct or indirect) | | |
| | | | Stride Rate: | >70 steps a min (1 full cycle L & R legs) Speed or Heart Rate equivilent to Initial Calibration of 6.5-7.5 of Max Effort via User Rating | Accelerometer | | |
| | | | Altitude change (slope, gradient) | Slope <2 degrees (4% gradient) and >-2 degrees (-4%) | GPS, Barometer, DEM, Inclinometer | Low Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | Heart Rate | | stop: gradient >2 degrees over 6 meters vertical gain stop: gradient >2 degrees >30 secs | | | Weather Forecast, Location of other Users (including information on their Activities), Direction to User is Facing. |
| | | | AND | with 'edge forgiveness' (1-9 secs) 70-80% of AT heart rate 65-75% HR max (AT HR - 10 bts & AT HR - 40 bts) | Heart Rate | | |
| | | | Heart Rate Possible Extra Parameter: | >70 steps a min (1 full cycle L | | | |

TABLE 1-continued

Weight Loss - Walking/Running Classification System

| Activity | Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|---|
| | | | Stride Rate: (& R legs) | Speed or Heart Rate equivilent to Initial Calibration of 6.5-7.5 of Max Effort via User Rating also Historic Averages, and Calibration | GPS Altitude would require error correction. Accelerometer | | Collected Raw Data over the Identified Activity Period |
| | Rolling Hills - Running | | Altitude change (slope, gradient) | gradient >2 degrees (4%) gradient) <8 degrees (15%) > 7 m, <20 m vertical gain | GPS, Barometer, DEM, Inclinometer | Rolling Hill Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | | gradient >2 degrees >70 secs, <200 secs | | | Environmental Temp, Heat Index, Wind Chill, Altitude, Slope/Gradient, Wind Speed, Weather (rain etc) Distance |
| | | Speed (GPS, Acclerometer, indoor/mechanical) or Power | AND Speed or or Power Possible Extra Parameter: | with 'edge forgiveness' (1-9 secs) >7 km/hr >power calc for 7 km/hr taking into account and slope | | | Weather Forecast, Location of other Users (including information on their Activities), Direction to User is Facing, |
| | | No Heart Rate | Stride Rate: (& R legs) | >70 steps a min (1 full cycle L | | | |
| | Hills - Running | | Altitude change (slope, gradient) | gradient >2 degrees (4%) gradient) <8 degrees (15%) > 20 m, <30 m vertical gain | GPS, Barometer, DEM, Inclinometer | Hills Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | | gradient >2 degrees >200 secs <410 secs | | | Environmental Temp, Heat Index, Wind Chill, Altitude, Slope/Gradient, Wind Speed, Weather (rain etc) Distance |
| | | Speed (GPS, Acclerometer, indoor/mechanical) or Power | AND Speed or or Power | with 'edge forgiveness' (1-9 secs) >7 km/hr >power calc for 7 km/hr taking into account and slope | | | Weather Forecast, Location of other Users (including information on their Activities), |

TABLE 1-continued

Weight Loss - Walking/Running Classification System

| Activity Classification of Activity Type | Weight Loss - Walking/Running Classification System | | | Measurement Sensor/s | Edge Forgiveness is a period where Activity Type can 'drop out' of zone without ending the Identification Period for that Activity | |
|---|---|---|---|---|---|---|
| | Primary Intensity measurement system | Metrics Used (Parameters) | Algorithm | | Example of Output | Type |
| | | Possible Extra Parameter: | also Historic Averages, and Calibration | GPS Speed would need smoothing. | | Direction to User is Facing, |
| Long Climb - Running | No Heart Rate | Stride Rate: >70 steps a min (1 full cycle L & R legs) | | GPS Altitude would require error correction. | | Collected Raw Data over the Identified Activity Period |
| | | Altitude change (slope, gradient) | gradient >2 degrees (4%) gradient) <8 degrees (15%) > 30 m vertical gain | GPS, Barometer, DEM, Inclinometer | Long Climb Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | AND | gradient >2 degrees >410 secs with 'edge forgiveness' (1-9 secs) | | | |
| | Speed (GPS, Acclerometer, indoor/mechanical) or Power | Speed or Power | >7 km/hr >power calc for 7 km/hr taking into account and slope | | | |
| High Speed - Run | No Heart Rate | Possible Extra Parameter: Stride Rate: >70 steps a min (1 full cycle L & R legs) | | | | |
| | | Altitude change (slope, gradient) | Slope <2 degrees (4% gradient) and >-2 degrees (-4%) | GPS, Barometer, DEM, Inclinometer | High Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | stop: gradient >2 degrees over 6 meters vertical gain | | | |
| | | | stop: gradient >2 degrees > 30 secs | | | |
| | | AND | with 'edge forgiveness' (1-9 secs) | | | |
| | Speed (GPS, | | | | | |

TABLE 1-continued

Weight Loss - Walking/Running Classification System

| Activity | Classification of Activity Type | Weight Loss - Walking/Running Classification System | | | Measurement Sensor/s | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm | | | |
| | | Acclerometer, indoor/mechanical) or Power | | also Historic Averages, and Calibration | GPS Speed would need smoothing. | | Collected Raw Data over the Identified Activity Period |
| | | | Speed or | 90-95% of AT speed | GPS or Accelerometer Power (direct or indirect) | | Weather Forecast, Location of other Users (including information on their Activities), Direction to User is Facing, |
| | | | or Power Possible Extra Parameter: | 90-95% of AT Power | | | |
| | | | Stride Rate: | >70 steps a min (1 full cycle L & R legs) Speed or Heart Rate equivalent to Intial Calibration of 7.5-8.5 of Max Effort via User Rating | Accelerometer | | |
| | | | Altitude change (slope, gradient) | Slope <2 degrees (4% gradient) and >-2 degrees (-4%) | GPS, Barometer, DEM, Inclinometer | High Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Heaviness of Footfall, L-R Power Balance, Force Measures for Gait, Environmental Gas Concentrations, |
| | | Heart Rate | | stop: gradient >2 degrees over 6 meters vertical gain stop: gradient >2 degrees > 30 secs | | | Environmental Temp, Heat Index, Wind Chill, Altitude, Slope/Gradient, Wind Speed, Weather (rain etc), Distance |
| | | | AND | with 'edge forgiveness' (1-9 secs) 80-90% of AT heart rate 75-85% HR max (AT HR & AT HR - 10 bts) | Heart Rate | | Weather Forecast, Location of other Users (including information on their Activities), Direction to User is Facing, |
| | | | Heart Rate Possible Extra Parameter: | | | | |
| | | | Stride Rate: | >70 steps a min (1 full cycle L & R legs) Speed or Heart Rate equivalent to Intial Calibration of 7.5-8.5 of Max Effort via User Rating | Accelerometer | | |
| Out of Zone - Too Fast | | | Altitude change (slope, gradient) | Slope <2 degrees (4% gradient) and >-2 degrees (-4%) | GPS, Barometer, DEM, Inclinometer | Too fast Identified Very High Speed Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | | | stop: gradient >2 degrees over 6 meters vertical gain | | | |

TABLE 1-continued

Weight Loss - Walking/Running Classification System

| Activity Classfication of Activity Type | Weight Loss - Walking/Running Classification System | | | Measurement Sensor/s | Example of Output | Edge Forgiveness is a period where Activity Type can 'drop out' of zone without ending the Identification Period for that Activity Type |
|---|---|---|---|---|---|---|
| | Primary Intensity measurement system | Metrics Used (Parameters) | Algorithm | | | |
| | | | also Historic Averages, and Calibration | GPS Speed would need smoothing. GPS Altitude would require error correction. | | Collected Raw Data over the Identified Activity Period |
| | Speed (GPS, Accelerometer, indoor/mechanical) or Power | | stop: gradient >2 degrees > 30 secs | | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | AND | with 'edge forgiveness' (1-9 secs) | | | Weather Forecast, Location of other Users (including information on their Activities), Direction to User is Facing, |
| | | Speed or | >95% of AT speed | GPS or Accelerometer Power (direct or indirect) | Too fast Identified | |
| | | or Power Possible Extra Parameter: | >95% of AT Power | | Very High Speed Identified | |
| | | Stride Rate: | >70 steps a min (1 full cycle L & R legs) Speed or Heart Rate equivlent to Intial Calibration of 7.5-8.5 of Max Effort via User Rating | Accelerometer | | |
| | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | Heart Rate | AND | with 'edge forgiveness' (1-9 secs) >90% of AT heart rate >85% HR max (AT HR & AT HR+ & -3 bts) | Heart Rate | | Weather Forecast, Location of other Users (including information on their Activities), Direction to User is Facing. |
| | | Heart Rate Possible Extra Parameter: | if Specialist: 90-101% AT heart rate & 85-95% of maximum Heart rate | | | |
| | | Stride Rate: | >70 steps a min (1 full cycle L & R legs) | Accelerometer | | |

TABLE 1-continued

Weight Loss - Walking/Running Classification System

| Activity | Classification of Activity Type | Weight Loss - Walking/Running Classification System | | | Measurement Sensor/s GPS Speed would need smoothing. GPS Altitude would require error correction. | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm | | | Collected Raw Data over the Identified Activity Period |
| | Non Specific Movement - Moderate Intensity | Speed (GPS, Accelerometer, indoor/mechanical) or Power | Speed | also Historic Averages, and Initial Calibration of 7.5-8.5 of Max Effort via User Rating Speed or Heart Rate equivilent to 2-6 km/hr | GPS or Accelerometer | Non Specific Movement Moderate Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing. |
| | | | AND Stride Rate: AND Postural Status | 5-40 impacts/strides per min, Time Uniformity >40 ms Upright | Accelerometer Accelerometer | | |
| | | Heart Rate | Heart Rate | >45% and <55% of AT HR (>37% and <60% of Maximum Heart Rate) | Heart Rate | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | | AND Stride Rate: AND Postural Status | 5-40 impacts/strides per min, Time Uniformity >40 ms Upright | Accelerometer Accelerometer | | |
| | Non Specific Movement - High Intensity | Speed (GPS, Accelerometer, indoor/mechanical) or Power | Speed | 2-6 km/hr | GPS or Accelerometer | Non Specific Movement High Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas |
| | | | AND | 40-60 impacts/strides per | | | |

TABLE 1-continued

Weight Loss - Walking/Running Classification System

| Activity | Classfication of Activity Type | Weight Loss - Walking/Running Classification System | | | Measurement Sensor/s GPS Speed would need smoothing. GPS Altitude would require error correction. | Edge Forgiveness is a period where Activity Type can 'drop out' of zone without ending the Identification Period for that Activity | |
|---|---|---|---|---|---|---|---|
| | | Primary Intensity measurement system | Metrics Used (Parameters) | Algorithm also Historic Averages, and Calibration | | Example of Output | Type Collected Raw Data over the Identified Activity Period |
| | | | Stride Rate: AND Postural Status | min, Time Uniformity >40 ms Upright | Accelerometer | | Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Measures for Footfall, L-R Power Balance, Force Heaviness of Footfall, L-R Power Balance, Force Measures for Gait, Environmental Gas Concentrations, |
| | | Heart Rate | Heart Rate | >55% and <70% of AT HR (>55% and <65% of Maximum Heart Rate) | Heart Rate | Non Specific Movement Moderate Intensity Identified | |
| | | | Stride Rate: AND Postural Status | 5-40 impacts/strides per min, Time Uniformity >40 ms Upright | Accelerometer | High Intensity Identified | Environmental Temp, Heat Index, Wind Chill, Altitude, Slope/Gradient, Wind Speed, Weather (rain etc), Distance Weather Forecast, Location of other Users (including information on their Activities), Direction to User is Facing, Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Measures for Footfall, L-R Power Balance, Force Heaviness of Footfall, L-R Power Balance, Force Measures for Gait, Environmental Gas Concentrations, |
| Non Specific Movement - Very High Intensity | | Speed (GPS, Acclerometer, indoor/mechanical) or Power | Speed | 2-6 km/hr | GPS or Accelerometer | Non Specific Movement Very High Intensity Identified | Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | Stride Rate: AND Postural Status | 60+ impacts/strides per min, Time Uniformity >40 ms Upright | Accelerometer | | Speed, Terrain, Elapsed Time, Time of Day, Location, Altitude, Movement Incidence, Force pf Movement, Turnover, Distance per Turnover HR, R-R (HRV), ECG, BP, Respiration Rate, |
| | | Heart Rate | Heart Rate | >70% of AT HR (>65% of Maximum Heart Rate) | Heart Rate | Non Specific Movement Very High | |

TABLE 1-continued

Weight Loss - Walking/Running Classification System

| Activity | Classification of Activity Type | Weight Loss - Walking/Running Classification System | | | Measurement Sensor/s | Edge Forgiveness is a period where Activity Type can 'drop out' of zone without ending the Identification Period for that Activity | |
|---|---|---|---|---|---|---|---|
| | | Primary Intensity measurement system | Metrics Used (Parameters) | Algorithm | | Example of Output | Type |
| | | | AND | also Historic Averages, and Calibration | GPS Speed would need smoothing. GPS Altitude would require error correction. | | Collected Raw Data over the Identified Activity Period |
| | | | Stride Rate: AND | 5-40 impacts/strides per min, Time Uniformity >40 ms | Accelerometer | Intensity Identified | Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | Postural Status | Upright | Accelerometer | | Environmental Temp, Heat Index, Wind Chill, Altitude, Slope/Gradient, Wind Speed, Weather (rain etc), Distance Weather Forecast, Location of other Users (including information on their Activities), Direction to User is Facing, |

TABLE 2

Activity Status Monitoring - Health/Military/Personel - Walking/Running Classification System

| Classification of Activity Type | Primary Intensity measurement system | Metrics Used (Parameters) | Algorithm also Historic Averages, and Calibration | Measurement Sensor/s GPS Speed would need smoothing. | Example of Output | Edge Forgiveness is a period where Activity Type can 'drop out' of zone without ending the Identification Period for that Activity Type Collected Raw Data over the Identified Activity Period |
|---|---|---|---|---|---|---|
| Inactive Upright | Speed or Power (GPS, Accelerometer, indoor/mechanical) | Positional Staus AND | Upright | GPS Altitude would require error correction. | Inactive Upright Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
|  |  | Speed or | Speed <2 km/hr for more than 15 sec | GPS or Accelerometer |  |  |
|  |  | or Power | Power <25 w for more than 15 sec | Power (direct or indirect) |  |  |
|  |  | Stride Rate: | <10 strides per minute | Accelerometer | Inactive Upright Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
|  | Heart Rate & Speed or Power | Heart Rate AND | >30% <45% of AT heart rate >30% <45% HR max | Heart Rate |  |  |
|  |  | Positional Staus AND | Upright |  |  |  |
|  |  | Speed or | Speed <2 km/hr for more than 2 mins | GPS or Accelerometer |  |  |
|  |  | or Power | Power <25 w for more than 15 sec | Power (direct or indirect) |  |  |
|  |  | Stride Rate: | <10 strides per minute | Accelerometer | Inactive Upright Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body |
|  | Heart Rate & Accelerometer | Heart Rate AND Movement | >30% <45% of AT heart rate >30% <45% HR max | Heart Rate |  |  |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | | GPS Speed would need smoothing. | | Collected Raw Data over the Identified Activity Period |
| | | Detected AND Positional Staus | also Historic Averages, and Calibration | GPS Altitude would require error correction. | | Temperature, Glucose & Cholesterol Levels, Pulse Oximetry, Steps, Gait Analysis |
| | | | less than pedometer measure of 5 strides/min | Accelerometer | | Heaviness of Footfall, L-R Power Balance, Force Measures for Gait, Environmental Gas Concentrations, |
| | | | Upright | Accelerometer | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| Inactive Rest | Speed (GPS, Accelerometer, indoor/mechanical) or Power & Heart Rate (or repsiration rate) | Stride Rate: | <10 strides per minute | Accelerometer | Inactive Rest Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | Positional Staus AND Speed or Power AND Heart Rate or Respiration Rate | Prone (<80 degree to upright) Speed <2 km/hr for more than 15 sec Power <25 w for more than 15 sec <40% of AT heart rate <37% HR max <12 breaths a minute | Accelerometer Accelerometer GPS or Accelerometer Power (direct or indirect) Heart Rate Heart Rate or Direct | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | R-R could be used | | | | |
| | Accelerometer & Heart Rate (or Respiration Rate) | Positional Staus AND Heart Rate or Respiration Rate | Prone (<80 degree to upright) <40% of AT heart rate <37% HR max <12 breaths a minute | Accelerometer Heart Rate Heart Rate or Direct | Inactive Rest Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type Collected Raw Data over the Identified Activity Period |
|---|---|---|---|---|---|---|
| Inactive Prone | Speed (GPS, Accelerometer, indoor/mechanical) or Power & Heart Rate (or respiration rate) R-R could be used | Positional Staus AND Speed or Power AND Heart Rate or Respiration Rate | also Historic Averages, and Calibration Prone (<80 degree to upright) Speed <2 km/hr for more than 15 sec Power <25 w for more than 15 sec >40% of AT heart rate >37% HR max >12 breaths a minute | GPS Altitude would require error correction. Accelerometer GPS or Accelerometer Power (director indirect) Heart Rate Heart Rate or Direct | Inactive Prone Identified | Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, |
| Inactive Prone | Accelerometer & Heart Rate (or Respiration Rate) | Positional Staus AND Heart Rate or Respiration Rate | Prone (<80 degree to upright) >40% of AT heart rate >37% HR max >12 breaths a minute | Accelerometer Heart Rate Heart Rate or Direct | Inactive Prone Identified | Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | also Historic Averages, and Calibration | GPS Speed would need smoothing. GPS Altitude would require error correction. | | Collected Raw Data over the Identified Activity Period |
| Easy Walking | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Easy Walking Identified | Resources, Goal Target, Mission Objectives Direction to User is Facing, Forwards vs Backwards vs Lateral Movement (left and right) Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | Speed (GPS, Acclerometer, indoor/mechanical) or Power | AND | with 'edge forgiveness' (1-9 secs) | | | |
| | | Speed or | <45% of AT speed | GPS or Accelerometer Power (direct or indirect) | | |
| | | or Power Possible Extra Parameter: | <45% of AT Power | | | |
| | | Stride Rate: | <66 steps a min (1 full cycle L & R legs) Speed or Heart Rate equivilent to Intial Calibration of 3-4 of Max Effort via User Rating | Accelerometer | | |
| | Heart Rate | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Easy Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of |
| | | AND | with 'edge forgiveness' (1-9 secs) <60% of AT heart rate <55% HR max (AT HR - 40 bts & AT HR - 110 bts) | | | |
| | | Heart Rate Possible Extra | | Heart Rate | | |

TABLE 2-continued

Activity Status Monitoring - Health/Military/Personel - Walking/Running Classification System

| Classification of Activity Type | Primary Intensity measurement system | Metrics | Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|---|
| | | | Parameter: Stride Rate: | <66 steps a min (1 full cycle L & R legs) | GPS Altitude would require error correction. GPS Speed would need smoothing. | | Collected Raw Data over the Identified Activity Period |
| | | | | also Historic Averages, and Calibration | Accelerometer | | Resources, Goal Target, Mission Objectives Direction to User is Facing, Forwards vs Backwards vs Lateral Movement (left and right) |
| | | | | Speed or Heart Rate equivlent to Intial Calibration of 3-4 of Max Effort via User Rating | | | |
| Rolling Hills - Walking | | | Altitude change (slope, gradient) | gradient >2 degrees (4%) gradient) <8 degrees (15%) > 7 m, <20 m vertical gain gradient >2 degrees >70 secs, <200 secs | GPS, Barometer, DEM, Inclinometer | Rolling Hill Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | Speed (GPS, Acclerometer, indoor/mechanical) or Power | | AND | with 'edge forgiveness' (1-9 secs) | | | |
| | | | Speed or Power Possible Extra Parameter: | <7 km/hr <power calc for 7 km/hr taking into account and slope | | | |
| Hills - Walking | | No Heart Rate | Stride Rate: Altitude change (slope, gradient) | <66 steps a min (1 full cycle L & R legs) gradient >2 degrees (4% gradient) <8 degrees (15%) > 20 m, <30 m vertical gain gradient >2 degrees >200 secs < 410 secs | GPS, Barometer, DEM, Inclinometer | Hill Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of |
| | Speed (GPS, Acclerometer, indoor/mechanical) or Power | | AND | with 'edge forgiveness' (1-9 secs) | | | |
| | | | Speed or Power Possible | <7 km/hr <power calc for 7 km/hr takinginto account and slope | | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | Extra Parameter: | also Historic Averages, and Calibration | GPS Speed would need smoothing. GPS Altitude would require error correction. | | Collected Raw Data over the Identified Activity Period Resources, Goal Target, Mission Objectives Direction to User is Facing, Forwards vs Backwards vs Lateral Movement (left and right) |
| Long Climb - Walking | No Heart Rate | Stride Rate: Altitude change (slope, gradient) | <66 steps a min (1 full cycle L & R legs) gradient >2 degrees (4%) gradient) <8 degrees (15%) > 30 m vertical gain gradient >2 degrees >410 secs | GPS, Barometer, DEM, Inclinometer | Long Climb Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | AND | with 'edge forgiveness' (1-9 secs) | | | |
| | Speed (GPS, Accelerometer, indoor/mechanical) or Power | Speed or Power Possible Extra Parameter: | <7 km/hr <power calc for 7 km/hr taking into account and slope | | | |
| Fast Walking | No Heart Rate | Stride Rate: Altitude change (slope, gradient) | <66 steps a min (1 full cycle L & R legs) Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Fast Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives |
| | | AND | with 'edge forgiveness' (1-9 secs) | | | |
| | Speed (GPS, Accelerometer, indoor/mechanical) or Power | Speed or Power | 45-60% of AT speed 45-60% of AT Power | GPS or Accelerometer Power (direct or indirect) | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | also Historic Averages, and Calibration | GPS Speed would need smoothing. GPS Altitude would require error correction. | | Collected Raw Data over the Identified Activity Period |
| | | Possible Extra Parameter: Stride Rate: | <66 steps a min (1 full cycle L & R legs) Speed or Heart Rate equivilent to Intial Calibration of 5-6 of Max Effort via User Rating | Accelerometer | Fast Walking Identified | Direction to User is Facing, Forwards vs Backwards vs Lateral Movement (left and right) |
| | Heart Rate | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives |
| | | AND | with 'edge forgiveness' (1-9 secs) 55-70% of AT heart rate 55-65% HR max (AT HR - 20 bts & AT HR - 50 bts) | Heart Rate | | |
| | | Heart Rate Possible Extra Parameter: Stride Rate: | <66 steps a min (1 full cycle L & R legs) Speed or Heart Rate equivilent to Intial Calibration of 5-6 of Max Effort via User Rating | Accelerometer | | Direction to User is Facing, Forwards vs Backwards vs Lateral Movement (left and right) |
| Low Speed - Run | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Low Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident |
| | Speed (GPS, Acclerometer, indoor/mechanical) or | AND | with 'edge forgiveness' (1-9 secs) | GPS or | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | also Historic Averages, and Calibration | GPS Altitude would require error correction. | | Collected Raw Data over the Identified Activity Period |
| | Power | Speed or | 60-90% of AT speed | Accelerometer | | Weather Forecast, Location of other Users (including information on their Activities), Location of Resources, Goal Target, Mission Objectives Direction to User is Facing, Forwards vs Backwards vs Lateral Movement (left and right) |
| | | or Power Possible Extra Parameter: | 60-90% of AT Power | Power (direct or indirect) | | |
| | | Stride Rate: | >70 steps a min (1 full cycle L & R legs) Speed or Heart Rate equivilent to Initial Calibration of 6.5-7.5 of Max Effort via User Rating | Accelerometer | | |
| | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Low Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | AND | with 'edge forgiveness' (1-9 secs) 70-80% of AT heart rate 65-75% HR max (AT HR - 10 bts & AT HR - 40 bts) | | | |
| | Heart Rate | Heart Rate Possible Extra Parameter: | | Heart Rate | | |
| | | Stride Rate: | >70 steps a min (1 full cycle L & R legs) Speed or Heart Rate equivilent to Initial Calibration of 6.5-7.5 of Max Effort via User Rating | Accelerometer | | |
| Rolling Hills - Running | | Altitude change (slope, gradient) | gradient >2 degrees (4% gradient) <8 degrees (15%) > 7 m, <20 m vertical gain gradient >2 degrees >70 secs, <200 secs | GPS, Barometer, DEM, Inclinometer | Rolling Hill Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | AND | with 'edge forgiveness' (1-9 secs) | | | |
| | Speed (GPS, Acclerometer, | | | | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | also Historic Averages, and Calibration | GPS Speed would need smoothing. GPS Altitude would require error correction. | | Collected Raw Data over the Identified Activity Period |
| | indoor/mechanical) or Power | Speed or | >7 km/hr | | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | or Power Possible Extra Parameter: Stride Rate: | >power calc for 7 km/hr taking into account and slope >70 steps a min (1 full cycle L & R legs) | | | |
| Hills - Running | No Heart Rate | Altitude change (slope, gradient) | gradient >2 degrees (4% gradient) <8 degrees (15%) > 20 m, <30 m vertical gain gradient >2 degrees >200 secs < 410 secs | GPS, Barometer, DEM, Inclinometer | Hills Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | Speed (GPS, Accelerometer, indoor/mechanical) or Power | AND Speed or | with 'edge forgiveness' (1-9 secs) >7 km/hr | | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | or Power Possible Extra Parameter: Stride Rate: | >power calc for 7 km/hr taking into account and slope >70 steps a min (1 full cycle L & R legs) | | | |
| Long Climb - Running | No Heart Rate | Altitude change (slope, gradient) | gradient >2 degrees (4% gradient) <8 degrees (15%) > 30 m vertical gain gradient >2 degrees >410 secs | GPS, Barometer, DEM, Inclinometer | Long Climb Running Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | Speed (GPS, Accelerometer, indoor/mechanical) or Power | AND Speed or or Power | with 'edge forgiveness' (1-9 secs) >7 km/hr >power calc for 7 km/hr taking into account and slope | | | Environmental Temp, Heat Index, Wind Chill, Altitude, Slope/Gradient, Wind Speed, Weather (rain etc), Distance, Location of an object or incident Weather Forecast, Location of other Users (including |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | also Historic Averages, and Calibration | GPS Speed would need smoothing. GPS Altitude would require error correction. | | Collected Raw Data over the Identified Activity Period |
| High Speed - Run | No Heart Rate | Possible Extra Parameter: Stride Rate: | >70 steps a min (1 full cycle L & R legs) | | | information on their Activities), Location of Resources, Goal Target, Mission Objectives Direction to User is Facing, Forwards vs Backwards vs Lateral Movement (left and right) |
| | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | High Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | AND | with 'edge forgiveness' (1-9 secs) | | | Weather Forecast, Location of other Users (including information on their Activities), Location of Resources, Goal Target, Mission Objectives Direction to User is Facing, Forwards vs Backwards vs Lateral Movement (left and right) |
| | Speed (GPS, Accelerometer, indoor/mechanical) or Power | Speed or | 90-95% of AT speed | GPS or Accelerometer | | |
| | | or Power Possible Extra Parameter: | 90-95% of AT Power | Power (direct or indirect) | | |
| | | Stride Rate: | >70 steps a min (1 full cycle L & R legs) Speed or Heart Rate equivilent to Initial Calibration of 7.5-8.5 of Max Effort via User Rating | Accelerometer | | |
| | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | High Speed Run Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident |
| | | AND | with 'edge forgiveness' (1-9 secs) 80-90% of AT heart rate 75-85% HR max (AT HR & AT HR - 10 bts) | | | |
| | | Heart Rate | | Heart Rate | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type Collected Raw Data over the Identified Activity Period |
|---|---|---|---|---|---|---|
| | | Possible Extra Parameter: | also Historic Averages, and Calibration | GPS Altitude would require error correction. | | Weather Forecast, Location of other Users (including information on their Activities), Location of Resources, Goal Target, Mission Objectives Direction to User is Facing, Forwards vs Backwards vs Lateral Movement (left and right) |
| | | Stride Rate: | >70 steps a min (1 full cycle L & R legs) Speed or Heart Rate equivilent to Intial Calibration of 7.5-8.5 of Max Effort via User Rating | Accelerometer | | |
| Out of Zone - Too Fast Specialist: Very High Speed - Run | | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Too fast Identified Very High Speed Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | Speed (GPS, Acclerometer, indoor/mechanical) or Power | AND | with 'edge forgiveness' (1-9 secs) | | | Environmental Temp, Heat Index, Wind Chill, Altitude, Slope/Gradient, Wind Speed, Weather (rain etc), Distance, Location of an object or incident |
| | | Speed or | >95% of AT speed (if Specialist: 95-101% AT speed) >95% of AT Power (if Specialist: 95-101% AT power) | GPS or Accelerometer | | Weather Forecast, Location of other Users (including information on their Activities), Location of Resources, Goal Target, Mission Objectives Direction to User is Facing, Forwards vs Backwards vs Lateral Movement (left and right) |
| | | or Power Possible Extra Parameter: | | Power (direct or indirect) | | |
| | | Stride Rate: | >70 steps a min (1 full cycle L & R legs) Speed or Heart Rate equivilent to Intial Calibration of 8.5-9.5 of Max Effort via User Rating | Accelerometer | | |
| | Heart Rate | Altitude change (slope, gradient) | Slope <2 degrees (4% gradient) and >-2 degrees (-4%) stop: gradient >2 degrees over 6 meters vertical gain | GPS, Barometer, DEM, Inclinometer | Too fast Identified Very High Speed Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | | | | Collected Raw Data over the Identified Activity Period |
| | | AND | stop: gradient >2 degrees > 30 secs with 'edge forgiveness' (1-9 secs) >90% of AT heart rate >85% HR max (AT HR & AT HR+ & −3 bts) | GPS Altitude would require error correction. | | Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | Heart Rate Possible Extra Parameter: | if Specialist: 90-101% AT heart rate & 85-95% of maximum Heart rate | Heart Rate | | |
| | | Stride Rate: | >70 steps a min (1 full cycle L & R legs) Speed or Heart Rate equivilent to Intial Calibration of 8.5-9.5 of Max Effort via User Rating | Accelerometer | | |
| Specialist: Sprint Flat | Speed (GPS, Accelerometer, indoor/mechanical) or Power | Altitude change (slope, gradient) | Slope <2 degrees (4% gradient) and >−2 degrees (−4%) stop: gradient >2 degrees over 6 meters vertical gain stop: gradient >2 degrees > 30 secs with 'edge forgiveness' (1-9 secs) | GPS, Barometer, DEM, Inclinometer | Flat Sprint Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | AND | | | | |
| | | Speed or | >101% of AT speed | GPS or Accelerometer | | |
| | | or Power Possible Extra Parameter: | >105% of AT Power | Power (direct or indirect) | | |
| | | Stride Rate: | >85 steps a min (1 full cycle L & R legs) Speed or Heart Rate equivilent to Intial Calibration of >9 of Max Effort via User Rating | Accelerometer | | |
| | | Altitude change (slope, | Slope <2 degrees (4% gradient) and >−2 degrees | GPS, Barometer, DEM, | Flat Sprint | Speed, Terrain, Elapsed Time, Time of Day, Location, Altitude, Movement Incidence, Force pf Movement, Turnover, Distance per Turnover |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type Collected Raw Data over the Identified Activity Period |
|---|---|---|---|---|---|---|
| | Heart Rate | gradient) | (−4%) also Historic Averages, and Calibration stop: gradient >2 degrees over 6 meters vertical gain stop: gradient >2 degrees > 30 secs | Inclinometer GPS Altitude would require error correction. | Identified | HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | AND | with 'edge forgiveness' (1-9 secs) >101% of AT heart rate >95% HR max (>AT HR +3 bts) | | | |
| | | Heart Rate Possible Extra Parameter: | if Specialist: 90-101% AT heart rate & 85-95% of maximum Heart rate | Heart Rate | | |
| | | Stride Rate: | >85 steps a min (1 full cycle L & R legs) Speed or Heart Rate equivilent to Initial Calibration of >9 of Max Effort via User Rating | Accelerometer | | |
| Specialist: Sprint Hills | Speed (GPS, Accelerometer, indoor/mechanical) or Power | Altitude change (slope, gradient) | gradient >2 degrees (4%) gradient) <8 degrees (15%) > 6 m, vertical gain gradient >2 degrees >70 secs, with 'edge forgiveness' (1-9 secs) | GPS, Barometer, DEM, Inclinometer | Hill Sprint Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | AND | >12 km/hr >power calc for 12 km/hr taking into account and slope | | | |
| | | Speed or or Power Possible Extra Parameter: | | | | |
| | No Heart Rate | Stride Rate: | >85 steps a min (1 full cycle L & R legs) | | | |
| | Heart Rate | Altitude change (slope, gradient) | gradient >2 degrees (4%) gradient) <8 degrees (15%) > 6 m, vertical gain gradient >2 degrees >70 secs, with 'edge forgiveness' (1-9 sec) | GPS, Barometer, DEM, Inclinometer | Hill Sprint Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | AND | | | | |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type |
|---|---|---|---|---|---|---|
| | | | | | | Collected Raw Data over the Identified Activity Period |
| | | | >101% of AT heart rate >95% HR max (>AT HR +3 bts) | GPS Altitude would require error correction. | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | Heart Rate Possible Extra Parameter: | if Specialist: 90-101% AT heart rate & 85-95% of maximum Heart rate | Heart Rate | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | Stride Rate: | >85 steps a min (1 full cycle L & R legs) Speed or Heart Rate equivilent to Initial Calibration of >9.5 of Max Effort via User Rating | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| Specialist: Crawling | Speed (GPS, Acclerometer, indoor/mechanical) or Power & Heart Rate (or repristion rate) | Positional Staus Speed or Power | Prone Speed >2 km/hr for more than 15 sec Power >25 w for more than 15 sec | Accelerometer Accelerometer GPS or Accelerometer Power (direct or indirect) | Crawling Identified | Speed, Terrain, Elapsed Time, Time of Day, Location, Altitude, Movement Incidence, Force pf Movement, HR, R-R (HRV), ECG, BP, Respiration Rate, Body Temperature, Glucose & Cholesterol Levels, Pulse Oximetry, Steps, Gait Analysis |
| Specialist: Climbing | Speed (GPS, Acclerometer, indoor/mechanical) or Power | Altitude change (slope, gradient) AND Speed or Power | gradient >8 degrees (15%) gradient) >2 m, vertical gain gradient >8 degrees >70 secs, with 'edge forgiveness' (1-9 secs) <3 km/hr >power calc for 3 km/hr taking into account and slope | GPS, Barometer, DEM, Inclinometer | Hill Sprint Identified | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including |

TABLE 2-continued

Activity Status Monitoring - Health/Military/Personel - Walking/Running Classification System

| Classification of Activity Type | Primary Intensity measurement system | Metrics Used (Parameters) | Algorithm | Measurement Sensor/s | Example of Output | Edge Forgiveness is a period where Activity Type can 'drop out' of zone without ending the Identification Period for that Activity Type Collected Raw Data over the Identified Activity Period |
|---|---|---|---|---|---|---|
| Specialist: Descending | Speed (GPS, Accelerometer, indoor/mechanical) or Power | Altitude change (slope, gradient) AND Speed or or Power | gradient >~8 degrees (~15% gradient) >2 m, vertical loss gradient >~8 degrees > 70 secs, with 'edge forgiveness' (1-9 sec) >0 km/hr >power calc for 0 km/hr taking into account and slope | GPS, Barometer, DEM, Inclinometer | Hill Sprint Identified | GPS Altitude would require error correction. information on their Activities), Location of Resources, Goal Target, Mission Objectives Direction to User is Facing, Forwards vs Backwards vs Lateral Movement (left and right) Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| Non Specific Movement - Moderate Intensity | Speed (GPS, Accelerometer, indoor/mechanical) or Power | Speed AND Stride Rate: AND Postural Status | 2-6 km/hr 5-40 impacts/strides per min, Time Uniformity >40 ms Upright >45% and <55% of AT HR (>37% and <60% of | GPS or Accelerometer Accelerometer Accelerometer | Non Specific Movement Moderate Intensity Identified Non Specific | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) Speed, Terrain, Elapsed Time, Time of Day, Location, Altitude, Movement Incidence, Force pf Movement, |

TABLE 2-continued

Activity Status Monitoring - Health/Military/Personel - Walking/Running Classification System

| Classification of Activity Type | Primary Intensity measurement system | Metrics | Used (Parameters) | Algorithm | Measurement Sensor/s GPS Speed would need smoothing. | Example of Output | Edge Forgiveness is a period where Activity Type can 'drop out' of zone without ending the Identification Period for that Activity Type |
|---|---|---|---|---|---|---|---|
| | | | | also Historic Averages, and Calibration | GPS Altitude would require error correction. | | Collected Raw Data over the Identified Activity Period |
| | Heart Rate | Heart Rate | | Maximum Heart Rate) | Heart Rate | Movement Moderate Intensity Identified | Turnover, Distance per Turnover HR, R-R (HRV), ECG, BP, Respiration Rate, Body Temperature, Glucose & Cholesterol Levels, Pulse Oximetry, Steps, Gait Analysis |
| | | AND | | 5-40 impacts/strides per min, Time Uniformity >40 ms | Accelerometer | | Heaviness of Footfall, L-R Power Balance, Force Measures for Gait, Environmental Gas Concentrations, |
| | | Stride Rate: AND Postural Status | | Upright | Accelerometer | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| Non Specific Movement - High Intensity | Speed (GPS, Accelerometer, indoor/mechanical) or Power | Speed | | 2-6 km/hr | GPS or Accelerometer | Non Specific Movement High Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | AND | | 40-60 impacts/strides per min, Time Uniformity >40 ms | Accelerometer | | Heaviness of Footfall, L-R Power Balance, Force Measures for Gait, Environmental Gas Concentrations, |
| | | Stride Rate: AND Postural Status | | Upright | Accelerometer | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | Heart Rate | Heart Rate | | >55% and <70% of AT HR (>55% and <65% of Maximum Heart Rate) | Heart Rate | Non Specific Movement Moderate Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | AND | | 40-60 impacts/strides per | | High Intensity | Heaviness of Footfall, L-R Power Balance, Force Measures for Gait, Environmental Gas |

TABLE 2-continued

Activity Status Monitoring - Health/Military/Personel - Walking/Running Classification System

| Classification of Activity Type | Primary Intensity measurement system | Metrics | Used (Parameters) | Algorithm | Measurement Sensor/s GPS Speed would need smoothing. | Example of Output | Edge Forgiveness is a period where Activity Type can 'drop out' of zone without ending the Identification Period for that Activity Type Collected Raw Data over the Identified Activity Period |
|---|---|---|---|---|---|---|---|
| | | | Stride Rate: AND Postural Status | min, Time Uniformity >40 ms Upright | GPS Altitude would require error correction. Accelerometer | Identified | Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| Non Specific Movement - Very High Intensity | Speed (GPS, Acclerometer, indoor/mechanical) or Power | Speed | | 2-6 km/hr | GPS or Accelerometer | Non Specific Movement Very High Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, |
| | | | AND Stride Rate: AND Postural Status | 60+ impacts/strides per min, Time Uniformity >40 ms Upright | Accelerometer Accelerometer | | Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | Heart Rate | Heart Rate | | >70% of AT HR (>65% of Maximum Heart Rate) | Heart Rate | Non Specific Movement Very High Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force |
| | | | AND | 60+ impacts/strides per min, | | | |

TABLE 2-continued

Activity Status Monitoring - Health/Military/Personel - Walking/Running Classification System

| Classification of Activity Type | Primary Intensity measurement system | Metrics | Used (Parameters) | Algorithm | Measurement Sensor/s | Edge Forgiveness is a period where Activity Type can 'drop out' of zone without ending the Identification Period for that Activity Type | Example of Output |
|---|---|---|---|---|---|---|---|
| | | | | also Historic Averages, and Calibration | GPS Speed would need smoothing. | GPS Altitude would require error correction. | Collected Raw Data over the Identified Activity Period |
| | | | Stride Rate: AND Postural Status | Time Uniformity >40 ms | Accelerometer | | Measures for Gait, Environmental Gas Concentrations, Environmental Temp, Heat Index, Wind Chill, Altitude, Slope/Gradient, Wind Speed, Weather (rain etc), Distance, Location of an object or incident Weather Forecast, Location of other Users (including information on their Activities), Location of Resources, Goal Target, Mission Objectives Direction to User is Facing, Forwards vs Backwards vs Lateral Movement (left and right) |
| | | | | Upright | Accelerometer | | |

TABLE 3

Running Classification

| Activity | Classfication of Activity Type | Running Classification System (Cross Country Skiing, Skating) | | | | Edge Forgiveness is a period where Activity Type can 'drop out' of zone without ending the Identification Period for that Activity Type | | |
|---|---|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | Example of Output | Collected Raw Data over the Identified Activity Period | |
| Stationary | Inactive | Speed or Power (GPS, Acclerometer, indoor/mechanical) | Speed or Power | Speed <2 km/hr for more than 15 sec<br>Power <25 w for more than 15 sec | GPS or Accelerometer<br>Power (direct or indirect) | Inactive Identified (Pause) | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, | |
| | | Heart Rate & Speed or Power | Heart Rate AND Speed or Power | >30% <70% of AT heart rate >30% <60% HR max<br>Speed <1 km/hr for more than 2 mins<br>Power <25 w for more than 15 sec | Heart Rate<br>GPS or Accelerometer<br>Power (direct or indirect) | Inactive Identified (Pause) | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, | |
| Running | Easy | | Altitude change (slope, gradient) | Slope <2 degrees (4% gradient) and >−2 degrees (−4%)<br>stop: gradient >2 degrees over 6 meters vertical gain<br>stop: gradient >2 degrees > | GPS, Barometer, DEM, Inclinometer | Easy Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force | |

TABLE 3-continued

Running Classification

| Activity | Classification of Activity Type | Running Classification System (Cross Country Skiing, Skating) | | | | Edge Forgiveness is a period where Activity Type can 'drop out' of zone without ending the Identification Period for that Activity Type | | |
|---|---|---|---|---|---|---|---|---|
| | | Primary Intensity measurement system | Metrics Used (Parameters) | Algorithm also Historic Averages, and Calibration | Measurement Sensor/s GPS Speed would need smoothing, GPS Altitude would require error correction. | Example of Output | Collected Raw Data over the Identified Activity Period | |
| | | Speed (GPS, Accelerometer, indoor/mechanical) or Power | AND | 30 secs with 'edge forgiveness' (1-9 secs) | | | Measures for Gait, Environmental Gas Concentrations, Environmental Temp, Heat Index, Wind Chill, Altitude, Slope/Gradient, Wind Speed, Weather (rain etc), Diestance Weather Forecast, Location of other Users (including information on their Activities), Direction to User is Facing, | |
| | | | Speed or | 65-90% of AT speed | GPS or Accelerometer | | | |
| | | | or Power Possible Extra Parameter: | 65-90% of AT Power | Power (direct or indirect) | | | |
| | | | Stride Rate: | >70 steps a min (1 full cycle L & R legs) Speed or Heart Rate equivilent to Intial Calibration of 6-7.5 of Max Effort via User Rating | Accelerometer | | | |
| | | | Altitude change (slope, gradient) | Slope <2 degrees (4% gradient) and >−2 degrees (−4%) stop: gradient >2 degrees over 6 meters vertical gain stop: gradient >2 degrees > 30 secs | GPS, Barometer, DEM, Inclinometer | Easy Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, | |
| | | Heart Rate | AND | with 'edge forgiveness' (1-9 secs) 70-80% of AT heart rate 60-75% HR max (AT HR - 10 bts & AT HR - 40 bts) | Heart Rate | | | |
| | | | Heart Rate Possible Extra Parameter: | | | | | |
| | | | Stride Rate: | >70 steps a min (1 full cycle L & R legs) Speed or Heart Rate equivlent to Intial Calibration of 6.5-7.5 of Max Effort via User Rating | Accelerometer | | | |
| Rolling Hills - Running | | | Altitude change (slope, | gradient >2 degrees (4% gradient) <8 degrees (15%) > | GPS, Barometer, DEM, | Rolling Hill | Speed, Terrain, Elapsed Time, Time of Day, Location, Altitude, Movement Incidence, Force pf Movement, Turnover, Distance per Turnover | |

TABLE 3-continued

Running Classification

| Activity | Classification of Activity Type | Running Classification System (Cross Country Skiing, Skating) | | | | Edge Forgiveness is a period where Activity Type can 'drop out' of zone without ending the Identification Period for that Activity Type | |
|---|---|---|---|---|---|---|---|
| | | Primary Intensity measurement system | Metrics Used (Parameters) | Algorithm also Historic Averages, and Calibration | Measurement Sensor/s GPS Speed would need | Example of Output | Collected Raw Data over the Identified Activity Period |
| | | | gradient) | 7 m, <20 m vertical gain gradient >2 degrees >70 secs, <200 secs with 'edge forgiveness' (1-9 secs) | smoothing, GPS Altitude would require error correction. Inclinometer | Identified | HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power | AND | >7 km/hr | | | |
| | | | Speed or or Power Possible Extra Parameter: | >power calc for 7 km/hr taking into account and slope | | | |
| Hills - Running | No Heart Rate | | Stride Rate: Altitude change (slope, gradient) | >70 steps a min (1 full cycle L & R legs) gradient >2 degrees (4%) gradient) <8 degrees (15%) > 20 m, <30 m vertical gain gradient >2 degrees >200 secs < 410 secs | GPS, Barometer, DEM, Inclinometer | Hill Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power | AND | with 'edge forgiveness' (1-9 secs) | | | |
| | | | Speed or or Power Possible Extra Parameter: | >7 km/hr >power calc for 7 km/hr taking into account and slope | | | |
| Long Climb - Running | No Heart Rate | | Stride Rate: Altitude change (slope, gradient) AND | >70 steps a min (1 full cycle L & R legs) gradient >2 degrees (4%) gradient) <8 degrees (15%) > 30 m vertical gain gradient >2 degrees >410 secs with 'edge forgiveness' (1-9 secs) | GPS, Barometer, DEM, Inclinometer | Long Climb Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |

TABLE 3-continued

Running Classification

| Activity | Classification of Activity Type | Running Classification System (Cross Country Skiing, Skating) | | | Edge Forgiveness is a period where Activity Type can 'drop out' of zone without ending the Identification Period for that Activity Type | | |
|---|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | Example of Output | Collected Raw Data over the Identified Activity Period |
| | | Speed (GPS, Accelerometer, indoor/mechanical) or Power | Speed or | >7 km/hr | | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | | | or Power Possible Extra Parameter: | >power calc for 7 km/hr taking into account and slope | | | |
| Hill Efforts | No Heart Rate | | Stride Rate: | >70 steps a min (1 full cycle L & R legs) | | | |
| | | | Altitude change (slope, gradient) | slope = 2-4 degrees (gradient = 4-7%) stop: slope >4 degrees (7%) stop: slope less than 2 degrees with 'edge forgiveness' (1-9 secs) | GPS, Barometer, DEM, Inclinometer | Hill Effort Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | | AND | 90-95% of AT speed (AT Speed - (AT Speed * 5%), AT Speed * 95% | GPS or Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | | Speed (GPS, Accelerometer, indoor/mechanical) or Power | or Power Possible Extra Parameter: | 95-105% of AT Power | Power (direct or indirect) | | |
| | Heart Rate | | Stride Rate: | >70 steps a min (1 full cycle L & R legs) Speed or Heart Rate equivalent to Intial Calibration of 7.5-8.5 of Max Effort via User Rating | Accelerometer | | |
| | | | Altitude change (slope, gradient) | slope = 2-4 degrees (gradient = 4-7%) stop: slope >4 degrees (7%) stop: slope less than 2 degrees with 'edge forgiveness' (1-9 secs) | GPS, Barometer, DEM, Inclinometer | Hill Effort Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force |
| | | | AND | | | | |

TABLE 3-continued

Running Classification

| Activity | Classification of Activity Type | Running Classification System (Cross Country Skiing, Skating) | | | Edge Forgiveness is a period where Activity Type can 'drop out' of zone without ending the Identification Period for that Activity Type | | |
|---|---|---|---|---|---|---|---|
| | | Primary Intensity measurement system | Metrics Used (Parameters) | Algorithm also Historic Averages, and Calibration | Measurement Sensor/s GPS Speed would need smoothing, GPS Altitude would require error correction. | Example of Output | Collected Raw Data over the Identified Activity Period |
| | | | Heart Rate Possible Extra Parameter: | 80-90% of AT heart rate 75-85% HR max (AT HR & AT HR - 10 bts) | Heart Rate | | Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing. |
| | | | Stride Rate: | >70 steps a min (1 full cycle L & R legs) Speed or Heart Rate equivilent to Intial Calibration of 6.5-7.5 of Max Effort via User Rating | Accelerometer | | |
| | Up Tempo | | Altitude change (slope, gradient) | Slope <2 degrees (4% gradient) and >-2 degrees (-4%) stop: gradient >2 degrees over 6 meters vertical gain stop: gradient >2 degrees > 30 secs with 'edge forgiveness' (1-9 secs) | GPS, Barometer, DEM, Inclinometer | Up Tempo Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | AND Speed (GPS, Accelerometer, indoor/mechanical) or Power | Speed or | 90-95% of AT speed | GPS or Accelerometer | | |
| | | | or Power Possible Extra Parameter: | 90-95% of AT Power | Power (direct or indirect) | | |
| | | | Stride Rate: | >70 steps a min (1 full cycle L & R legs) Speed or Heart Rate equivilent to Intial Calibration of 7.5-8.5 of Max Effort via User Rating | Accelerometer | | |
| | | | Altitude change (slope, gradient) | Slope <2 degrees (4% gradient) and >-2 degrees (-4%) | GPS, Barometer, DEM, Inclinometer | Up Tempo Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, |
| | | Heart Rate | | | | | |

TABLE 3-continued

Running Classification

| Activity | Classification of Activity Type | Running Classification System (Cross Country Skiing, Skating) | | | Measurement Sensor/s | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm also Historic Averages, and Calibration | | | Collected Raw Data over the Identified Activity Period |
| | | | | stop: gradient >2 degrees over 6 meters vertical gain stop: gradient >2 degrees > 30 secs | GPS Speed would need smoothing, GPS Altitude would require error correction. | | Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | AND | with 'edge forgiveness' (1-9 secs) 80-90% of AT heart rate 75-85% | | | |
| | | | Heart Rate Possible Extra Parameter: | HR max (AT HR & AT HR - 10 bts) | Heart Rate | | |
| | | | Stride Rate: | >70 steps a min (1 full cycle L & R legs) Speed or Heart Rate equivilent to Intial Calibration of 7.5-8.5 of Max Effort via User Rating | Accelerometer | | |
| Anaerobic Threshold | | Speed (GPS, Accelerometer, indoor/mechanical) or Power | Altitude change (slope, gradient) | Slope <2 degrees (4% gradient) and >−2 degrees (−4%) stop: gradient >2 degrees over 6 meters vertical gain stop: gradient >2 degrees > 30 secs | GPS, Barometer, DEM, Inclinometer | Anaerobic Threshold Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | AND | with 'edge forgiveness' (1-9 secs) | | | |
| | | | Speed or | 95-105% of AT speed | GPS or Accelerometer | | |
| | | | or Power Possible Extra Parameter: | 95-105% of AT Power | Power (direct or indirect) | | |
| | | | Stride Rate: | >70 steps a min (1 full cycle L & R legs) Speed or Heart Rate equivilent to Intial Calibration of 8.5-9.5 of Max Effort via User Rating | Accelerometer | | |

TABLE 3-continued

Running Classification

Running Classification System (Cross Country Skiing, Skating)

Edge Forgiveness is a period where Activity Type can 'drop out' of zone without ending the Identification Period for that Activity Type

| Activity | Classification of Activity Type | Primary Intensity measurement system | Metrics Used (Parameters) | Algorithm also Historic Averages, and Calibration | Measurement Sensor/s GPS Speed would need smoothing, GPS Altitude would require error correction. | Example of Output | Collected Raw Data over the Identified Activity Period |
|---|---|---|---|---|---|---|---|
| | | Heart Rate | Altitude change (slope, gradient) | Slope <2 degrees (4% gradient) and >−2 degrees (−4%) stop: gradient >2 degrees over 6 meters vertical gain stop: gradient >2 degrees > 30 secs | GPS, Barometer, DEM, Inclinometer | Anaerobic Threshold Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | AND | with 'edge forgiveness' (1-9 secs) 99-101% of AT heart rate 85-95% HR max (AT HR+ & −3 bts) | Heart Rate | | |
| | | | Heart Rate Possible Extra Parameter: Stride Rate: | >70 steps a min (1 full cycle L & R legs) Speed or Heart Rate equivilent to Initial Calibration of 8.5-9.5 of Max Effort via User Rating | Accelerometer | | |
| Sprint | | | Altitude change (slope, gradient) | Slope <2 degrees (4% gradient) and >−2 degrees (−4%) stop: gradient >2 degrees over 6 meters vertical gain stop: gradient >2 degrees > 30 secs | GPS, Barometer, DEM, Inclinometer | Sprint Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | AND | with 'edge forgiveness' (1-9 secs) | | | |
| | | Speed (GPS, Acclerometer, indoor/mechanical) or Power | Speed or or Power Possible Extra Parameter: | 105%-115% of AT speed 105%-115% of AT Power | GPS or Accelerometer Power (direct or indirect) | | |
| | | | | >70 steps a min (1 full cycle L | Accelerometer | | |

TABLE 3-continued

Running Classification

| Activity | Classfication of Activity Type | Running Classification System (Cross Country Skiing, Skating) | | | Edge Forgiveness is a period where Activity Type can 'drop out' of zone without ending the Identification Period for that Activity Type | | |
|---|---|---|---|---|---|---|---|
| | | Primary Intensity measurement system | Metrics Used (Parameters) | Algorithm also Historic Averages, and Calibration | Measurement Sensor/s GPS Speed would need smoothing, GPS Altitude would require error correction. | Example of Output | Collected Raw Data over the Identified Activity Period |
| | | | Stride Rate: | & R legs) Speed or Heart Rate equivilent to Intial Calibration of 8.5-9.5 of Max Effort via User Rating | | | |
| | | Heart Rate | Altitude change (slope, gradient) | Slope <2 degrees (4% gradient) and >-2 degrees (-4%) stop: gradient >2 degrees over 6 meters vertical gain stop: gradient >2 degrees > 30 secs | GPS, Barometer, DEM, Inclinometer | Sprint Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | AND Heart Rate Possible Extra Parameter: | with 'edge forgiveness' (1-9 secs) 101-103% of AT heart rate >95-98% HR max (AT HR +3 bts, AT HR +8 bts) | Heart Rate | | |
| | | | Stride Rate: | >70 steps a min (1 full cycle L & R legs) Speed or Heart Rate equivilent to Intial Calibration of 8.5-9.5 of Max Effort via User Rating | Accelerometer | | |
| Overspeed | | Heart Rate Weak to Classify this | Altitude change (slope, gradient) | Slope <<2 degrees (-4% gradient) and >-4 degrees (-7%) stop: gradient >-2 degrees over 15 secs, <-4 degrees over 15 secs with 'edge forgiveness' (1-9 secs) | GPS, Barometer, DEM, Inclinometer | Overspeed Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power | AND Speed or or Power | 100%-105% of AT speed 100%-105% of AT Power | GPS or Accelerometer Power (direct or indirect) | | |

TABLE 3-continued

Running Classification

Running Classification System (Cross Country Skiing, Skating)

Edge Forgiveness is a period where Activity Type can 'drop out' of zone without ending the Identification Period for that Activity Type

| Activity | Classification of Activity Type | Primary Intensity measurement system | Metrics Used (Parameters) | Algorithm also Historic Averages, and Calibration | Measurement Sensor/s GPS Speed would need smoothing. | Example of Output | Collected Raw Data over the Identified Activity Period |
|---|---|---|---|---|---|---|---|
| | | | Altitude change (slope, gradient) | Slope <-2 degrees (-4% gradient) and >-4 degrees (-7%) stop: gradient >-2 degrees over 15 secs, <-4 degrees over 15 secs with 'edge forgiveness' (1-9 secs) | GPS Altitude would require error correction. GPS, Barometer, DEM, Inclinometer | Overspeed Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Speed (GPS, Accelerometer, indoor/mechanical) or Power and Stride Rate | AND Speed or or Power AND Slide Rate: | 100%-105% of AT speed 100%-105% of AT Power >5% AT SR (1 full cycle L & R legs) | GPS or Accelerometer Power (direct or indirect) Accelerometer | | |

TABLE 4

Cycling Classification

Edge Forgiveness is a period where Activity Type can 'drop out' of zone without ending the Identification Period for that Activity Type

| Activity | Classification of Activity Type | Cycling Classification System | | | | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | Measurement Sensor/s GPS Speed would need smoothing. | | |
| Running | | | | | | | |
| Cycling | Inactive | Speed or Power (GPS, Accelerometer, indoor/mechanical) | Speed or | Speed <2 km/hr for more than 15 sec | GPS Altitude would require error correction. | Inactive Identified (Pause) | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | | or Power | Power <25 w for more than 15 sec | Power (direct or indirect) | | |
| | | Heart Rate & Speed or Power | Heart Rate | >30% <70% of AT heart rate >30% <60% HR max | Heart Rate | Inactive Identified (Pause) | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | AND | | | | | |
| | | | Speed or | Speed <1 km/hr for more than 15 secs | GPS or Accelerometer | | |
| | Easy | | or Power | Power <25 w for more than 15 sec | Power (direct or indirect) | Easy Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather |
| | | | Altitude change (slope, gradient) | Slope <2 degrees (4% gradient) and >−2 degrees (−4%) stop: gradient >2 degrees over 6 meters vertical gain stop: gradient >2 degrees >30 secs | GPS, Barometer, DEM, Inclinometer | | |

TABLE 4-continued

Cycling Classification

Edge Forgiveness is a period where Activity Type can 'drop out' of zone without ending the Identification Period for that Activity Type

| Activity | Classification of Activity Type | Cycling Classification System ||| Example of Output | Collected Raw Data over the Identified Activity Period |
|---|---|---|---|---|---|---|
| | | Primary Intensity measurement system | Metrics Used (Parameters) | Algorithm also Historic Averages, and Calibration | Measurement Sensor/s | |
| | | Speed (GPS Accelerometer, indoor/mechanical) or Power | AND | with 'edge forgiveness' (1-9 secs) | GPS Speed would need smoothing. | |
| | | | Speed or | 65-90% of AT speed | GPS Altitude would require error correction. | (rain etc), Distance |
| | | | or Power Possible Extra Parameter: | 65-90% of AT Power | GPS or Cycle Speed Sensor Power (direct or indirect) | |
| | | | Cadence | Road: 90-105 rpm, Triathlon, MTB, TT: 85-95 rpm, Recreational: 80-95 rpm Speed or Heart Rate equivilent to Initial Calibration of 6-7.5 of Max Effort via User Rating | Cycle Cadence Sensor | |
| | | | Altitude change (slope, gradient) | Slope <2 degrees (4% gradient) and >−2 degrees (−4%) stop: gradient >2 degrees over 6 meters vertical gain stop: gradient >2 degrees >30 secs | GPS, Barometer, DEM, Inclinometer | Easy Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, Environmental Temp, Heat Index, Wind Chill, Altitude, Slope/Gradient, Wind Speed, Weather (rain etc), Distance |
| | | Heart Rate | AND | with 'edge forgiveness' (1-9 secs) 70-80% of AT heart rate 65-75% HR max (AT HR −10 bts & AT HR −40 bts | | | |
| | | | Heart Rate Possible Extra Parameter: | | Heart Rate | | |
| | | | Cadence | Road: 90-105 rpm, Triathlon, MTB, TT: 85-95 rpm, Recreational: 80-95 rpm | Cycle Cadence Sensor | | |

TABLE 4-continued

Cycling Classification

| Activity | Classification of Activity Type | Cycling Classification System | | | | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | | Edge Forgiveness is a period where Activity Type can 'drop out' of zone without ending the Identification Period for that Activity Type |
| | Rolling Hills | No Primary Intensity (Altitude) | Altitude change (slope, gradient) | Speed or Heart Rate equivalent to Initial Calibration of 6-7.5 of Max Effort via User Rating<br><br>gradient >2 degrees (4% gradient) <8 degrees (15%) >7 m, <20 m vertical gain<br><br>gradient >2 degrees >70 secs, <200 secs<br><br>with 'edge forgiveness' (1-9 secs) | GPS, Barometer, DEM, Inclinometer | Rolling Hill Identified | Speed, Terrain, Elapsed Time, Time of Day, Location, Altitude, Turnover, Distance per Turnover<br>HR, R-R (HRV), ECG, BP, Respiration Rate, Body Temperature, Glucose & Cholesterol Levels, Pulse Oximetry,<br>L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | Hills | No Primary Intensity (Altitude) | Altitude change (slope, gradient) | gradient >2 degrees (4% gradient) <8 degrees (15%) >20 m, <30 m vertical gain<br><br>gradient >2 degrees >200 secs, <410 secs<br><br>with 'edge forgiveness' (1-9 secs) | GPS, Barometer, DEM, Inclinometer | Hill Identified | Speed, Terrain, Elapsed Time, Time of Day, Location, Altitude, Turnover, Distance per Turnover<br>HR, R-R (HRV), ECG, BP, Respiration Rate, Body Temperature, Glucose & Cholesterol Levels, Pulse Oximetry,<br>L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | Long Climb | No Primary Intensity (Altitude) | Altitude change (slope, gradient) | gradient >2 degrees (4% gradient) <8 degrees (15%) <30 m vertical gain<br><br>gradient >2 degrees <410 secs | GPS, Barometer, DEM, Inclinometer | Long Climb Identified | Speed, Terrain, Elapsed Time, Time of Day, Location, Altitude, Turnover, Distance per Turnover<br>HR, R-R (HRV), ECG, BP, Respiration Rate, Body Temperature, Glucose & Cholesterol Levels, Pulse Oximetry,<br>L-R Power Balance, Force Measures for Pedal Stroke (direct, Lateral, Vertical and tangental), |

TABLE 4-continued

Cycling Classification

| Activity | Classification of Activity Type | Cycling Classification System | | | Example of Output | Collected Raw Data over the Identified Activity Period |
|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | |
| | Hill Efforts | | Altitude change (slope, gradient) | with 'edge forgiveness' (1-9 secs) | | Environmental Gas Concentrations, Environmental Temp, Heat Index, Wind Chill, Altitude, Slope/Gradient, Wind Speed, Weather (rain etc), Distance |
| | | | | slope = 2-4 degrees (gradient = 4-7%) | GPS, Barometer, DEM, Inclinometer | Hill Effort Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, Environmental Temp, Heat Index, Wind Chill, Altitude, Slope/Gradient, Wind Speed, Weather (rain etc), Distance |
| | | | | stop: slope >4 degrees (7%) | | | |
| | | | | stop: slope less than 2 degrees | | | |
| | | Speed (GPS, Accelerometer, indoor/mechanical) or Power | AND | with 'edge forgiveness' (1-9 secs) | | | |
| | | | Speed or | 90-95% of AT speed (AT Speed − (AT Speed * 5%), AT Speed * 95% | GPS or Cycle Speed Sensor Power (direct or indirect) | | |
| | | | or Power Possible Extra Parameter: | 95-105% of AT Power | | | |
| | | | Cadence | Road: 90-105 rpm, Triathlon, MTB, TT: 85-95 rpm, Recreational: 80-95 rpm Speed or Heart Rate equivlent to Intial Calibration of 7.5-8.5 of Max Effort via User Rating | Cycle Cadence Sensor | | |
| | Heart Rate | | Altitude change (slope, gradient) AND | slope = 2-4 degrees (gradient = 4-7%) stop: slope >4 degrees (7%) stop: slope less than 2 degrees with 'edge forgiveness' (1-9 secs) 80-90% of AT heart rate 75-85% | GPS, Barometer, DEM, Inclinometer Heart Rate | Hill Effort Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, |

TABLE 4-continued

Cycling Classification

Edge Forgiveness is a period where Activity Type can 'drop out' of zone without ending the Identification Period for that Activity Type

| Activity | Classification of Activity Type | Cycling Classification System ||| Measurement Sensor/s GPS Speed would need smoothing. | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | | | |
| | | | | HR max (AT HR & AT HR −10 bts) | GPS Altitude would require error correction. | | L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | | Heart Rate Possible Extra Parameter: | | | | |
| | | | Cadence | Road: 90-105 rpm, Triathlon, MTB, TT: 85-95 rpm, Recreational: 80-95 rpm Speed or Heart Rate equivilent to Intial Calibration of 7.5-8.5 of Max Effort via User Rating | Cycle Cadence Sensor | | |
| | Flat Big Gear | | Altitude change (slope, gradient) | Slope <2 degrees (4% gradient) and >−2 degrees (−4%) stop: gradient >2 degrees over 6 meters vertical gain stop: gradient >2 degrees >30 secs | GPS, Barometer, DEM, Inclinometer | Flat Big Gear Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | | AND | with 'edge forgiveness' (1-9 secs) | | | |
| | | Speed (GPS, Aclerometer, indoor/mechanical or Power | Speed or | 65-90% of AT speed | GPS or Cycle Speed Sensor Power (direct or indirect) | | |
| | | | or Power AND | 65-90% of AT Power | | | |
| | | | | Road: 90-105 rpm, Triathlon, MTB, TT: 85-95 rpm, | Cycle Cadence | | |

TABLE 4-continued

Cycling Classification

Edge Forgiveness is a period where Activity Type can 'drop out' of zone without ending the Identification Period for that Activity Type

| Activity | Classification of Activity Type | Cycling Classification System | | | Example of Output | Collected Raw Data over the Identified Activity Period |
|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | |
| | | | Cadence or Distance per Pedal Revolution | Recreational: 80-95 rpm | Sensor GPS or Cycle Speed & Cadence Sensor | |
| | | | | 85-130% of AT Distance per Pedal Revolution Speed or Heart Rate equivilent to Intial Calibration of 6-7.5 of Max Effort via User Rating | | |
| | | | Altitude change (slope, gradient) | Slope <2 degrees (4% gradient) and >-2 degrees (-4%) | GPS, Barometer, DEM, Inclinometer | Flat Big Gear Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, Environmental Temp, Heat Index, Wind Chill, Altitude, Slope/Gradient, Wind Speed, Weather (rain etc), Distance |
| | | | | stop: gradient >2 degrees over 6 meters vertical gain | | | |
| | | | | stop: gradient >2 degrees >30 secs | | | |
| | | | AND | with 'edge forgiveness' (1-9 secs) 70-80% of AT heart rate 65-75% HR max (AT HR −10 bts & AT HR −40 bts) | Heart Rate | | |
| | | Heart Rate | Heart Rate AND | Road: 90-105 rpm, Triathlon, MTB, TT: 85-95 rpm, Recreational: 80-95 rpm | Cycle Cadence Sensor GPS or Cycle Speed & Cadence Sensor | | |
| | | | Cadence or Distance per Pedal Revolution | 85-130% of AT Distance per Pedal Revolution Speed or Heart Rate equivilent to Intial Calibration of 6-7.5 of Max Effort via User Rating | | | |
| | Big Gear Time Trial | | Altitude change (slope, gradient) | Slope <2 degrees (4% gradient) and >-2 degrees (-4%) | GPS, Barometer, DEM, Inclinometer | Big Gear Time Trial Identified | Speed, Terrain, Elapsed Time, Time of Day, Location, Altitude, Turnover, Distance per Turnover HR, R-R (HRV), ECG, BP, Respiration Rate, |

TABLE 4-continued

Cycling Classification

| Activity | Classification of Activity Type | Cycling Classification System | | | | | |
|---|---|---|---|---|---|---|---|
| | | Primary Intensity measurement system | Metrics Used (Parameters) | Algorithm also Historic Averages, and Calibration | Measurement Sensor/s GPS Speed would need smoothing. GPS Altitude would require error correction. | Example of Output | Collected Raw Data over the Identified Activity Period Edge Forgiveness is a period where Activity Type can 'drop out' of zone without ending the Identification Period for that Activity Type |
| | | | | stop: gradient >2 degrees over 6 meters vertical gain | | | Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | | | stop: gradient >2 degrees >30 secs | | | |
| | | | AND | with 'edge forgiveness' (1-9 secs) | | | |
| | | Speed (GPS, Aclerometer, indoor/mechanical or Power | Speed or | 90-105% of AT speed | GPS or Cycle Speed Sensor | | |
| | | | or Power AND | 90-120% of AT Power | Power (direct or indirect) | | |
| | | | Cadence or or Distance per Pedal Revolution | Road: 90-105 rpm, Triathlon, MTB, TT: 85-95 rpm, Recreational: 80-95 rpm | Cycle Cadence Sensor GPS or Cycle Speed & Cadence Sensor | | |
| | | | | 100-130% of AT Distance per Pedal Revolution | | | |
| | | | | Speed or Heart Rate equivilent to Intial Calibration of 7.5-8.5 of Max Effort via User Rating | | | |
| | | | Altitude change (slope, gradient) | Slope <2 degrees (4% gradient) and >-2 degrees (-4%) | GPS, Barometer, DEM, Inclinometer | Big Gear Time Trial Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Environmental Gas Concentrations, Environmental Temp, Heat Index, Wind Chill, Altitude, Slope/Gradient, Wind Speed, Weather (rain etc), Distance |
| | | | | stop: gradient >2 degrees over 6 meters vertical gain | | | |
| | | | | stop: gradient >2 degrees >30 secs | | | |
| | | | AND | with 'edge forgiveness' (1-9 secs) 80-90% of AT heart rate 75-85% | | | |

TABLE 4-continued

Cycling Classification

| Activity | Classification of Activity Type | Cycling Classification System ||||| Example of Output | Collected Raw Data over the Identified Activity Period |
|---|---|---|---|---|---|---|---|---|
| | | Primary Intensity measurement system | Metrics Used (Parameters) | Algorithm also Historic Averages, and Calibration | | Measurement Sensor/s | | |
| | | | | | | Edge Forgiveness is a period where Activity Type can 'drop out' of zone without ending the Identification Period for that Activity Type | | |
| | Up Tempo | Heart Rate | Heart Rate AND | HR max (AT HR & AT HR −10 bts | | Heart Rate | Up Tempo Identified | Speed, Terrain, Elapsed Time, Time of Day, Location, Altitude, Turnover, Distance per Turnover |
| | | | Cadence or or Distance per Pedal Revolution | Road: 90-105 rpm, Triathlon, MTB, TT: 85-95 rpm, Recreational: 80-95 rpm 100-130% of AT Distance per Pedal Revolution | | Cycle Cadence Sensor GPS or Cycle Speed & Cadence Sensor | | HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, |
| | | | Altitude change (slope, gradient) | Slope <2 degrees (4% gradient) and >−2 degrees (−4%) stop: gradient >2 degrees over 6 meters vertical gain stop: gradient >2 degrees >30 secs | | GPS, Barometer, DEM, Inclinometer | | Enviromental Temp, Heat Index, Wind Chill, Altitude, Slope/Gradient, Wind Speed, Weather (rain etc), Distance |
| | | | AND | with 'edge forgiveness' (1-9 secs) | | | | |
| | | Speed (GPS, Accelerometer, indoor/mechanical) or Power | Speed or | 90-95% of AT speed | | GPS or Cycle Speed Sensor | | |
| | | | or Power Possible Extra Parameter: | 90-95% of AT Power | | Power (direct or indirect) | | |
| | | | Cadence | Road: 90-105 rpm, Triathlon, MTB, TT: 85-95 rpm, Recreational: 80-95 rpm Speed or Heart Rate equivilent to Intial Calibration of 7.5-8.5 of Max Effort via User Rating | | Cycle Cadence Sensor | | |
| | | | Altitude | | | GPS, | | |

TABLE 4-continued

Cycling Classification

Edge Forgiveness is a period where Activity Type can 'drop out' of zone without ending the Identification Period for that Activity Type

| Activity | Classification of Activity Type | Cycling Classification System | | | | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | Measurement Sensor/s GPS Speed would need smoothing. | | |
| | | | Altitude change (slope, gradient) | Slope <2 degrees (4% gradient) and >−2 degrees (−4%) | GPS Altitude would require error correction. | Up Tempo Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, Environmental Temp, Heat Index, Wind Chill, Altitude, Slope/Gradient, Wind Speed, Weather (rain etc), Distance |
| | | | | stop: gradient >2 degrees over 6 meters vertical gain | Barometer, DEM, Inclinometer | | |
| | | | | stop: gradient >2 degrees >30 secs | | | |
| | | | AND | with 'edge forgiveness' (1-9 secs) 93-99% of AT heart rate 75-85% HR max (AT HR & AT HR −10 bts) | Heart Rate | | |
| | | Heart Rate | Heart Rate Possible Extra Parameter: | | | | |
| | | | Cadence | Road: 90-105 rpm, Triathlon, MTB, TT: 85-95 rpm, Recreational: 80-95 rpm Speed or Heart Rate equivilent to Intial Calibration of 7.5-8.5 of Max Effort via User Rating | Cycle Cadence Sensor | | |
| | Anaerobic Threshold | | Altitude change (slope, gradient) | Slope <2 degrees (4% gradient) and >−2 degrees (−4%) | GPS, Barometer, DEM, Inclinometer | Anaerobic Threshold Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Environmental Gas Concentrations, Environmental Temp, Heat Index, Wind Chill, Altitude, Slope/Gradient, Wind Speed, Weather |
| | | | | stop: gradient >2 degrees over 6 meters vertical gain | | | |
| | | | | stop: gradient >2 degrees >30 secs | | | |

TABLE 4-continued

Cycling Classification

| Activity | Classification of Activity Type | Cycling Classification System | | | | |
|---|---|---|---|---|---|---|
| | | Primary Intensity measurement system | Metrics Used (Parameters) | Algorithm also Historic Averages, and Calibration | Measurement Sensor/s GPS Speed would need smoothing. | Example of Output | Collected Raw Data over the Identified Activity Period |

Edge Forgiveness is a period where Activity Type can 'drop out' of zone without ending the Identification Period for that Activity Type

| | | | | | | | |
|---|---|---|---|---|---|---|---|
| | | Speed (GPS, Accelerometer, indoor/mechanical) or Power | AND | with 'edge forgiveness' (1-9 secs) | | | (rain etc), Distance |
| | | | Speed or | 95-105% of AT speed | GPS or Cycle Speed Sensor | | |
| | | | or Power Possible Extra Parameter: | 95-105% of AT Power | Power (direct or indirect) | | |
| | | | Cadence | Road: 90-105 rpm, Triathlon, MTB, TT: 85-95 rpm, Recreational: 80-95 rpm Speed or Heart Rate equivilent to Intial Calibration of 8.5-9.5 of Max Effort via User Rating | Cycle Cadence Sensor | | |
| | | | Altitude change (slope, gradient) | Slope <2 degrees (4% gradient) and >−2 degrees (−4%) stop: gradient >2 degrees over 6 meters vertical gain stop: gradient >2 degrees >30 secs | GPS, Barometer, DEM, Inclinometer | Anaerobic Threshold Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), Enviromental Gas Concentrations, Environmental Temp, Heat Index, Wind Chill, Altitude, Slope/Gradient, Wind Speed, Weather (rain etc), Distance |
| | | Heart Rate | AND | with 'edge forgiveness' (1-9 secs) 99-101% of AT heart rate 85-95% | | | |
| | | | Heart Rate Possible Extra Parameter: | HR max (AT HR + & −3 bts) | Heart Rate | | |
| | | | Cadence | Road: 90-105 rpm, Triathlon, MTB, TT: 85-95 rpm, Recreational: 80-95 rpm Speed or Heart Rate equivilent to | Cycle Cadence Sensor | | |

TABLE 4-continued

Cycling Classification

| Activity | Cycling Classification System | | | | | |
|---|---|---|---|---|---|---|
| Classification of Activity Type | Primary Intensity measurement system | Metrics Used (Parameters) | Algorithm also Historic Averages, and Calibration | Measurement Sensor/s GPS Speed would need smoothing. GPS Altitude would require error correction. | Example of Output | Collected Raw Data over the Identified Activity Period — Edge Forgiveness is a period where Activity Type can 'drop out' of zone without ending the Identification Period for that Activity Type |
| Power |  | Altitude change (slope, gradient) | Initial Calibration of 8.5-9.5 of Max Effort via User Rating | GPS, Barometer, DEM, Inclinometer | Power Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Enviromental Gas Concentrations, Enviromental Temp, Heat Index, Wind Chill, Altitude, Slope/Gradient, Wind Speed, Weather (rain etc), Distance |
|  |  |  | Slope <2 degrees (4% gradient) and >-2 degrees (-4%) |  |  |  |
|  |  |  | stop: gradient >2 degrees over 6 meters vertical gain |  |  |  |
|  |  |  | stop: gradient >2 degrees >30 secs |  |  |  |
|  | Speed (GPS, Accelerometer, indoor/mechanical) or Power | AND | with 'edge forgiveness' (1-9 secs) |  |  |  |
|  |  | Speed or or Power AND | from 20 km/hr to AT speed in less than 20 secs 50% to 133% of AT Power in under 20 secs | GPS or Cycle Speed Sensor Power (direct or indirect) |  |  |
|  |  | Cadence | 70-95 rpm in under 20 secs Speed or Heart Rate equivilent to Initial Calibration of >9 of Max Effort via User Rating | Cycle Cadence Sensor |  |  |
|  |  | Altitude change (slope, gradient) | Slope <2 degrees (4% gradient) and >-2 degrees (-4%) | GPS, Barometer, DEM, Inclinometer | Power Identified | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Enviromental Gas Concentrations, Enviromental Temp, Heat Index, Wind Chill, |
|  |  |  | stop: gradient >2 degrees over 6 meters vertical gain |  |  |  |
|  |  |  | stop: gradient >2 degrees >30 secs |  |  |  |

TABLE 4-continued

Cycling Classification

| Activity | Classification of Activity Type | Cycling Classification System ||| Example of Output | Collected Raw Data over the Identified Activity Period |
|---|---|---|---|---|---|---|
| | | Primary Intensity measurement system | Metrics Used (Parameters) | Algorithm also Historic Averages, and Calibration | Measurement Sensor/s | Edge Forgiveness is a period where Activity Type can 'drop out' of zone without ending the Identification Period for that Activity Type |
| | | | AND | with 'edge forgiveness' (1-9 secs) Heart Rate change >15% of AT | GPS Speed would need smoothing. | Altitude, Slope/Gradient, Wind Speed, Weather (rain etc), Distance |
| | | Heart Rate | Heart Rate AND | Heart Rate <20 secs | Heart Rate | |
| | | | Cadence | 70-95 rpm in under 20 secs Speed or Heart Rate equivlent to Intial Calibration of >9 of Max Effort via User Rating | Cycle Cadence Sensor | |
| | Sprint | | Altitude change (slope, gradient) | Slope <2 degrees (4% gradient) and >−2 degrees (−4%) stop: gradient >2 degrees over 6 meters vertical gain stop: gradient >2 degrees >30 secs | GPS, Barometer, DEM, Inclinometer | Sprint Identified |
| | | | AND | with 'edge forgiveness' (1-9 secs) | | Speed, Terrain, Elapsed Time, Time of Day, Location, Altitude, Turnover, Distance per Turnover HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangental), Enviromental Gas Concentrations, Enviromental Temp, Heat Index, Wind Chill, Altitude, Slope/Gradient, Wind Speed, Weather (rain etc), Distance |
| | | Speed (GPS, Acclerometer, indoor/mechanical) or Power | Speed or | >106% of AT speed | GPS or Cycle Speed Sensor | |
| | | | or Power Possible Extra Parameter: | >133% of AT Power | Power (direct or indirect) | |
| | | | Cadence | Road: 90-105 rpm, Triathlon, MTB, TT: 85-95 rpm, Recreational: 80-95 rpm Speed or Heart Rate equivlent to Intial Calibration of >9.5 of Max Effort via User Rating | Cycle Cadence Sensor | |

TABLE 4-continued

Cycling Classification

| Activity | Classification of Activity Type | Cycling Classification System ||| Measurement Sensor/s GPS Speed would need smoothing. | Example of Output | Collected Raw Data over the Identified Activity Period Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm also Historic Averages, and Calibration | | | |
| | | | Altitude change (slope, gradient) | Slope <2 degrees (4% gradient) and >−2 degrees (−4%) | GPS, Barometer, DEM, Inclinometer | Sprint Identified | Speed, Terrain, Elapsed Time, Time of Day, Location, Altitude, Turnover, Distance per Turnover |
| | | | | stop: gradient >2 degrees over 6 meters vertical gain | GPS Altitude would require error correction. | | HR, R-R (HRV), ECG, BP, Respiration Rate, Body Temperature, Glucose & Cholesterol Levels, Pulse Oximetry, |
| | | | | stop: gradient >2 degrees >30 secs | | | L-R Power Balance, Force Measures for Pedal Stroke (direct, Lateral, Vertical and tangential), Environmental Gas Concentrations, |
| | | | AND | with 'edge forgiveness' (1-9 secs) >101% of AT heart rate >95% HR max (AT HR +3 bts, AT HR +8 bts) | | | Altitude, Slope/Gradient, Wind Speed, Weather (rain etc), Distance |
| | | Heart Rate | Heart Rate Possible Extra Parameter: | Road: 90-105 rpm, Triathlon, MTB, TT: 85-95 rpm, Recreational: 80-95 rpm | Heart Rate | | Environmental Temp, Heat Index, Wind Chill, |
| | | | Cadence | Speed or Heart Rate equivlent to Initial Calibration of >9.5 of Max Effort via User Rating | Cycle Cadence Sensor | | |
| | Overspeed | | Altitude change (slope, gradient) | Slope <−2 degrees (−4% gradient) and >−4 degrees (−7%) | GPS, Barometer, DEM, Inclinometer | Overspeed Identified | Speed, Terrain, Elapsed Time, Time of Day, Location, Altitude, Turnover, Distance per Turnover |
| | | | | stop: gradient >−2 degrees over 15 secs, <−4 degrees over 15 secs | | | HR, R-R (HRV), ECG, BP, Respiration Rate, Body Temperature, Glucose & Cholesterol Levels, Pulse Oximetry, L-R Power Balance, Force Measures for Pedal Stroke (direct, Lateral, Vertical and tangential), |
| | | | | with 'edge forgiveness' (1-9 secs) | | | Environmental Gas Concentrations, |

TABLE 4-continued

Cycling Classification

| Activity | Classification of Activity Type | Cycling Classification System | | | |
|---|---|---|---|---|---|
| | | Primary Intensity measurement system | Metrics Used (Parameters) | Algorithm also Historic Averages, and Calibration | Measurement Sensor/s |
| | | Speed (GPS, Accelerometer, indoor/mechanical) or Power AND Cadence | | Road: >111 rpm, Triathlon, MTB, TT: >111 rpm, Recreational: >111 rpm | GPS Speed would need smoothing. GPS Altitude would require error correction. Cycle Cadence Sensor |

| | Example of Output | Edge Forgiveness is a period where Activity Type can 'drop out' of zone without ending the Identification Period for that Activity Type |
|---|---|---|
| | | Collected Raw Data over the Identified Activity Period |
| | | Environmental Temp, Heat Index, Wind Chill, Altitude, Slope/Gradient, Wind Speed, Weather (rain etc), Distance |

TABLE 5

Rowing/Kayaking Classification

Edge Forgiveness is a period where Activity Type can 'drop out' of zone without ending the Identification Period for that Activity Type

| Activity | Classification of Activity Type | Rowing/Kayaking Classification System | | | Measurement Sensor/s | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | GPS Speed would need smoothing. | | |
| Rowing | Inactive | Speed or Power (GPS, Accelerometer, indoor/mechanical) | Speed or | Speed <2 km/hr for more than 15 sec | GPS or Accelerometer | Inactive Identified (Pause) | Speed, Elapsed Time, Time of Day, Location, Altitude, Force of Movement, Turnover, Distance per Turnover |
| | | | Power | Power <25 w for more than 15 sec | Power (direct or indirect): | | HR, R-R (HRV), ECG, BP, Respiration Rate, Body Temperature, Glucose & Cholesterol Levels, Pulse Oximetry, Strokes |
| | | | | | | | Environmental Temp, (water temp) Heat Index, Wind Chill, Altitude, Power Curve, Wind Speed, Weather (rain etc), Distance |
| | | Heart Rate & Speed or Power | Heart Rate | <45% of AT heart rate <45% HR max | Heart Rate | Inactive Identified (Pause) | Speed, Elapsed Time, Time of Day, Location, Altitude, Force of Movement, Turnover, Distance per Turnover |
| | | | AND | | | | HR, R-R (HRV), ECG, BP, Respiration Rate, Body Temperature, Glucose & Cholesterol Levels, Pulse Oximetry, Strokes |
| | | | Speed or | Speed <1 km/hr for more than 2 mins | GPS or Accelerometer | | Environmental Temp, (water temp) Heat Index, Wind Chill, Altitude, Power Curve, Wind Speed, Weather (rain etc), Distance |
| | | | Power | Power <25 w for more than 15 sec | Power (direct or indirect) | | |
| | Easy | Speed (GPS, Rowing/Kayak Speed device, indoor/mechanical) | Stroke Rate | 18-22 strokes per min (crew number dependent | Stroke Rate Sensor | Easy Identified | Speed, Elapsed Time, Time of Day, Location, Altitude, Force of Movement, Turnover, Distance per Turnover |
| | | | AND | | Rowing/Kayak Speed Device, GPS | | HR, R-R (HRV), ECG, BP, Respiration Rate, Body Temperature, Glucose & Cholesterol Levels, Pulse Oximetry, Strokes |
| | | | Speed or | 65% to 90% of AT Speed | | | Environmental Temp, (water temp) Heat Index, Wind Chill, Altitude, Power Curve, Wind Speed, Weather (rain etc), Distance |
| | | | Power | 65% to 90% of AT Power Speed or Heart Rate equivalent to Initial Calibration of 6-7.5 of Max Effort via User Rating | | | |

TABLE 5-continued

Rowing/Kayaking Classification

| Activity | Classification of Activity Type | Rowing/Kayaking Classification System | | | Measurement Sensor/s | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | | | |
| | | Speed (GPS, Rowing/Kayak Speed device, indoor/mechanical) | Stroke Rate | 18-22 strokes per min (crew number dependent) | GPS Speed would need smoothing. Stroke Rate Sensor | Easy Identified | Speed, Elapsed Time, Time of Day, Location, Altitude, Force of Movement, Turnover, Distance per Turnover |
| | | | AND | | | | HR, R-R (HRV), ECG, BP, Respiration Rate, Body Temperature, Glucose & Cholesterol Levels, Pulse Oximetry, Strokes |
| | | | Heart Rate | 70 to 80% of AT heart rate or 65-75% HR max (AT HR −10 bts & AT HR −40 bts) Speed or Heart Rate equivilent to Intial Calibration of 6-7.5 of Max Effort via User Rating | Heart Rate | | Environmental Temp, (water temp) Heat Index, Wind Chill, Altitude, Power Curve, Wind Speed, Weather (rain etc), Distance |
| | Slow Full Pressure | Speed (GPS, Rowing/Kayak Speed device, indoor/mechanical) | Stroke Rate | 18-22 strokes per min (crew number dependent) | Stroke Rate Sensor | Slow Full Pressure Identified | Speed, Elapsed Time, Time of Day, Location, Altitude, Force of Movement, Turnover, Distance per Turnover |
| | | | AND | | | | HR, R-R (HRV), ECG, BP, Respiration Rate, Body Temperature, Glucose & Cholesterol Levels, Pulse Oximetry, Strokes |
| | | | Speed or Power | 80% to 93% of AT Speed 80% to 93% of AT Power Speed or Heart Rate equivilent to Intial Calibration of 7-8 of Max Effort via User Rating | Rowing/Kayak Speed Device, GPS | | Environmental Temp, (water temp) Heat Index, Wind Chill, Altitude, Power Curve, Wind Speed, Weather (rain etc), Distance |
| | | Speed (GPS, Rowing/Kayak Speed device, indoor/mechanical) | Stroke Rate | 18-22 strokes per min (crew number dependent) | Stroke Rate Sensor | Slow Full Pressure Identified | Speed, Elapsed Time, Time of Day, Location, Altitude, Force of Movement, Turnover, Distance per Turnover |
| | | | AND | | | | HR, R-R (HRV), ECG, BP, Respiration Rate, Body Temperature, Glucose & Cholesterol Levels, Pulse Oximetry, Strokes |
| | | | Heart Rate | 70 to 80% of AT heart rate or 65-75% HR max (AT HR −10 bts & AT HR −40 bts) Speed or Heart Rate equivilent to Intial Calibration of 7-8 of Max | Heart Rate | | Environmental Temp, (water temp) Heat Index, Wind Chill, Altitude, Power Curve, Wind Speed, Weather (rain etc), Distance |

Edge Forgiveness is a period where Activity Type can 'drop out' of zone without ending the Identification Period for that Activity Type TABLE 5-continued Rowing/Kayaking Classification

| Activity | Classification of Activity Type | Rowing/Kayaking Classification System | | | | Measurement Sensor/s GPS Speed would need smoothing. | Example of Output | Collected Raw Data over the Identified Activity Period |
|---|---|---|---|---|---|---|---|---|
| | | Primary Intensity measurement system | Metrics Used (Parameters) | | Algorithm also Historic Averages, and Calibration | | | |
| | Tempo Load | Speed (GPS, Rowing/Kayak Speed device, indoor/mechanical) | Stroke Rate | AND | 18-22 strokes per min (crew number dependent) Effort via User Rating | Stroke Rate Sensor | Tempo Load Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | Speed or Power | | 90% to 93% of AT Speed 90% to 103% of AT Power Speed or Heart Rate equivalent to Intial Calibration of 7.5-8.5 of Max Effort via User Rating | Rowing/Kayak Speed Device, GPS | | |
| | | Speed (GPS, Rowing/Kayak Speed device, indoor/mechanical) | Stroke Rate | AND | 18-22 strokes per min (crew number dependent) | Stroke Rate Sensor | Tempo Load Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | Heart Rate | | 80 to 90% of AT heart rate or 75-85% HR max (AT HR & AT HR −10 bts) Speed or Heart Rate equivalent to Intial Calibration of 7.5-8.5 of Max Effort via User Rating | Heart Rate | | |
| | Up Tempo | Speed (GPS, Rowing/Kayak Speed device, indoor/mechanical) | Stroke Rate | AND | 23-32 strokes per min (crew number dependent) | Stroke Rate Sensor | Up Tempo Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | Speed or or Power | | 90% to 93% of AT Speed 90% to 93% of AT Power Speed or Heart Rate equivalent to Intial Calibration of 7.5-8.5 of Max | Rowing/Kayak Speed Device, GPS | | |

Edge Forgiveness is a period where Activity Type can 'drop out' of zone without ending the Identification Period for that Activity Type TABLE 5-continued Rowing/Kayaking Classification Edge Forgiveness is a period where Activity Type can 'drop out' of zone without ending the Identification Period for that Activity Type

| Activity | Classification of Activity Type | Rowing/Kayaking Classification System | | | Measurement Sensor/s | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | | | |
| | | Speed (GPS, Rowing/Kayak Speed device, indoor/mechanical) | | Effort via User Rating | GPS Speed would need smoothing. | | |
| | | | Stroke Rate | 23-32 strokes per min (crew number dependent) | Stroke Rate Sensor | Up Tempo Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | | | |
| | | | Heart Rate | 80 to 90% of AT heart rate or 75-85% HR max (AT HR & AT HR −10 bts) Speed or Heart Rate equivalent to Initial Calibration of 7.5-8.5 of Max Effort via User Rating | Heart Rate | | |
| | Anaerobic Threshold | Speed (GPS, Rowing/Kayak Speed device, indoor/mechanical) | Stroke Rate | 33-37 strokes per min (crew number dependent) | Stroke Rate Sensor | Anaerobic Threshold Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | | | |
| | | | Speed or Power | 93% to 105% of AT Speed 93% to 105% of AT Power Speed or Heart Rate equivalent to Initial Calibration of 8.5-9.5 of Max Effort via User Rating | Rowing/Kayak Speed Device, GPS | | |
| | | Speed (GPS, Rowing/Kayak Speed device, indoor/mechanical) | Stroke Rate | 33-37 strokes per min (crew number dependent) | Stroke Rate Sensor | Anaerobic Threshold Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | | | |
| | | | Heart Rate | 99 to 101% of AT heart rate or 85-95% HR max (AT HR − & +3 bts) Speed or Heart Rate equivalent to Initial Calibration of 8.5-9.5 of Max Effort via User Rating | Heart Rate | | |

TABLE 5-continued

Rowing/Kayaking Classification

| Activity | Classification of Activity Type | Rowing/Kayaking Classification System | | | Measurement Sensor/s GPS Speed would need smoothing. | Example of Output | Edge Forgiveness is a period where Activity Type can 'drop out' of zone without ending the Identification Period for that Activity Type Collected Raw Data over the Identified Activity Period |
|---|---|---|---|---|---|---|---|
| | | Primary Intensity measurement system | Metrics Used (Parameters) | Algorithm also Historic Averages, and Calibration | | | |
| | Starts | Speed (GPS, Rowing/Kayak Speed device, indoor/mechanical) | Stroke Rate | 0 stroke rate up to >36 strokes per min (crew number dependent) | Stroke Rate Sensor | Start Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | Rowing/Kayak Speed Device, GPS | | |
| | | | Speed or Power | 0% up to 95% to 105% of AT Speed 0% up to 95% to 105% of AT Power Speed or Heart Rate equivlent to Intial Calibration of >9 of Max Effort via User Rating | | | |
| | | Speed (GPS, Rowing/Kayak Speed device, indoor/mechanical) | Stroke Rate | 0 stroke rate up to >36 strokes per min (crew number dependent) | Stroke Rate Sensor | Start Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | | | |
| | | | Heart Rate | below 75% up to 99 to 101% of AT heart rate or below 65% up to 85-95% HR max Speed or Heart Rate equivlent to Intial Calibration of >9 of Max Effort via User Rating | Heart Rate | | |
| | Moves | Speed (GPS, Rowing/Kayak Speed device, indoor/mechanical) | Stroke Rate | 33-37 strokes per min (crew number dependent) | Stroke Rate Sensor | Move Identified | Speed, Elapsed Time, Time of Day, Location, Altitude, Force of Movement, Turnover, Distance per Turnover HR, R-R (HRV), ECG, BP, Respiration Rate, Body Temperature, Glucose & Cholesterol Levels, Pulse Oximetry, Strokes Environmental Temp, (water temp) Heat Index, Wind Chill, Altitude, Power Curve, Wind Speed, Weather (rain etc), Distance |
| | | | AND | | Rowing/Kayak Speed Device, GPS | | |
| | | | Speed or Power | >105% of AT Speed >105% of AT Power | | | |

TABLE 5-continued

Rowing/Kayaking Classification

| Activity | Classification of Activity Type | Rowing/Kayaking Classification System ||| Measurement Sensor/s | Example of Output | Collected Raw Data over the Identified Activity Period |
|---|---|---|---|---|---|---|---|
| | | Primary Intensity measurement system | Metrics Used (Parameters) | Algorithm also Historic Averages, and Calibration | | | |
| | | Speed (GPS, Rowing/Kayak Speed device, indoor/mechanical) | | Speed or Heart Rate equivilent to Initial Calibration of >9 of Max Effort via User Rating | GPS Speed would need smoothing. | | Speed, Elapsed Time, Time of Day, Location, Altitude, Force of Movement, Turnover, Distance per Turnover |
| | | | Stroke Rate | 33-37 strokes per min (crew number dependent) | Stroke Rate Sensor | Move Identified | HR, R-R (HRV), ECG, BP, Respiration Rate, Body Temperature, Glucose & Cholesterol Levels, Pulse Oximetry, Strokes |
| | | | AND | | | | Environmental Temp, (water temp) Heat Index, Wind Chill, Altitude, Power Curve, Wind Speed, Weather (rain etc), Distance |
| | | | Heart Rate | >101% of AT heart rate or >95% HR max (>AT HR +3 bts) Speed or Heart Rate equivilent to Initial Calibration of >9 of Max Effort via User Rating | Heart Rate | | |

Edge Forgiveness is a period where Activity Type can 'drop out' of zone without ending the Identification Period for that Activity Type

TABLE 6

Field Sports Classification

| Activity | Classfication of Activity Type | Field Sports Classification System ||| Measurement Sensor/s | Example of Output | Edge Forgiveness is a period where Activity Type can 'drop out' of zone without ending the Identification Period for that Activity Type |
| --- | --- | --- | --- | --- | --- | --- | --- |
| | | Primary Intensity measurement system All areas would be summarised into Totals | Metrics Used (Parameters) | Algorithm also Historic Averages, and Calibration | | | Collected Raw Data over the Identified Activity Period |
| Running | 0-5 m Speed or Power - moving start | Speed (GPS, Accelerometer, video motion capture, RF triangulation) Power direct or indirect (based on body weight & speed) | Speed | Speed >95% of highest 5% of game speed (adjustable) | GPS, Accelerometer, Transmitter to | 0-5 m Speed or Power - moving | Speed, Terrain, Elapsed Time, Time of Day, Location, Altitude, Movement Incidence, Force of Movement, Turnover, Distance per Turnover |
| | | | | Speed at start: >40% of highest 5% of game speed (adjustable) | Transceiver/ Receiver | indentified for a specified loaction on the playing area | HR, R-R (HRV), ECG, BP, Respiration Rate, Body Temperature, Pulse Oximetry, Steps |
| | | | (Body Weight) | Power based on body weight & speed | Video Motion Capture | | Heaviness of Footfall, L-R Power Balance, Force Measures for Gait, |
| | | | | Power >95% of highest 5% of the game (adjustable) | | | Environmental Temp, Heat Index, Wind Chill, Altitude, Slope/Gradient, Wind Speed, Weather (rain etc), Distance |
| | | | | Power at Start: >40% of highest 5% of game power (adjustable) | | | each of the following is listed independently as a location of incidence: Total Center Attacking ⅓, Center Mid field, Center Defensive ⅓, |
| | | | Location | each of the following is listed independently: Total Center Attracting ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver | | Right Flank Attacking ⅓, Right Flank Mid field, Right Flank Defensive ⅓, Left Flank Attacking ⅓, Left Flank Mid field, Left Flank Defensive ⅓, |
| | | | AND Distance or Time Possible Extra: Stride Rate | 0-5 meters or equivilent time | Video Motion Capture Time | | Duration of a game, half or quarter time |
| | | | | >70 strides per min (1 full cycle left & right legs) | Accelerometer | | |
| | 0-5 m Speed or | Speed (GPS, Accelerometer, video | | Speed >95% of highest 5% | GPS, Accelerometer, | 0-5 m Speed or | Speed, Terrain, Elapsed Time, Time of Day, |

TABLE 6-continued

Field Sports Classification

| Activity | Classification of Activity Type | Field Sports Classification System | | | Measurement Sensor/s | Example of Output | Edge Forgiveness is a period where Activity Type can 'drop out' of zone without ending the Identification Period for that Activity Type |
|---|---|---|---|---|---|---|---|
| | | Primary Intensity measurement system All areas would be summarised into Totals | Metrics Used (Parameters) | Algorithm also Historic Averages, and Calibration | | | Collected Raw Data over the Identified Activity Period |
| | Power - stationary start | motion capture, RF triangulation) Power direct or indirect (based on body weight & speed) | Speed | of game speed (adjustable) Speed at start: <40% of highest 5% of game speed (adjustable) | Transmitter to Transceiver/ Receiver Video Motion Capture | Power - stationary identified for a specified loaction on the playing area | Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | (Body Weight) | Power based on body weight & speed Power >95% of highest 5% of the game (adjustable) Power at Start: <40% of highest 5% of game power (adjustable) | GPS, Accelerometer, Transmitter to | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | Transceiver/ Receiver Video Motion Capture | | Right Flank Attacking ⅓, Right Flank Mid field, Right Flank Defensive ⅓, Left Flank Attacking ⅓, Left Flank Mid field, Left Flank Defensive ⅓, |
| | | | AND Distance or Time Possible Extra: Stride Rate | 0-5 meters or equivalent time >10 up to <70 strides per min (1 full cycle left & right legs) | Time Accelerometer | | Duration of a game, half or quarter time |
| | 5-10 m Speed or Power - moving | Speed (GPS, Accelerometer, video motion capture, RF triangulation) Power direct or indirect (based on body weight & | Speed | Speed >90% of highest 5% of game speed (adjustable) Speed at start: >40% of highest 5% of game speed | GPS, Accelerometer, Transmitter to Transceiver/ | 5-10 m Speed or Power - indentified for a specified | Speed, Terrain, Elapsed Time, Time of Day, Location, Altitude, Movement Incidence, Force of Movement, Turnover, Distance per Turnover HR, R-R (HRV), ECG, BP, Respiration Rate, Body |

TABLE 6-continued

Field Sports Classification

| Activity | Classification of Activity Type | Field Sports Classification System ||||  Measurement Sensor/s | Example of Output | Collected Raw Data over the Identified Activity Period |
|---|---|---|---|---|---|---|---|---|
| | | Primary Intensity measurement system All areas would be summarised into Totals | Metrics Used (Parameters) | Algorithm also Historic Averages, and Calibration | | | | Edge Forgiveness is a period where Activity Type can 'drop out' of zone without ending the Identification Period for that Activity Type |
| | start | speed) | (Body Weight) | (adjustable) Power based on body weight & speed | | Receiver Video Motion Capture | loaction on the playing area | Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | | Power >90% of highest 5% of the game (adjustable) Power at Start: >40% of highest 5% of game power (adjustable) | | | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | | GPS, Accelerometer, Transmitter to Transceiver/ Receiver | | Right Flank Attacking ⅓, Right Flank Mid field, Right Flank Defensive ⅓, Left Flank Attacking ⅓, Left Flank Mid field, Left Flank Defensive ⅓, |
| | | | AND Distance or Time Possible Extra: Stride Rate | 5-10 meters or equivilent time >70 strides per min (1 full cycle left & right legs) | | Video Motion Capture Time Accelerometer | | Duration of a game, half or quarter time |
| | 5-10 m Speed or Power - stationary start | Speed (GPS, Accelerometer, video motion capture, RF triangulation) Power direct or indirect (based on body weight & speed) | Speed (Body Weight) | Speed >90% of highest 5% of game speed (adjustable) Speed at start: <40% of highest 5% of game speed (adjustable) Power based on body weight & speed | | GPS, Accelerometer, Transmitter to Transceiver/ Receiver Video Motion Capture | 5-10 m Speed or Power - stationary indentifed for a specified loaction on the playing area | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, |

TABLE 6-continued

Field Sports Classification

| Activity | Classification of Activity Type | Field Sports Classification System | | | | |
|---|---|---|---|---|---|---|
| | | Primary Intensity measurement system All areas would be summarised into Totals | Metrics Used (Parameters) | Algorithm also Historic Averages, and Calibration | Measurement Sensor/s | Example of Output | Collected Raw Data over the Identified Activity Period |

Edge Forgiveness is a period where Activity Type can 'drop out' of zone without ending the Identification Period for that Activity Type

| | | | | Power >90% of highest 5% of the game (adjustable) Power at Start: <40% of highest 5% of game power (adjustable) | GPS Speed would need smoothing. | | Altitude, Slope/Gradient, Wind Speed, Weather (rain etc), Distance |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, |
| | | | AND Distance or Time Possible Extra: Stride Rate | 5-10 meters or equivalent time >10 up to <70 strides per min (1 full cycle left & right legs) | Video Motion Capture Time Accelerometer | | Duration of a game, half or quarter time |
| | 10-20 m Speed or Power - moving | Speed (GPS, Accelerometer, video motion capture, RF triangulation) Power direct or indirect (based on body weight & speed) | Speed (Body Weight) | Speed >85% of highest 5% of game speed (adjustable) Speed at start: >40% of highest 5% of game speed (adjustable) Power based on body weight & speed Power >85% of highest 5% of the game (adjustable) | GPS, Accelerometer, Transmitter to Transceiver/ Receiver Video Motion Capture | 10-20 m Speed or Power - moving identified for a specified loaction on the playing area | Speed, Terrain, Elapsed Time, Time of Day, Location, Altitude, Movement Incidence, Force of Movement, Turnover, Distance per Turnover |
| | start | | | | | | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |

TABLE 6-continued

Field Sports Classification

| Activity | Classification of Activity Type | Field Sports Classification System | | | | | Edge Forgiveness is a period where Activity Type can 'drop out' of zone without ending the Identification Period for that Activity Type |
|---|---|---|---|---|---|---|---|
| | | Primary Intensity measurement system All areas would be summarised into Totals | Metrics Used (Parameters) | Algorithm also Historic Averages, and Calibration | Measurement Sensor/s | Example of Output | Collected Raw Data over the Identified Activity Period |
| | | | | Power at Start: >40% of highest 5% of game power (adjustable) | GPS Speed would need smoothing. | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver Video Motion Capture | | Right Flank Attacking ⅓, Right Flank Mid field, Right Flank Defensive ⅓, Left Flank Attacking ⅓, Left Flank Mid field, Left Flank Defensive ⅓, Duration of a game, half or quarter time |
| | | | AND Distance or Time Possible Extra: Stride Rate | 10-20 meters or equivilent time >70 strides per min (1 full cycle left & right legs) | Time Accelerometer | | |
| 10-20 m Speed or Power - stationary start | | Speed (GPS, Accelerometer, video motion capture, RF triangulation) Power direct or indirect (based on body weight & speed) | Speed (Body Weight) | Speed >85% of highest 5% of game speed (adjustable) Speed at start: <40% of highest 5% of game speed (adjustable) Power based on body weight & speed Power >85% of highest 5% of the game (adjustable) Power at Start: <40% of highest 5% of game power (adjustable) each of the following is | GPS, Accelerometer, Transmitter to Transceiver/ Receiver Video Motion Capture GPS, | 10-20 m Speed or Power - stationary identified for a specified loaction on the playing area | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance each of the following is listed independently as a location of incidence: Total Center Attacking ⅓, Center Mid field, Center Defensive ⅓, Right Flank Attacking ⅓, Right Flank Mid field, |

TABLE 6-continued

Field Sports Classification

| Activity | Classification of Activity Type | Field Sports Classification System | | | | Edge Forgiveness is a period where Activity Type can 'drop out' of zone without ending the Identification Period for that Activity Type | |
|---|---|---|---|---|---|---|---|
| | | Primary Intensity measurement system All areas would be summarised into Totals | Metrics Used (Parameters) | Algorithm also Historic Averages, and Calibration | Measurement Sensor/s | Example of Output | Collected Raw Data over the Identified Activity Period |
| | | | Location | listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | Accelerometer, Transmitter to Transceiver/ Receiver Video Motion Capture | | Right Flank Defensive ⅓, Left Flank Attacking ⅓, Left Flank Mid field, Left Flank Defensive ⅓, Duration of a game, half or quarter time |
| | | | AND Distance or Time Possible Extra: Stride Rate | 10-20 meters or equivilent time >10 up to <70 strides per min (1 full cycle left & right legs) | Time Accelerometer | | |
| | 20-40 m Speed or Power - moving start | Speed (GPS, Accelerometer, video motion capture, RF triangulation) Power direct or indirect (based on body weight & speed) | Speed (Body Weight) | Speed >80% of highest 5% of game speed (adjustable) Speed at start: >40% of highest 5% of game speed (adjustable) Power based on body weight & speed Power >85% of highest 5% of the game (adjustable) Power at Start: >40% of highest 5% of game power (adjustable) | GPS, Accelerometer, Transmitter to Transceiver/ Receiver Video Motion Capture | 20-40 m Speed or Power - moving identified for a specified loaction on the playing area | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | Location | each of the following is listed independently: Total Center Attacking ⅓, | GPS, Accelerometer, Transmitter to | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, |

TABLE 6-continued

Field Sports Classification

| Activity | Classification of Activity Type | Field Sports Classification | | | | |
|---|---|---|---|---|---|---|
| | | Primary Intensity measurement system All areas would be summarised into Totals | Metrics Used (Parameters) | Algorithm also Historic Averages, and Calibration | Measurement Sensor/s | Example of Output | Collected Raw Data over the Identified Activity Period |

Edge Forgiveness is a period where Activity Type can 'drop out' of zone without ending the Identification Period for that Activity Type

| | | | | Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓; (adjustable) | Transceiver/ Receiver | | Duration of a game, half or quarter time |
| | | | | | Video Motion Capture | | |
| | | | AND Distance or Time Possible Extra: Stride Rate | 20-40 meters or equivilent time | Time | | |
| | | | | >70 strides per min (1 full cycle left & right legs) | Accelerometer | | |
| 20-40 m Speed or Power - stationary start | | Speed (GPS, Accelerometer, video motion capture, RF triangulation) Power direct or indirect (based on body weight & speed) | Speed | Speed >80% of highest 5% of game speed (adjustable) Speed at start: <40% of highest 5% of game speed (adjustable) | GPS, Accelerometer, Transmitter to Transceiver/ Receiver | 20-40 m Speed or Power - stationary identified for a specified loaction on the playing area | Speed, Terrain, Elapsed Time, Time of Day, Location, Altitude, Movement Incidence, Force of Movement, Turnover, Distance per Turnover |
| | | | (Body Weight) | Power based on body weight & speed Power >80% of highest 5% of the game (adjustable) Power at Start: <40% of highest 5% of game power (adjustable) | Video Motion Capture | | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, | GPS, Accelerometer, Transmitter to Transceiver/ Receiver | | Right Flank Attacking ⅓, Right Flank Mid field, Right Flank Defensive ⅓, Left Flank Attacking ⅓, Left Flank Mid field, Left Flank Defensive ⅓, |
| | | | | | Video Motion | | Duration of a game, half or quarter time |

TABLE 6-continued

Field Sports Classification

| Activity | Classification of Activity Type | Field Sports Classification System ||||| Example of Output | Collected Raw Data over the Identified Activity Period |
|---|---|---|---|---|---|---|---|---|
| | | Primary Intensity measurement system All areas would be summarised into Totals | Metrics Used (Parameters) | Algorithm also Historic Averages, and Calibration | Measurement Sensor/s | | | |
| | | | | Right Flank Defensive ⅓, Left Flank Attacking ⅓, Left Flank Mid field, Left Flank Defensive ⅓, (adjustable) | Capture | | GPS Speed would need smoothing. | |
| | | | AND Distance or Time Possible Extra: Stride Rate | 20-40 meters or equivilent time >10 up to <70 strides per min (1 full cycle left & right legs) | Time Accelerometer | | | |
| | 40 m+ Speed or Power - moving | Speed (GPS, Accelerometer, video motion capture, RF triangulation) Power direct or indirect (based on body weight & speed) | Speed | Speed >75% of highest 5% of game speed (adjustable) Speed at start: >40% of highest 5% of game speed (adjustable) | GPS, Accelerometer, Transmitter to Transceiver/ Receiver Video Motion Capture | | 40+ m Speed or Power - moving identified for a specified loaction on the playing area | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | start | | (Body Weight) | Power based on body weight & speed Power >75% of highest 5% of the game (adjustable) Power at Start: >40% of highest 5% of game power (adjustable) | | | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, | GPS, Accelerometer, Transmitter to Transceiver/ Receiver Video Motion Capture | | | Right Flank Attacking ⅓, Right Flank Mid field, Right Flank Defensive ⅓, Left Flank Attacking ⅓, Left Flank Mid field, Left Flank Defensive ⅓, Duration of a game, half or quarter time |

Edge Forgiveness is a period where Activity Type can 'drop out' of zone without ending the Identification Period for that Activity Type TABLE 6-continued Field Sports Classification

| Activity | Classification of Activity Type | Field Sports Classification System | | | Measurement Sensor/s | Example of Output | Collected Raw Data over the Identified Activity Period |
|---|---|---|---|---|---|---|---|
| | | Primary Intensity measurement system All areas would be summarised into Totals | Metrics Used (Parameters) | Algorithm also Historic Averages, and Calibration | | | Edge Forgiveness is a period where Activity Type can 'drop out' of zone without ending the Identification Period for that Activity Type |
| | | | | Flank Defensive ⅓, (adjustable) | | | |
| | | | AND Distance or Time Possible Extra: Stride Rate | 40+ meters or equivilent time >70 strides per min (1 full cycle left & right legs) | Accelerometer | | |
| | 40 m+ Speed - stationary start | Speed (GPS, Accelerometer, video motion capture, RF triangulation) Power direct or indirect (based on body weight & speed) | Speed | Speed >75% of highest 5% of game speed (adjustable) Speed at start: <40% of highest 5% of game speed (adjustable) | GPS, Accelerometer, Transmitter to Transceiver/ Receiver | 40+ m Speed or Power - stationary identified for a specified loaction on the playing area | Speed, Terrain, Elapsed Time, Time of Day, Location, Altitude, Movement Incidence, Force of Movement, Turnover, Distance per Turnover |
| | | | (Body Weight) | Power based on body weight & speed Power >75% of highest 5% of the game (adjustable) Power at Start: <40% of highest 5% of game power (adjustable) | Video Motion Capture | | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, |
| | | | AND Distance | 40+ meters or equivilent | Video Motion Capture | | Duration of a game, half or quarter time |

TABLE 6-continued

Field Sports Classification

| Activity | Classification of Activity Type | Field Sports Classification System | | | Measurement Sensor/s | Example of Output | Edge Forgiveness is a period where Activity Type can 'drop out' of zone without ending the Identification Period for that Activity Type |
| --- | --- | --- | --- | --- | --- | --- | --- |
| | | Primary Intensity measurement system All areas would be summarised into Totals | Metrics Used (Parameters) | Algorithm also Historic Averages, and Calibration | | | Collected Raw Data over the Identified Activity Period |
| | | | or Time Possible Extra: Stride Rate | time >10 up to <70 strides per min (1 full cycle left & right legs) | Time Accelerometer | | |
| | Tempo Speed | Speed (GPS, Accelerometer, video motion capture, RF triangulation) Power direct or indirect (based on body weight & speed) | Speed | Speed 60-75% of highest 5% of game speed (adjustable) | GPS, Accelerometer, Transmitter to Transceiver/ Receiver | Tempo Speed Identified for a specified loaction on the playing area | Speed, Terrain, Elapsed Time, Time of Day, Location, Altitude, Movement Incidence, Force of Movement, Turnover, Distance per Turnover HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | (Body Weight) | Power based on body weight & speed Power 60-75% of highest 5% of the game (adjustable) | Video Motion Capture | | |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓ (adjustable) | GPS, Accelerometer, Transmitter to Transceiver/ Receiver Video Motion Capture | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, Duration of a game, half or quarter time |

TABLE 6-continued

Field Sports Classification

| Activity | Classification of Activity Type | Field Sports Classification System | | | Measurement Sensor/s | Example of Output | Edge Forgiveness is a period where Activity Type can 'drop out' of zone without ending the Identification Period for that Activity Type |
| | | Primary Intensity measurement system All areas would be summarised into Totals | Metrics Used (Parameters) | Algorithm also Historic Averages, and Calibration | | | Collected Raw Data over the Identified Activity Period |
| --- | --- | --- | --- | --- | --- | --- | --- |
| | | | AND Distance or Time Possible Extra: Stride Rate | Over Duration of Game >70 strides per min (1 full cycle left & right legs) | Time Accelerometer | | |
| | Jogging | Speed (GPS, Accelerometer, video motion capture, RF triangulation) Power direct or indirect (based on body weight & speed) | Speed | Speed 55-60% of highest 5% of game speed (adjustable) | GPS, Accelerometer, Transmitter to Transceiver/ Receiver Video Motion Capture | Jogging Speed Identified for a specified loaction on the playing area | Speed, Terrain, Elapsed Time, Time of Day, Location, Altitude, Movement Incidence, Force of Movement, Turnover, Distance per Turnover |
| | | | (Body Weight) | Power based on body weight & speed Power 55-60% of highest 5% of the game (adjustable) | | | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver Video Motion Capture | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, |
| | | | AND Distance or Time Possible | Over Duration of Game | Time | | Duration of a game, half or quarter time |

TABLE 6-continued

Field Sports Classification

Edge Forgiveness is a period where Activity Type can 'drop out' of zone without ending the Identification Period for that Activity Type

| Activity | Classification of Activity Type | Field Sports Classification System | | | Measurement Sensor/s | Example of Output | Collected Raw Data over the Identified Activity Period |
|---|---|---|---|---|---|---|---|
| | | Primary Intensity measurement system All areas would be summarised into Totals | Metrics Used (Parameters) | Algorithm also Historic Averages, and Calibration | | | |
| | | | Extra: Stride Rate | >70 strides per min (1 full cycle left & right legs) | Accelerometer | | |
| | Walking | Speed (GPS, Accelerometer, video motion capture, RF triangulation) Power direct or indirect (based on body weight & speed) | Speed | Speed <40% of highest 5% of game speed (adjustable) | GPS, Accelerometer, Transmitter to | Walking Speed Identified for a specified loaction on the playing area | Speed, Terrain, Elapsed Time, Time of Day, Location, Altitude, Movement Incidence, Force of Movement, Turnover, Distance per Turnover |
| | | | (Body Weight) | Power based on body weight & speed | Transceiver/ Receiver Video Motion Capture | | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | | Power <40% of highest 5% of the game (adjustable) | | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver Video Motion Capture | | Right Flank Attacking ⅓, Right Flank Mid field, Right Flank Defensive ⅓, Left Flank Attacking ⅓, Left Flank Mid field, Left Flank Defensive ⅓, Duration of a game, half or quarter time |
| | | | AND Distance or Time Possible Extra: Stride Rate | Over Duration of Game <70 strides per min (1 full cycle left & right legs) | Time Accelerometer | | |
| | Stationary - | Speed (GPS, | | | GPS, | Stationary | Speed, Terrain, Elapsed Time, Time of Day, |

TABLE 6-continued

Field Sports Classification

| Activity | Classification of Activity Type | Field Sports Classification System | | | Measurement Sensor/s | Example of Output | Edge Forgiveness is a period where Activity Type can 'drop out' of zone without ending the Identification Period for that Activity Type |
|---|---|---|---|---|---|---|---|
| | | Primary Intensity measurement system All areas would be summarised into Totals | Metrics Used (Parameters) | Algorithm also Historic Averages, and Calibration | | | Collected Raw Data over the Identified Activity Period |
| | Upright (standing) | Accelerometer, video motion capture, RF triangulation) Power direct or indirect (based on body weight & speed) | Speed | Speed >2 km/hr | Accelerometer, Transmitter to | Upright Identified | Location, Altitude, Movement Incidence, Force of Movement, Turnover, Distance per Turnover |
| | | | | | Transceiver/Receiver Video Motion Capture | for a specified loaction on the playing area | HR, R-R (HRV), ECG, BP, Respiration Rate, Body Temperature, Pulse Oximetry, Steps Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | (Body Weight) | Power based on body weight & speed | | | |
| | | | | Power <25 w (adjustable) | GPS, Accelerometer, Transmitter to | | location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | Transceiver/Receiver | | Right Flank Attacking ⅓, Right Flank Mid field, Right Flank Defensive ⅓, Left Flank Attacking ⅓, Left Flank Mid field, Left Flank Defensive ⅓, |
| | | | Postional Status AND | Upright | Video Motion Capture | | |
| | | | Distance or Time | Over Duration of Game | Multi Axis Accelerometer | | Duration of a game, half or quarter time |
| | | | Possible Extra: Stride Rate | <10 strides per min (1 full cycle left & right legs) | Time | | |
| Stationary - Prone | | Speed (GPS, Accelerometer, video motion capture, RF | | | Accelerometer | | |
| | | | | | GPS, Accelerometer, Transmitter | Stationary Prone | Speed, Terrain, Elapsed Time, Time of Day, Location, Altitude, Movement Incidence, Force of |

TABLE 6-continued

Field Sports Classification

| Activity | Classification of Activity Type | Field Sports Classification System | | | | | |
|---|---|---|---|---|---|---|---|
| | | Primary Intensity measurement system All areas would be summarised into Totals | Metrics Used (Parameters) | Algorithm also Historic Averages, and Calibration | Measurement Sensor/s | Example of Output | Collected Raw Data over the Identified Activity Period |
| | | | | | | | Edge Forgiveness is a period where Activity Type can 'drop out' of zone without ending the Identification Period for that Activity Type |
| | (lying on the ground) | triangulation) Power direct or indirect (based on body weight & speed) | Speed | Speed <2 km/hr | GPS Speed would need smoothing. | Identified for a specified loaction on the playing area | Movement, Turnover; Distance per Turnover |
| | | | | | Transceiver/ Receiver | | HR, R-R (HRV), ECG, BP, Respiration Rate, Body Temperature, Pulse Oximetry, Steps |
| | | | | | Video Motion Capture | | Heaviness of Footfall, L-R Power Balance, Force Measures for Gait, |
| | | | (Body Weight) | Power based on body weight & speed | | | Environmental Temp, Heat Index, Wind Chill, Altitude, Slope/Gradient, Wind Speed, Weather (rain etc), Distance |
| | | | | Power <25 w (adjustable) | | | each of the following is listed independently as a location of incidence: Total Center Attacking ⅓, Center Mid field, Center Defensive ⅓, |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver | | Right Flank Attacking ⅓, Right Flank Mid field, Right Flank Defensive ⅓, Left Flank Attacking ⅓, Left Flank Mid field, Left Flank Defensive ⅓, |
| | | | | | Video Motion Capture | | |
| | | | Postional Status AND Distance or Time Possible Extra: | Prone (lying on the ground) | Multi Axis Accelerometer | | Duration of a game, half or quarter time |
| | | | | Over Duration of Game | Time | | |
| | | | Stride Rate | <10 strides per min (1 full cycle left & right legs) | Accelerometer | | |
| Jumping - vertical | | Speed (Accelerometer, barometer, video motion capture, RF triangulation) | Altitude Change | Vertical distance changes by >30 cm (adjustable) | Barometer, Transmitter to Transceiver, | Vertical Jump Identified | Speed, Terrain, Elapsed Time, Time of Day, Location, Altitude, Movement Incidence, Force of Movement, Turnover, Distance per Turnover |

TABLE 6-continued

Field Sports Classification

| Activity | Classfication of Activity Type | Field Sports Classification System | | | Measurement Sensor/s | Example of Output | Collected Raw Data over the Identified Activity Period |
|---|---|---|---|---|---|---|---|
| | | Primary Intensity measurement system All areas would be summarised into Totals | Metrics Used (Parameters) | Algorithm also Historic Averages, and Calibration | | Edge Forgiveness is a period where Activity Type can 'drop out' of zone without ending the Identification Period for that Activity Type | |
| | | | | | GPS Speed would need smoothing. or Receiver, video motion capture | for a specified loaction | HR, R-R (HRV), ECG, BP, Respiration Rate, Body Temperature, Pulse Oximetry, Steps |
| | | | Location | each of the following is listed independently: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, (adjustable) | GPS, Accelerometer, Transmitter to Transceiver/ Receiver | on the playing area | Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | | | Video Motion Capture | | each of the following is listed independently as a location of incidence: Total Center Attacking ⅓, Center Mid field, Center Defensive ⅓, Right Flank Attacking ⅓, Right Flank Mid field, Right Flank Defensive ⅓, Left Flank Attacking ⅓, Left Flank Mid field, Left Flank Defensive ⅓, Duration of a game, half or quarter time |
| | | Power direct or indirect (based on body weight & speed) | Power AND Steps | Power increases by more than 100 w (adjustable) Steps = 0 | Accelerometer & Derived Calc | | |
| Jumping - horiontal | | Speed (Accelerometer, barometer, video motion capture, RF triangullation) | AND Speed | Speed >8 km/hr | Accelerometer GPS, Accelerometer, Transmitter to Transceiver/ Receiver, motion capture GPS, | Horizontal Jump Identified | Speed, Terrain, Elapsed Time, Time of Day, Location, Altitude, Movement Incidence, Force of Movement, Turnover, Distance per Turnover |
| | | | | | Accelerometer, Transmitter to | for a specified loaction | HR, R-R (HRV), ECG, BP, Respiration Rate, Body Temperature, Pulse Oximetry, Steps |
| | | | Location | each of the following is listed independently: Total Center Attacking ⅓, Center Mid field, Center Defensive ⅓, Right Flank Attacking ⅓, Right Flank Mid field, Right Flank Defensive | Transceiver/ Receiver | on the playing area | Heaviness of Footfall, L-R Power Balance, Force Measures for Gait, Environmental Temp, Heat Index, Wind Chill, Altitude, Slope/Gradient, Wind Speed, Weather (rain etc), Distance |
| | | | | | Video Motion | | each of the following is listed independently as a location of incidence: Total Center Attacking ⅓, |

TABLE 6-continued

Field Sports Classification

| Activity | Classification of Activity Type | Field Sports Classification System ||| Measurement Sensor/s | Example of Output |
|---|---|---|---|---|---|---|
| | | Primary Intensity measurement system All areas would be summarised into Totals | Metrics Used (Parameters) | Algorithm also Historic Averages, and Calibration | | Edge Forgiveness is a period where Activity Type can 'drop out' of zone without ending the Identification Period for that Activity Type. Collected Raw Data over the Identified Activity Period |
| | | | ⅓, Left Flank Attacking ⅓, Left Flank Mid field, Left Flank Defensive ⅓, (adjustable) | | GPS Speed would need smoothing. Capture | Center Mid field, Center Defensive ⅓, Right Flank Attacking ⅓; Right Flank Mid field, Right Flank Defensive ⅓, Left Flank Attacking ⅓, Left Flank Mid field, Left Flank Defensive ⅓, Duration of a game, half or quarter time |
| | | | AND | | Accelerometer & Derived Calc | |
| | Power direct or indirect (based on body weight & speed) | Power AND Steps | Power increases by more than 100 w (adjustable) Steps = 0 for 0.75 secs | | Accelerometer | |

TABLE 7

Horse Training Classification

| Activity | Classification of Activity Type | Horse Training Classification System | | | | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm | Measurement Sensor/s GPS Speed would need smoothing. GPS Altitude would require error correction. | | Collected Raw Data over the Identified Activity Period |
| | Stationary | Speed or Power (GPS, Acclerometer, indoor/mechanical) | Speed | Speed <2 km/hr for more than 15 sec | GPS or Accelerometer | Inactive Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | | or Power | Power <25 w for more than 15 sec | Power (direct or indirect) | | |
| | Easy (Walking) (Zone 2) | Speed (GPS, Acclerometer, indoor/mechanical) | Speed | <14% of AT speed | GPS or Accelerometer | Easy Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, |
| | | | Altitude change (slope, gradient) | Slope <2 degrees (4% gradient) stop: gradient >2 degrees over 6 meters vertical gain stop: gradient >2 degrees >30 secs with 'edge forgiveness' (1-9 secs) | GPS, Barometer, DEM, Inclinometer | | Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | Heart Rate | Heart Rate | <55% of AT HR (<50% of Hrmax) AT HR −10 beats & AT | Heart Rate | Easy Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body |

TABLE 7-continued

Horse Training Classification

| Activity | Classification of Activity Type | Horse Training Classification System | | | | Example of Output | Collected Raw Data over the Identified Activity Period |
|---|---|---|---|---|---|---|---|
| | | Primary Intensity measurement system | Metrics Used (Parameters) | Algorithm | Measurement Sensor/s GPS Speed would need smoothing. GPS Altitude would require error correction. | | |
| | | | Altitude change (slope, gradient) | HR ~40 beats Slope <2 degrees (4% gradient) stop: gradient >2 degrees over 6 meters vertical gain stop: gradient >2 degrees >30 secs with 'edge forgiveness' (1-9 secs) | GPS, Barometer, DEM, Inclinometer | Easy Walking Identified | Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | Power | Power | <14% AT power | Power (direct or indirect) | | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Altitude change (slope, gradient) | Slope <2 degrees (4% gradient) stop: gradient >2 degrees over 6 meters vertical gain stop: gradient >2 degrees >30 secs with 'edge forgiveness' (1-9 secs) | GPS, Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| Easy (Trot) (Zone 2) | | Speed (GPS, Acclerometer, indoor/mechanical) | Speed | 14%-33% of AT speed | GPS or Accelerometer | Trotting Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Altitude change (slope, gradient) | Slope <2 degrees (4% gradient) | GPS, Barometer, DEM, Inclinometer | | Heaviness of Footfall, L-R Power Balance, Force Measures for Gait, Environmental Gas Concentrations, |

Edge Forgiveness is a period where Activity Type can 'drop out' of zone without ending the Identification Period for that Activity Type TABLE 7-continued Horse Training Classification

| Classification | | Horse Training Classification System | | | | |
|---|---|---|---|---|---|---|
| Activity | Activity Type | Primary Intensity measurement system | Metrics Used (Parameters) | Algorithm | Measurement Sensor/s GPS Speed would need smoothing. GPS Altitude would require error correction. | Example of Output | Edge Forgiveness is a period where Activity Type can 'drop out' of zone without ending the Identification Period for that Activity Type / Collected Raw Data over the Identified Activity Period |
| | | | | stop: gradient >2 degrees over 6 meters vertical gain | | | Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | | stop: gradient >2 degrees >30 secs with 'edge forgiveness' (1-9 secs) | | Trotting Identified | Speed, Terrain, Elapsed Time, Time of Day, Location, Altitude, Movement Incidence, Force pf Movement, Turnover, Distance per Turnover |
| | | Heart Rate | Heart Rate | 56-70% of AT HR (51-60% of Hrmax) AT HR −10 beats & AT HR −40 beats | Heart Rate | | HR, R-R (HRV), ECG, BP, Respiration Rate, Body Temperature, Pulse Oximetry, Steps, Gait Analysis |
| | | | Altitude change (slope, gradient) | Slope <2 degrees (4% gradient) | GPS, Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | | stop: gradient >2 degrees over 6 meters vertical gain | | | Weather Forecast, Location of other Users (including information on their Activities), Direction to User is Facing, |
| | | | | stop: gradient >2 degrees >30 secs with 'edge forgiveness' (1-9 secs) | | Trotting Identified | Speed, Terrain, Elapsed Time, Time of Day, Location, Altitude, Movement Incidence, Force pf Movement, Turnover, Distance per Turnover |
| | | Power | Power | 14-33% AT power | Power (direct or indirect) | | HR, R-R (HRV), ECG, BP, Respiration Rate, Body Temperature, Pulse Oximetry, Steps, Gait Analysis |
| | | | Altitude change (slope, gradient) | Slope <2 degrees (4% gradient) | GPS, Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | | stop: gradient >2 degrees over 6 meters vertical gain | | | Weather Forecast, Location of other Users (including information on their Activities), Direction to User is Facing, |
| | | | | stop: gradient >2 degrees >30 secs | | | |

TABLE 7-continued

Horse Training Classification

| Activity | Classification of Activity Type | Horse Training Classification System | | | Example of Output | Collected Raw Data over the Identified Activity Period |
|---|---|---|---|---|---|---|
| | | Primary Intensity measurement system | Metrics Used (Parameters) | Algorithm | | |
| | | | | | | Edge Forgiveness is a period where Activity Type can 'drop out' of zone without ending the Identification Period for that Activity Type |
| | | | | | | Measurement Sensor/s GPS Speed would need smoothing. GPS Altitude would require error correction. |
| | Hills | Speed (GPS, Accelerometer, indoor/mechanical), Heart Rate & Power | Altitude change (slope, gradient) | with 'edge forgiveness' (1-9 secs) gradient >2 degrees (4%) gradient) <8 degrees (15%) >7 m, <20 m vertical gain gradient >2 degrees >70 secs, <200 secs with 'edge forgiveness' (1-9 secs) | Rolling Hill Identified | GPS, Barometer, DEM, Inclinometer | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | Hill Efforts | Speed (GPS, Acclerometer, indoor/mechanical) | Speed | AT Speed − (AT speed * 5%), AT speed * 95% | Hill Effort Identified | GPS or Accelerometer | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Altitude change (slope, gradient) | slope = 2-4 degrees (gradient = 4-7%) stop: gradient >4 degrees (7%) with 'edge forgiveness' (1-9 secs) Minimum Qualifying Window: 1 min | | GPS, Barometer, DEM, Inclinometer | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | | Duration: | | | Time | |
| | | Heart Rate | Heart Rate | 70-80% of Hrmax | Hill Effort Identified | Heart Rate | Speed, Terrain, Elapsed Time, Time of Day, Location, Altitude, Movement Incidence, Force pf Movement, Turnover, Distance per Turnover |

TABLE 7-continued

Horse Training Classification

| Activity | Classification of Activity Type | Horse Training Classification System | | | | Example of Output | Collected Raw Data over the Identified Activity Period |
|---|---|---|---|---|---|---|---|
| | | Primary Intensity measurement system | Metrics Used (Parameters) | Algorithm | Measurement Sensor/s GPS Speed would need smoothing. GPS Altitude would require error correction. | | Edge Forgiveness is a period where Activity Type can 'drop out' of zone without ending the Identification Period for that Activity Type |
| | | | | (Hmax − Hrrest) * % Exercise intensity + Hrrest | | | HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, |
| | | | | AT HR & AT HR −10 beats | | | |
| | | | Altitude change (slope, gradient) | slope = 2-4 degrees (gradient = 4-7%) | GPS, Barometer, DEM, Inclinometer | | Environmental Temp, Heat Index, Wind Chill, Altitude, Slope/Gradient, Wind Speed, Weather (rain etc), Distance |
| | | | | stop: gradient >4 degrees (7%) with 'edge forgiveness' (1-9 secs) | | | Weather Forecast, Location of other Users (including information on their Activities), Direction to User is Facing, |
| | | | Duration: | Minimum Qualifying Window: 1 min | Time | Hill Effort Identified | Speed, Terrain, Elapsed Time, Time of Day, Location, Altitude, Movement Incidence, Force pf Movement, Turnover, Distance per Turnover |
| | | Power | Power | 76-90% of AT power | Power (direct or indirect) | | HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, |
| | | | Altitude change (slope, gradient) | slope = 2-4 degrees (gradient = 4-7%) | GPS, Barometer, DEM, Inclinometer | | Environmental Temp, Heat Index, Wind Chill, Altitude, Slope/Gradient, Wind Speed, Weather (rain etc), Distance |
| | | | | stop: gradient >4 degrees (7%) with 'edge forgiveness' (1-9 secs) | | | Weather Forecast, Location of other Users (including information on their Activities), Direction to User is Facing. |
| | | | Duration: | Minimum Qualifying Window: 1 min | Time | | Speed, Terrain, Elapsed Time, Time of Day, Location, Altitude, Movement Incidence, Force pf Movement, Turnover, Distance per Turnover |
| | Up Tempo (Canter) (Zone 3) | Speed (GPS, Acclerometer, indoor/mechanical) | Speed | 33-65% of AT Speed AT Speed − (AT speed * 5%), AT speed * 95% | GPS or Accelerometer | Canter identified | HR, R-R (HRV), ECG, BP, Respiration Rate, Body Temperature, Pulse Oximetry, Steps, Gait Analysis |
| | | | Altitude | | GPS, | | |

TABLE 7-continued

Horse Training Classification

| Classification of Activity Type | | Horse Training Classification System | | | Example of Output | Collected Raw Data over the Identified Activity Period |
|---|---|---|---|---|---|---|
| Activity | Primary Intensity measurement system | Metrics Used (Parameters) | Algorithm | Measurement Sensor/s GPS Speed would need smoothing. GPS Altitude would require error correction. | | Edge Forgiveness is a period where Activity Type can 'drop out' of zone without ending the Identification Period for that Activity Type |
| | | change (slope, gradient) | Slope <2 degrees (4% gradient), >-2 degrees<br><br>stop: gradient >2 degrees over 3 meters vertical gain<br><br>stop: gradient >2 degrees >15 secs<br>with 'edge forgiveness' (1-9 secs)<br>Minimum Qualifying | Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | Duration: | Window: 1 min | Time | Canter identified | Speed, Terrain, Elapsed Time, Time of Day, Location, Altitude, Movement Incidence, Force pf Movement, Turnover, Distance per Turnover |
| | Heart Rate | Heart Rate | 71-85% of AT HR (61-70% of Hrmax)<br>AT HR & AT HR −10 beats | Heart Rate | | HR, R-R (HRV), ECG, BP, Respiration Rate, Body Temperature, Pulse Oximetry, Steps, Gait Analysis |
| | | Altitude change (slope, gradient) | Slope <2 degrees (4% gradient), >-2 degrees<br><br>stop: gradient >2 degrees over 3 meters vertical gain<br><br>stop: gradient >2 degrees >15 secs<br>with 'edge forgiveness' (1-9 secs)<br>Minimum Qualifying | GPS, Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | Duration: | Window: 1 min | Time | Canter identified | Speed, Terrain, Elapsed Time, Time of Day, Location, Altitude, Movement Incidence, Force pf Movement, Turnover, Distance per Turnover |
| | Power | Power<br>Altitude change (slope, gradient) | 33-65% of AT power<br><br>Slope <2 degrees (4% gradient), >-2 degrees | Power (direct or indirect) GPS, Barometer, DEM, Inclinometer | | HR, R-R (HRV), ECG, BP, Respiration Rate, Body Temperature, Pulse Oximetry, Steps, Gait Analysis Heaviness of Footfall, L-R Power Balance, Force |

TABLE 7-continued

Horse Training Classification

| Activity | Classification of Activity Type | Horse Training Classification System | | | Example of Output | Edge Forgiveness is a period where Activity Type can 'drop out' of zone without ending the Identification Period for that Activity Type |
|---|---|---|---|---|---|---|
| | | Primary Intensity measurement system | Metrics Used (Parameters) | Algorithm | | Measurement Sensor/s GPS Speed would need smoothing, GPS Altitude would require error correction. |
| | Anaerobic Threshold (Gallop) (Zone 4) | Speed (GPS, Accelerometer, indoor/mechanical) | Speed | 65-95% of AT Speed AT Speed − (AT speed * 5%), AT speed * 95% | Gallop identified | GPS or Accelerometer |
| | | | Altitude change (slope, gradient) | Slope <2 degrees (4% gradient), >−2 degrees stop: gradient >2 degrees over 3 meters vertical gain stop: gradient >2 degrees >15 secs with 'edge forgiveness' (1-9 secs) Minimum Qualifying Window: 1 min | | GPS, Barometer, DEM, Inclinometer |
| | | | Duration: | | | Time |
| | Heart Rate | Heart Rate | Heart Rate | 80-90% of Hrmax AT HR +/−5 beats | Gallop identified | Heart Rate |
| | | | Altitude change (slope, gradient) | Slope <2 degrees (4% gradient), >−2 degrees | | GPS, Barometer, DEM, Inclinometer |

Column 7 (Edge Forgiveness) detailed contents per row:

- Row 1 (Speed, Anaerobic Threshold Gallop): Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing.

- Top row: Collected Raw Data over the Identified Activity Period Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing.

- Heart Rate row: Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, TABLE 7-continued Horse Training Classification

| Activity | Classification of Activity Type | Horse Training Classification System ||| Example of Output | Collected Raw Data over the Identified Activity Period |
|---|---|---|---|---|---|---|
| | | Primary Intensity measurement system | Metrics Used (Parameters) | Algorithm | | |
| | | | | stop: gradient >2 degrees over 3 meters vertical gain | | Altitude, Slope/Gradient, Wind Speed, Weather (rain etc), Distance Weather Forecast, Location of other Users (including information on their Activities), Direction to User is Facing. |
| | | | | stop: gradient >2 degrees >15 secs with 'edge forgiveness' (1-9 secs) Minimum Qualifying | | |
| | | | Duration: | Window: 1 min | Gallop identified | Speed, Terrain, Elapsed Time, Time of Day, Location, Altitude, Movement Incidence, Force pf Movement, Turnover, Distance per Turnover |
| | | Power | Power Altitude change (slope, gradient) | 65-95% of AT power | | HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing. |
| | | | | Slope <2 degrees (4% gradient), >-2 degrees | | |
| | | | | stop: gradient >2 degrees over 3 meters vertical gain | | |
| | | | | stop: gradient >2 degrees >15 secs with 'edge forgiveness' (1-9 secs) Minimum Qualifying | | |
| | | | Duration: | Window: 1 min | | |
| Race Pace (Fast Gallop) | | Speed (GPS, Accelerometer, indoor/mechanical) | Speed | 95-105% of AT Speed AT Speed - (AT speed * 5%), AT speed * 95% | Fast Gallop identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Altitude change (slope, gradient) | Slope <2 degrees (4% gradient), >-2 degrees | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain |
| | | | | stop: gradient >2 degrees | | |

Edge Forgiveness is a period where Activity Type can 'drop out' of zone without ending the Identification Period for that Activity Type Measurement Sensor/s GPS Speed would need smoothing. GPS Altitude would require error correction.

Time

Power (direct or indirect) GPS, Barometer, DEM, Inclinometer

Time

GPS or Accelerometer

GPS, Barometer, DEM, Inclinometer

TABLE 7-continued

Horse Training Classification

| Activity | Classification of Activity Type | Horse Training Classification System ||| Example of Output | Collected Raw Data over the Identified Activity Period |
|---|---|---|---|---|---|---|
| | | Primary Intensity measurement system | Metrics Used (Parameters) | Algorithm | Measurement Sensor/s GPS Speed would need smoothing. GPS Altitude would require error correction. | Edge Forgiveness is a period where Activity Type can 'drop out' of zone without ending the Identification Period for that Activity Type |
| | | | | over 3 meters vertical gain | | etc), Distance Weather Forecast, Location of other Users (including information on their Activities), Direction to User is Facing, |
| | | | Duration: | stop: gradient >2 degrees >15 secs with 'edge forgiveness' (1-9 secs) Minimum Qualifying Window: 1 min | Time | Fast Gallop identified |
| | | Heart Rate | Heart Rate | 95-105% of AT HR (80-90% of Hrmax) | Heart Rate | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | | | | AT HR +/-5 beats | GPS, Barometer, DEM, Inclinometer | |
| | | | Altitude change (slope, gradient) | Slope <2 degrees (4% gradient), >-2 degrees | | |
| | | | | stop: gradient >2 degrees over 3 meters vertical gain | | |
| | | | | stop: gradient >2 degrees >15 secs with 'edge forgiveness' (1-9 secs) Minimum Qualifying | | |
| | | | Duration: | Window: 1 min | Time | Fast Gallop identified |
| | | Power | Power | 95-105% of AT power | Power (direct or indirect) GPS, Barometer, DEM, Inclinometer | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain |
| | | | Altitude change (slope, gradient) | Slope <2 degrees (4% gradient), >-2 degrees | | |
| | | | | stop: gradient >2 degrees over 3 meters vertical gain | | |
| | | | | stop: gradient >2 degrees >15 | | |

TABLE 7-continued

Horse Training Classification

| Activity | Classification of Activity Type | Horse Training Classification System | | | Example of Output | Collected Raw Data over the Identified Activity Period |
|---|---|---|---|---|---|---|
| | | Primary Intensity measurement system | Metrics Used (Parameters) | Algorithm | | |
| | | | | | | Edge Forgiveness is a period where Activity Type can 'drop out' of zone without ending the Identification Period for that Activity Type |
| | | | | | Measurement Sensor/s GPS Speed would need smoothing. GPS Altitude would require error correction. | |
| | Sprint (Zone 5) | Speed (GPS, Accelerometer, indoor/mechanical) | Duration: | secs with 'edge forgiveness' (1-9 secs) Minimum Qualifying Window: 1 min | Time GPS or Accelerometer | etc), Distance Weather Forecast, Location of other Users (including information on their Activities), Direction to User is Facing, |
| | | | Speed | >105% of AT Speed | | Sprint identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Altitude change (slope, gradient) | Slope <2 degrees (4% gradient), >-2 degrees stop: gradient >2 degrees over 3 meters vertical gain stop: gradient >2 degrees >15 secs with 'edge forgiveness' (1-9 secs) Minimum Qualifying Window: 30 secs | GPS, Barometer, DEM, Inclinometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | | Heart Rate | Duration: | | Time | Sprint identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Pulse Oximetry, Steps, Gait Analysis |
| | | | Heart Rate | >105% of AT HR (>90% of Hrmax) AT HR +5 beats, +10 beats | Heart Rate | | Heaviness of Footfall, L-R Power Balance, Force Measures for Gait, Environmental Gas Concentrations, |
| | | | Altitude change (slope, gradient) | Slope <2 degrees (4% gradient), >-2 degrees stop: gradient >2 degrees over 3 meters vertical gain | GPS, Barometer, DEM, Inclinometer | | Environmental Temp, Heat Index, Wind Chill, Altitude, Slope/Gradient, Wind Speed, Weather (rain etc), Distance Weather Forecast, Location of other Users (including |

TABLE 7-continued

Horse Training Classification

| Activity | Classification of Activity Type | Horse Training Classification System ||| Measurement Sensor/s | Example of Output | Edge Forgiveness is a period where Activity Type can 'drop out' of zone without ending the Identification Period for that Activity Type Collected Raw Data over the Identified Activity Period |
|---|---|---|---|---|---|---|---|
| | Primary Intensity measurement system | Metrics Used (Parameters) | Algorithm | | | | |
| | | | stop: gradient >2 degrees >15 secs with 'edge forgiveness' (1-9 secs) Minimum Qualifying Window: 30 secs | GPS Speed would need smoothing. GPS Altitude would require error correction. | | information on their Activities), Direction to User is Facing, |
| | | Duration: | | Time | Sprint identified | Speed, Terrain, Elapsed Time, Time of Day, Location, Altitude, Movement Incidence, Force pf Movement, Turnover, Distance per Turnover |
| | Power | Power | >105% of AT power | Power (direct or indirect) GPS, Barometer, DEM, Inclinometer | | HR, R-R (HRV), ECG, BP, Respirations Rate, Body Temperature, Pulse Oximetry, Steps, Gait Analysis Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | Altitude change (slope, gradient) | Slope <2 degrees (4% gradient), >-2 degrees stop: gradient >2 degrees over 3 meters vertical gain stop: gradient >2 degrees >15 secs with 'edge forgiveness' (1-9 secs) Minimum Qualifying | | | Weather Forecast, Location of other Users (including information on their Activities), Direction to User is Facing, |
| | | Durations: | Window: 30 secs | Time | | |

TABLE 8

| | Pedometer - Walking/Running Classification | | | | | | |
|---|---|---|---|---|---|---|---|
| | Pedometer - Walking/Running Classification System | | | | | Edge Forgiveness is a period where Activity Type can 'drop out' of zone without ending the Identification Period for that Activity Type | |
| Activity | Classification of Activity Type | Primary Intensity measurement system | Metrics Used (Parameters) | Algorithm | Measurement Sensor/s | Example of Output | Collected Raw Data over the Identified Activity Period |
| Inactive | Inactive Stationary | Stride Rate | Positional Status AND | Upright Stride Rate = 0 (stride rate/impacts/movements: <15) | Accelerometer | Inactive Stationary Identified | Speed, Terrain, Elapsed Time, Time of Day, Location, Altitude, Movement Incidence, Force pf Movement, Turnover, Distance per Turnover |
| | | | Stride Rate | | Accelerometer | | HR, R-R (HRV), ECG, BP, Respiration Rate, Body Temperature, Glucose & Cholesterol Levels, Pulse Oximetry, Steps, Gait Analysis |
| | | | Stride Rate Variability | >30 ms stride rate variability over 20 secs | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | Inactive Rest | Stride Rate | Positional Status AND | Prone Stride Rate = 0 (stride rate/impacts/movements: <15) | Accelerometer | Inactive Rest Identified | Speed, Terrain, Elapsed Time, Time of Day, Location, Altitude, Movement Incidence, Force pf Movement, Turnover, Distance per Turnover |
| | | | Stride Rate | | Accelerometer | | HR, R-R (HRV), ECG, BP, Respiration Rate, Body Temperature, Glucose & Cholesterol Levels, Pulse Oximetry, Steps, Gait Analysis |
| | | | Stride Rate Variability | >30 ms stride rate variability over 20 secs | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| Walking | Slow Walk | Stride Rate | Stride Rate AND | 30 to 40 strides per minute >30 secs | Accelerometer | Slow Walking Identified | Speed, Terrain, Elapsed Time, Time of Day, Location, Altitude, Movement Incidence, Force pf Movement, Turnover, Distance per Turnover |
| | | | Stride Rate Variability with edge forgiveness (1-9 secs) | <30 ms stride rate variability over 20 secs or <20 G (a calibration session may be required) | Accelerometer | | HR, R-R (HRV), ECG, BP, Respiration Rate, Body Temperature, Glucose & Cholesterol Levels, Pulse Oximetry, Steps, Gait Analysis |
| | | | | | | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |

TABLE 8-continued

Pedometer - Walking/Running Classification

| Activity | Classification of Activity Type | Pedometer - Walking/Running Classification System | | | Measurement Sensor/s | Example of Output | Edge Forgiveness is a period where Activity Type can 'drop out' of zone without ending the Identification Period for that Activity Type |
|---|---|---|---|---|---|---|---|
| | | Primary Intensity measurement system | Metrics Used (Parameters) | Algorithm | | | Collected Raw Data over the Identified Activity Period |
| | Walk | Stride Rate | Stride Rate AND Stride Rate Variability | 40 to 55 strides per minute >30 secs <30 ms stride rate variability over 20 secs or <20 G (a calibration session may be required) | Accelerometer Accelerometer | Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| | Fast Walk | Stride Rate | Stride Rate AND Stride Rate Variability | 56 to 66 strides per minute >30 secs <20 ms stride rate variability over 20 secs or <20 G (a calibration session may be required) | Accelerometer Accelerometer | Fast Walking Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |
| Running | Jog | Stride Rate | Stride Rate AND Stride Rate Variability | 67 to 75 strides per minute >30 secs <10 ms stride rate variability over 20 secs or >20 G (a calibration session may be required) | Accelerometer Accelerometer | Jogging Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance Weather Forecast, Location of other Users (including information on their Activities), Direction to User is Facing, |

TABLE 8-continued

Pedometer - Walking/Running Classification

| Activity | Pedometer - Walking/Running Classification System | | | | | | |
|---|---|---|---|---|---|---|---|
| | Primary Intensity | | | | | | |
| | Classification of Activity Type | measurement system | Metrics Used (Parameters) | Algorithm | Measurement Sensor/s | Example of Output | Edge Forgiveness is a period where Activity Type can 'drop out' of zone without ending the Identification Period for that Activity Type<br>Collected Raw Data over the Identified Activity Period |
| | Moderate Intensity Run | Stride Rate | Stride Rate AND Stride Rate Variability | 76 to 86 strides per minute >30 secs<br><10 ms stride rate variability over 20 secs or >20 G (a calibration session may be required) | Accelerometer<br>Accelerometer | Running Identified | Speed, Terrain, Elapsed Time, Time of Day, Location, Altitude, Movement Incidence, Force pf Movement, Turnover, Distance per Turnover<br>HR, R-R (HRV), ECG, BP, Respiration Rate, Body Temperature, Glucose & Cholesterol Levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations,<br>Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | High Intensity Run | Stride Rate | Stride Rate AND Stride Rate Variability | 87 to 95 strides per minute >30 secs<br><10 ms stride rate variability over 20 secs or >20 G (a calibration session may be required) | Accelerometer<br>Accelerometer | Fast Running Identified | Speed, Terrain, Elapsed Time, Time of Day, Location, Altitude, Movement Incidence, Force pf Movement, Turnover, Distance per Turnover<br>HR, R-R (HRV), ECG, BP, Respiration Rate, Body Temperature, Glucose & Cholesterol levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations,<br>Environmental Temp, Heat Index, Wind Chill, Altitude, Slope/Gradient, Wind Speed, Weather (rain etc) Distance Weather Forecast, Location of other Users (including information on their Activities), Direction to User is Facing, |
| | Sprint Intensity Run | Stride Rate | Stride Rate AND Stride Rate Variability | 96+ strides per minute >30 secs<br><10 ms stride rate variability over 20 secs or >20 G (a calibration session may be required) | Accelerometer<br>Accelerometer | Sprinting Identified | Speed, Terrain, Elapsed Time, Time of Day, Location, Altitude, Movement Incidence, Force pf Movement, Turnover, Distance per Turnover<br>HR, R-R (HRV), ECG, BP, Respiration Rate, Body Temperature, Glucose & Cholesterol levels, Pulse Oximetry, Steps, Gait Analysis |
| | | | with edge forgiveness (1-9 secs) | | Accelerometer | | Heaviness of Footfall, L-R Power Balance, Force Measures for Gait, Environmental Gas Concentrations,<br>Environmental Temp, Heat Index, Wind Chill, Altitude, Slope/Gradient, Wind Speed, Weather (rain etc) Distance Weather Forecast, Location of other Users (including information on their Activities), Direction to User is Facing, |

TABLE 8-continued

Pedometer - Walking/Running Classification

| Activity | Pedometer - Walking/Running Classification System | | | | Measurement Sensor/s | Example of Output | Edge Forgiveness is a period where Activity Type can 'drop out' of zone without ending the Identification Period for that Activity Type |
|---|---|---|---|---|---|---|---|
| | Primary Intensity | | | | | | Collected Raw Data over the Identified Activity Period |
| | Classification of Activity Type | measurement system | Metrics Used (Parameters) | Algorithm | | | |
| Non Specific Movement - Moderate | | Stride Rate | Stride rate | >15 and <40 strides/impacts/movements per minute | Accelerometer | Non Specific Movement Moderate Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| Intensity | | | AND Stride Rate Variability | >40 ms | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | AND Postural Status | Upright | Accelerometer | | Weather Forecast, Location of other Users (including information on their Activities), Direction to User is Facing, |
| Non Specific Movement - High | | Stride Rate | Stride rate | >40 and <60 strides/impacts/movements per minute | Accelerometer | Non Specific Movement Moderate Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| Intensity | | | AND Stride Rate Variability | >40 ms | Accelerometer | | Heaviness of Footfall, L-R Power Balance, Force Measures For Gait, Environmental Gas Concentrations, Environmental Temp, Heat Index, Wind Chill, Altitude, Slope/Gradient, Wind Speed, Weather (rain etc), Distance |
| | | | AND Postural Status | Upright | Accelerometer | | Weather Forecast, Location of other Users (including information on their Activities), Direction to User is Facing, |
| Non Specific Movement - Very High | | Stride Rate | Stride rate | >60 strides/impacts/movements per minute | Accelerometer | Non Specific Movement Moderate Intensity Identified | Speed, Terrain, Elapsed Time, Time of Day, Location, Altitude, Movement Incidence, Force pf Movement, Turnover, Distance per Turnover HR, R-R (HRV), ECG, BP, Respiration Rate, Body Temperature, Glucose & Cholesterol Levels, Pulse Oximetry, Steps, Gait Analysis |
| Intensity | | | AND Stride Rate Variability | >40 ms | Accelerometer | | Heaviness of Footfall, L-R Power Balance, Force Measures for Gait, Environmental Gas Concentrations, Environmental Temp, Heat Index, Wind Chill, Altitude, Slope/Gradient, Wind Speed, Weather (rain etc), Distance |
| | | | AND Postural Status | Upright | Accelerometer | | Weather Forecast, Location of other Users (including information on their Activities), Direction to User is Facing, |

The foregoing description of the invention includes preferred forms thereof. Modifications may be made thereto without departing from the scope of the invention as defined by the accompanying claims.

The invention claimed is:

1. A method of analyzing an activity session comprising:
   receiving activity data for an activity, the activity data corresponding to multiple parameters;
   retrieving a plurality of sets of threshold criteria for a particular user in view of the activity, wherein each of the sets corresponds to a multi-parameter training zone and comprises at least one threshold criteria related to a speed or a power of the particular user;
   determining an effort of the particular user by comparing the activity data with at least one of a speed threshold or a power threshold of the particular user, wherein the effort comprises an effort percentage relative to the speed threshold or the power threshold of the particular user;
   determining a resistance experienced by the particular user, wherein the resistance comprises a measure based on at least one of stride rate, stroke rate, cadence, or terrain;
   classifying, based on the sets of threshold criteria corresponding to the multi-parameter training zones, multiple durations of the activity into one or more training type segments using the resistance experienced by the particular user and the effort percentage of the particular user; and
   wherein the method is executed by one or more processors.

2. The method of claim 1, wherein the effort percentage comprises a percentage value relative to at least one of an anaerobic threshold of the particular user, an aerobic threshold of the particular user, or a maximum threshold of the particular user.

3. The method of claim 1, wherein the effort is defined using speed and wherein the effort of the particular user comprises a value relative to a speed of the particular user at an anaerobic threshold.

4. The method of claim 1, wherein the effort is defined using power and wherein the effort of the particular user comprises a value relative to a power of the particular user at an anaerobic threshold.

5. The method of claim 4, wherein the anaerobic threshold of the particular user is based on at least one of heart rate data, speed data, or power data of the particular user.

6. The method of claim 4, wherein the anaerobic threshold of the particular user indicates a maximum effort of the particular user during a predetermined period of exercise performed prior to the activity session.

7. The method of claim 1, wherein each of the plurality of sets of threshold criteria comprises one or more values that are based on a user threshold comprising either an anaerobic threshold of the particular user, an aerobic threshold of the particular user, or a maximum threshold of the particular user and wherein the user threshold is determined in view of a ventilation test, a lactate test, a conconi test, or a maximum cardiovascular threshold of the particular user.

8. The method of claim 1, wherein the power threshold is determined by:
   collecting activity data comprising power data during exercise performed by the particular user prior to the activity session;
   forming a plurality of incidence bins containing numbers of incidences of the power data within specific ranges;
   identifying the at least one incidence bin of the plurality of incidence bins with the highest change, wherein the at least one incidence bin corresponds to a power range; and
   updating the power threshold based on the power range of the at least one incidence bin.

9. The method of claim 1, wherein the speed threshold is determined by:
   collecting activity data comprising speed data during exercise performed by the particular user prior to the activity session;
   forming a plurality of incidence bins containing numbers of incidences of the speed data within specific ranges;
   identifying the at least one incidence bin of the plurality of incidence bins with the highest change, wherein the at least one incidence bin corresponds to a speed range; and
   updating the speed threshold based on the speed range of the at least one incidence bin.

10. The method of claim 4, wherein the anaerobic threshold is determined by:
    collecting activity data comprising heart rate data during exercise performed by the particular user prior to the activity session, wherein the heart rate data comprises a heart rate measurement, a heart rate variability, a heart rate change, a relaxation rate, or a change in relaxation rate;
    forming a plurality of incidence bins containing numbers of incidences of the heart rate data within specific ranges;
    identifying the at least one incidence bin of the plurality of incidence bins with the highest change, wherein the at least one incidence bin corresponds to a heart rate data range; and
    updating the anaerobic threshold based on the heart rate data range of the at least one incidence bin.

11. The method of claim 1, wherein at least one of the plurality of sets of threshold criteria comprise a threshold criteria determined based on perceived exertion scale values provided by the particular user during a calibration workout.

12. The method of claim 4 further comprising, receiving, by the one or more processors, the anaerobic threshold of the particular user from the particular user or from another device.

13. The method of claim 4 further comprising, determining, by the one or more processors, the anaerobic threshold of the particular user.

14. The method of claim 1 further comprising, enabling the particular user to manually initiate stamping of the stamped blocks of activity.

15. The method of claim 1, wherein the resistance is based on at least one of a particular stride rate or a change in stride rate, a particular stroke rate or a change in stroke rate, a particular cadence or a change in cadence, or a particular altitude or a change in altitude.

16. The method of claim 1, wherein each of the sets of threshold criteria comprise multiple threshold criteria that define boundaries of one of the multi-parameter training zones and each of the training type segments corresponds to one of the multi-parameter training zones.

17. The method of claim 1, wherein receiving the activity data for the activity comprises receiving the activity data during the activity.

18. The method of claim 1, further comprising:
    accessing a training plan comprising a duration for one of the one or more training type segments;

comparing the duration from the training plan with a duration of the one or more training type segments; and generating a response for the particular user in view of the comparing the duration of the training plan.

19. The method of claim 1 further comprising, updating the training plan based on the comparison with the duration of the one or more training type segments.

20. The method of claim 1, wherein the measure based on terrain comprises a change in one or more of a slope, a gradient, or an altitude.

21. The method of claim 1, wherein the resistance is further based on a body weight, a carried weight, or an arm/leg turnover, wherein the arm/leg turnover is defined by one or more of a distance per arm/leg turnover or a change in distance per arm/leg turnover.

22. The method of claim 1, wherein the activity data is processed in real time or is processed after the activity session, wherein the activity data comprises time, distance, or location stamped blocks of activity data.

23. The method of claim 1, wherein the activity data is received from one or more activity monitoring devices comprising one or more sensing elements arranged to obtain data indicative of the multiple parameters monitored during the activity session.

24. The method of claim 1, wherein the activity data is received in real time, post activity, or post activity session by one or more monitoring devices, either directly or via a communication network or both.

25. The method of claim 1, wherein at least one of the plurality of sets of threshold criteria for the particular user comprises a threshold corresponding to the effort and a threshold corresponding to the resistance, and wherein the at least one set of thresholds is derived at least partly from one or more of historic data associated to the particular user, a threshold in a plan, an ideal zone, an arbitrary threshold, a lactate test threshold, a Conconi test threshold, a ventilation test threshold, an anaerobic threshold of the particular user, or an aerobic threshold of the particular user.

26. A system for analyzing an activity session comprising:
a processor;
a memory operatively coupled to the processor, the processor to:
receive activity data for an activity, the activity data corresponding to multiple parameters;
retrieve a plurality of sets of threshold criteria for a particular user in view of the activity, wherein each of the sets corresponds to a multi-parameter training zone and comprises at least one threshold criteria related to a speed or a power of the particular user;
determine an effort of the particular user in view of the activity data and at least one of a speed threshold or a power threshold of the particular user, wherein the effort comprises an effort percentage relative to the speed threshold or the power threshold of the particular user;
determine a resistance experienced by the particular user, wherein the resistance comprises a measure based on at least one of stride rate, stroke rate, cadence, or terrain; and
classify, based on the sets of threshold criteria corresponding to the multi-parameter training zones, multiple durations of the activity into one or more training type segments using the resistance experienced by the particular user and the effort percentage of the particular user.

27. The system of claim 26, wherein the effort percentage comprises a percentage value relative to at least one of an anaerobic threshold of the particular user, an aerobic threshold of the particular user, or a maximum threshold of the particular user.

28. A non-transitory computer readable media comprising instructions that cause a processor to:
receive activity data during an activity, the activity data corresponding to multiple parameters;
retrieve a plurality of sets of threshold criteria for a particular user in view of the activity, wherein each of the sets corresponds to a multi-parameter training zone and comprises at least one threshold criteria related to a speed or a power of the particular user;
determine an effort of the particular user in view of the activity data and at least one of a speed threshold or a power threshold of the particular user, wherein the effort comprises an effort percentage relative to the speed threshold or the power threshold of the particular user;
determine a resistance experienced by the particular user, wherein the resistance comprises a measure based on at least one of stride rate, stroke rate, cadence, or terrain; and
classify, based on the sets of threshold criteria corresponding to the multi-parameter training zones, multiple durations of the activity into one or more training type segments using the resistance experienced by the particular user and the effort percentage of the particular user.

29. The non-transitory computer readable media of claim 28, wherein the effort percentage comprises a percentage value relative to at least one of an anaerobic threshold of the particular user, an aerobic threshold of the particular user, or a maximum threshold of the particular user.

* * * * *